United States Patent
de Juan, Jr. et al.

(10) Patent No.: US 11,523,898 B2
(45) Date of Patent: Dec. 13, 2022

(54) ACCOMMODATING INTRAOCULAR LENS AND METHODS OF IMPLANTATION

(71) Applicant: ForSight Vision6, Inc., Brisbane, CA (US)

(72) Inventors: Eugene de Juan, Jr., Brisbane, CA (US); Matthew Clarke, Brisbane, CA (US); Guy Oren, Brisbane, CA (US); Nichole Kahn-Dror, Brisbane, CA (US); Efrat Atiya, Brisbane, CA (US); Amana Moriah, Brisbane, CA (US)

(73) Assignee: ForSight Vision6, Inc., South San Francisco, CA (US)

( * ) Notice: Subject to any disclaimer, the term of this patent is extended or adjusted under 35 U.S.C. 154(b) by 673 days.

(21) Appl. No.: 16/345,364

(22) PCT Filed: Oct. 27, 2017

(86) PCT No.: PCT/US2017/058810
§ 371 (c)(1),
(2) Date: Apr. 26, 2019

(87) PCT Pub. No.: WO2018/081595
PCT Pub. Date: May 3, 2018

(65) Prior Publication Data
US 2019/0269500 A1    Sep. 5, 2019

Related U.S. Application Data

(60) Provisional application No. 62/414,571, filed on Oct. 28, 2016.

(51) Int. Cl.
*A61F 2/16*   (2006.01)

(52) U.S. Cl.
CPC .......... *A61F 2/1635* (2013.01); *A61F 2/1618* (2013.01); *A61F 2/1648* (2013.01); *A61F 2002/1681* (2013.01)

(58) Field of Classification Search
CPC .... A61F 2/1635; A61F 2/1618; A61F 2/1648; A61F 2/1613; A61F 2002/1681
See application file for complete search history.

(56) References Cited

U.S. PATENT DOCUMENTS

| 4,159,546 A | 7/1979 | Shearing |
| 4,373,218 A | 2/1983 | Schachar |

(Continued)

FOREIGN PATENT DOCUMENTS

| CA | 2944010 A1 | 10/2015 |
| CN | 101137338 A | 3/2008 |

(Continued)

OTHER PUBLICATIONS

Gimsel,H.V., DeBroff B.M. (2004), "Intraocular lens optic capture." J Cataract Refract Surg Jan. 2004;30(1):200-6.

(Continued)

*Primary Examiner* — Jennifer Dieterle
*Assistant Examiner* — Tiffany P Shipmon
(74) *Attorney, Agent, or Firm* — Mintz Levin Cohn Ferris Glovsky and Popeo, P.C.

(57) ABSTRACT

An accommodating intraocular lens device for treatment of an eye having a lens body; internal support; stabilization system; and force translation arm. The lens body includes an accommodating membrane, an annular element, a static element, and a fixed volume of optical fluid filling a sealed chamber of the lens body. The annular element coupled to the perimeter of the accommodating membrane has a shape deformation membrane configured to undergo displacement relative to the perimeter region. The sealed chamber is formed by inner surfaces of the accommodating membrane, shape deformation membrane, and static element. The force translation arm has a first end operatively coupled to the shape deformation membrane and a free end available and (Continued)

configured to engage a ciliary structure of the eye. The force translation arm is moveable relative to the lens body to cause inward movement of the shape deformation membrane. Related methods, devices, and systems are provided.

23 Claims, 50 Drawing Sheets

(56) References Cited

U.S. PATENT DOCUMENTS

| | | | |
|---|---|---|---|
| 4,485,498 A | 12/1984 | Gimbel | |
| 4,685,921 A | 8/1987 | Peyman | |
| 4,731,078 A | 3/1988 | Stoy et al. | |
| 4,734,095 A | 3/1988 | Siepser | |
| 4,769,035 A | 9/1988 | Kelman | |
| 4,782,820 A | 11/1988 | Woods | |
| 4,787,903 A | 11/1988 | Grendahl | |
| 4,816,030 A | 3/1989 | Robinson | |
| 4,816,031 A | 3/1989 | Pfoff | |
| 4,842,601 A | 6/1989 | Smith | |
| 4,865,601 A | 9/1989 | Caldwell et al. | |
| 4,888,012 A | 12/1989 | Horn et al. | |
| 4,888,016 A | 12/1989 | Langerman | |
| 4,892,543 A | 1/1990 | Turley | |
| 4,932,966 A | 6/1990 | Christie et al. | |
| 4,932,968 A | 6/1990 | Caldwell et al. | |
| 4,957,505 A | 9/1990 | McDonald | |
| 5,066,301 A | 11/1991 | Wiley | |
| 5,171,266 A | 12/1992 | Wiley et al. | |
| 5,171,320 A | 12/1992 | Nishi | |
| RE34,424 E | 10/1993 | Walman | |
| 5,275,623 A | 1/1994 | Sarfarazi | |
| 5,288,293 A | 2/1994 | O'Donnell, Jr. | |
| 5,443,506 A | 8/1995 | Garabet | |
| 5,489,302 A | 2/1996 | Skottun | |
| 5,607,472 A | 3/1997 | Thompson | |
| 5,684,637 A | 11/1997 | Floyd | |
| 5,766,245 A | 6/1998 | Fedorov et al. | |
| 5,774,273 A | 6/1998 | Bornhorst | |
| 5,800,806 A | 9/1998 | Yamamoto | |
| 5,932,205 A | 8/1999 | Wang et al. | |
| 6,013,101 A | 1/2000 | Israel | |
| 6,027,531 A | 2/2000 | Tassignon | |
| 6,096,078 A | 8/2000 | McDonald | |
| 6,117,171 A | 9/2000 | Skottun | |
| 6,120,538 A | 9/2000 | Rizzo, III et al. | |
| 6,143,315 A | 11/2000 | Wang et al. | |
| 6,188,526 B1 | 2/2001 | Sasaya et al. | |
| 6,228,115 B1 | 5/2001 | Hoffmann et al. | |
| 6,261,321 B1 | 7/2001 | Kellan | |
| 6,277,146 B1 | 8/2001 | Peyman et al. | |
| 6,299,641 B1 | 10/2001 | Woods | |
| 6,387,126 B1 | 5/2002 | Cumming | |
| 6,443,985 B1 | 9/2002 | Woods | |
| 6,450,642 B1 | 9/2002 | Jethmalani et al. | |
| 6,493,151 B2 | 12/2002 | Schachar | |
| 6,506,212 B2 | 1/2003 | Zhou et al. | |
| 6,524,340 B2 | 2/2003 | Israel | |
| 6,552,860 B1 | 4/2003 | Alden | |
| 6,558,420 B2 | 5/2003 | Green | |
| 6,592,621 B1 | 7/2003 | Domino | |
| 6,599,317 B1 | 7/2003 | Weinschenk, III et al. | |
| 6,645,246 B1 | 11/2003 | Weinschenk, III et al. | |
| 6,730,123 B1 | 5/2004 | Klopotek | |
| 6,733,122 B1 | 5/2004 | Feurer et al. | |
| 6,749,634 B2 | 6/2004 | Hanna | |
| 6,818,017 B1 | 11/2004 | Shu | |
| 6,836,374 B2 | 12/2004 | Esch et al. | |
| 6,849,091 B1 | 2/2005 | Cumming | |
| 6,851,804 B2 | 2/2005 | Jethmalani et al. | |
| 6,855,164 B2 | 2/2005 | Glazier | |
| 6,860,601 B2 | 3/2005 | Shadduck | |
| 6,930,838 B2 | 8/2005 | Schachar | |
| 6,935,743 B2 | 8/2005 | Shadduck | |
| 6,966,049 B2 | 11/2005 | Lepejian et al. | |
| 6,966,649 B2 | 11/2005 | Shadduck | |
| 7,008,449 B2 | 3/2006 | Willis et al. | |
| 7,025,783 B2 | 4/2006 | Brady et al. | |
| 7,060,094 B2 | 6/2006 | Shahinpoor et al. | |
| 7,068,439 B2 | 6/2006 | Esch et al. | |
| 7,097,660 B2 | 8/2006 | Portney | |
| 7,118,596 B2 | 10/2006 | Zadno-Azizi et al. | |
| 7,118,597 B2 | 10/2006 | Miller et al. | |
| 7,122,053 B2 | 10/2006 | Esch | |
| 7,217,288 B2 | 5/2007 | Esch et al. | |
| 7,220,279 B2 | 5/2007 | Nun | |
| 7,229,476 B2 | 6/2007 | Azar | |
| 7,247,168 B2 | 7/2007 | Esch et al. | |
| 7,256,943 B1 | 8/2007 | Kobrin et al. | |
| 7,261,737 B2 | 8/2007 | Esch et al. | |
| 7,278,739 B2 | 10/2007 | Shadduck | |
| 7,293,873 B2 | 11/2007 | Dai et al. | |
| 7,341,599 B1 | 3/2008 | Peyman | |
| 7,369,321 B1 | 5/2008 | Ren et al. | |
| 7,381,221 B2 | 6/2008 | Lang et al. | |
| 7,384,429 B2 | 6/2008 | Hanna | |
| 7,438,723 B2 | 10/2008 | Esch | |
| 7,453,646 B2 | 11/2008 | Lo | |
| 7,485,144 B2 | 2/2009 | Esch | |
| 7,601,169 B2 | 10/2009 | Phillips | |
| 7,615,056 B2 | 11/2009 | Ayton et al. | |
| 7,637,947 B2 | 12/2009 | Smith et al. | |
| 7,675,686 B2 | 3/2010 | Lo et al. | |
| 7,713,299 B2 | 5/2010 | Brady et al. | |
| 7,753,953 B1 | 7/2010 | Yee | |
| 7,763,069 B2 | 7/2010 | Brady et al. | |
| 7,776,088 B2 | 8/2010 | Shadduck | |
| 7,806,930 B2 | 10/2010 | Brown | |
| 7,854,764 B2 | 12/2010 | Ben Nun | |
| 7,857,850 B2 | 12/2010 | Mentak et al. | |
| 7,883,540 B2 | 2/2011 | Niwa et al. | |
| 7,985,253 B2 | 7/2011 | Cumming | |
| 7,988,285 B2 | 8/2011 | Sandstedt et al. | |
| 8,018,658 B2 | 9/2011 | Lo | |
| 8,034,106 B2 | 10/2011 | Mentak et al. | |
| 8,038,711 B2 | 10/2011 | Clarke | |
| 8,158,712 B2 | 4/2012 | Your | |
| 8,314,927 B2 | 11/2012 | Choi et al. | |
| 8,343,216 B2 | 1/2013 | Brady et al. | |
| 8,377,125 B2 | 2/2013 | Kellan | |
| 8,414,646 B2 | 4/2013 | De Juan, Jr. et al. | |
| 8,500,806 B1 | 8/2013 | Phillips | |
| 8,663,235 B2 | 3/2014 | Tassignon | |
| 8,668,734 B2 | 3/2014 | Hildebrand et al. | |
| 8,715,345 B2 | 5/2014 | DeBoer et al. | |
| 8,715,346 B2 | 5/2014 | de Juan, Jr. et al. | |
| 8,851,670 B2 | 10/2014 | Dai et al. | |
| 8,900,298 B2 | 12/2014 | Anvar et al. | |
| 8,956,408 B2 | 2/2015 | Smiley et al. | |
| 8,968,396 B2 | 3/2015 | Matthews et al. | |
| 8,974,526 B2 | 3/2015 | Bogaert | |
| 9,005,282 B2 | 4/2015 | Chang et al. | |
| 9,044,317 B2 | 6/2015 | Hildebrand et al. | |
| 9,107,748 B2 | 8/2015 | de Juan, Jr. et al. | |
| 9,114,005 B2 | 8/2015 | Simonov et al. | |
| 9,326,846 B2 | 5/2016 | Devita Gerardi et al. | |
| 9,421,089 B2 | 8/2016 | Zadno-Azizi | |
| 9,681,981 B2 | 6/2017 | Stevens | |
| 9,782,291 B2 | 10/2017 | Stevens | |
| 9,814,568 B2 | 11/2017 | Ben Nun | |
| 9,872,763 B2 | 1/2018 | Smiley et al. | |
| 10,166,096 B2 | 1/2019 | Ben Nun | |
| 10,195,018 B2 | 2/2019 | Salahieh et al. | |
| 10,743,983 B2 | 8/2020 | Wortz et al. | |
| 10,751,167 B2 | 8/2020 | Paine | |
| 2001/0001836 A1 | 5/2001 | Cumming | |
| 2002/0188351 A1 | 12/2002 | Laguette | |
| 2003/0060878 A1 | 3/2003 | Shadduck | |
| 2003/0149480 A1 | 8/2003 | Shadduck | |
| 2003/0171809 A1 | 9/2003 | Phillips | |
| 2003/0187501 A1 | 10/2003 | Okada | |
| 2003/0187504 A1 | 10/2003 | Weinschenk et al. | |
| 2004/0006387 A1 | 1/2004 | Kelman | |

(56) References Cited

U.S. PATENT DOCUMENTS

| | | |
|---|---|---|
| 2004/0034417 A1 | 2/2004 | Heyman |
| 2004/0039446 A1 | 2/2004 | McNicholas |
| 2004/0082993 A1 | 4/2004 | Woods |
| 2004/0082995 A1 | 4/2004 | Woods |
| 2004/0111153 A1 | 6/2004 | Woods et al. |
| 2004/0148023 A1 | 7/2004 | Shu |
| 2004/0162612 A1 | 8/2004 | Portney et al. |
| 2004/0169816 A1 | 9/2004 | Esch |
| 2004/0169820 A1 | 9/2004 | Dai et al. |
| 2004/0237971 A1 | 12/2004 | Radhakrishnan et al. |
| 2005/0021138 A1 | 1/2005 | Woods |
| 2005/0060032 A1 | 3/2005 | Magnante et al. |
| 2005/0065534 A1 | 3/2005 | Hohl |
| 2005/0107873 A1 | 5/2005 | Zhou |
| 2005/0113914 A1 | 5/2005 | Miller et al. |
| 2005/0125059 A1 | 6/2005 | Pinchuk et al. |
| 2005/0137703 A1 | 6/2005 | Chen |
| 2005/0251253 A1 | 11/2005 | Gross |
| 2006/0047340 A1 | 3/2006 | Brown |
| 2006/0064162 A1 | 3/2006 | Klima |
| 2006/0100701 A1 | 5/2006 | Esch et al. |
| 2006/0134173 A1 | 6/2006 | Liu et al. |
| 2006/0238702 A1 | 10/2006 | Glick et al. |
| 2006/0259138 A1 | 11/2006 | Peyman |
| 2007/0010881 A1 | 1/2007 | Soye et al. |
| 2007/0054131 A1 | 3/2007 | Stewart |
| 2007/0078515 A1 | 4/2007 | Brady |
| 2007/0088433 A1 | 4/2007 | Esch et al. |
| 2007/0100444 A1 | 5/2007 | Brady et al. |
| 2007/0123982 A1 | 5/2007 | Yablonski et al. |
| 2007/0129798 A1 | 6/2007 | Chawdhary |
| 2007/0129800 A1 | 6/2007 | Cumming |
| 2007/0129801 A1 | 6/2007 | Cumming |
| 2008/0046075 A1 | 2/2008 | Esch et al. |
| 2008/0046076 A1 | 2/2008 | Rombach |
| 2008/0097459 A1 | 4/2008 | Kammerlander et al. |
| 2008/0103592 A1 | 5/2008 | Maloney |
| 2008/0106698 A1 | 5/2008 | Dai et al. |
| 2008/0119864 A1 | 5/2008 | Deinzer et al. |
| 2008/0125862 A1 | 5/2008 | Blake |
| 2008/0129962 A1 | 6/2008 | Dai et al. |
| 2008/0288066 A1 | 11/2008 | Cumming |
| 2009/0005865 A1 | 1/2009 | Smiley et al. |
| 2009/0012609 A1 | 1/2009 | Geraghty et al. |
| 2009/0171458 A1 | 7/2009 | Kellan et al. |
| 2009/0234449 A1 | 9/2009 | De Juan, Jr. et al. |
| 2009/0292355 A1 | 11/2009 | Boyd et al. |
| 2010/0094415 A1 | 4/2010 | Bumbalough |
| 2010/0121444 A1 | 5/2010 | Ben Nun |
| 2011/0054600 A1 | 3/2011 | Bumbalough |
| 2011/0071628 A1 | 3/2011 | Gross et al. |
| 2011/0118834 A1 | 5/2011 | Lo et al. |
| 2012/0168422 A1 | 7/2012 | Boyd et al. |
| 2012/0253459 A1 | 10/2012 | Reich et al. |
| 2013/0013061 A1 | 1/2013 | Coroneo |
| 2013/0041382 A1 | 2/2013 | Ben Nun |
| 2013/0110235 A1 | 5/2013 | Schwiegerling |
| 2013/0116781 A1 | 5/2013 | Ben Nun |
| 2013/0245754 A1 | 9/2013 | Blum et al. |
| 2014/0012240 A1 | 1/2014 | Ho et al. |
| 2014/0058507 A1 | 2/2014 | Reich et al. |
| 2014/0074074 A1 | 3/2014 | Dick et al. |
| 2014/0121768 A1 | 5/2014 | Simpson |
| 2014/0180403 A1 | 6/2014 | Silvestrini et al. |
| 2014/0228949 A1 | 8/2014 | Argento et al. |
| 2015/0150676 A1 | 6/2015 | Nun |
| 2015/0250584 A1 | 9/2015 | Blum et al. |
| 2015/0257874 A1 | 9/2015 | Hildebrand et al. |
| 2016/0030161 A1* | 2/2016 | Brady ............... A61F 2/1635 623/6.13 |
| 2017/0181850 A1* | 6/2017 | de Juan, Jr. ............ A61F 9/0017 |
| 2017/0342096 A1 | 11/2017 | Silvestrini |
| 2018/0177589 A1 | 6/2018 | Argento et al. |
| 2019/0038401 A1 | 2/2019 | Reich et al. |
| 2019/0183637 A1 | 6/2019 | Ben Nun |
| 2019/0223998 A1 | 7/2019 | de Juan, Jr. et al. |
| 2019/0223999 A1 | 7/2019 | Nun |
| 2020/0188088 A1 | 6/2020 | Reich et al. |

FOREIGN PATENT DOCUMENTS

| | | |
|---|---|---|
| CN | 101795642 A | 8/2010 |
| CN | 103025271 A | 4/2013 |
| CN | 103096837 A | 5/2013 |
| CN | 105392448 A | 3/2016 |
| EP | 0 162 573 A2 | 11/1985 |
| EP | 1917932 A1 | 5/2008 |
| EP | 1932492 A1 | 6/2008 |
| JP | 2005169131 A | 6/2005 |
| JP | 2005533611 A | 11/2005 |
| JP | 2008183434 A | 8/2008 |
| JP | 2008532617 A | 8/2008 |
| JP | 2009532176 A | 9/2009 |
| JP | 2011500270 A | 1/2011 |
| JP | 2016525432 A | 8/2016 |
| WO | WO-93/03686 A2 | 3/1993 |
| WO | WO-03/000154 A2 | 1/2003 |
| WO | WO-03/017867 A2 | 3/2003 |
| WO | WO-03/017873 A1 | 3/2003 |
| WO | WO-2004/010905 A2 | 2/2004 |
| WO | WO-2004/037122 A2 | 5/2004 |
| WO | WO-2004/037127 A2 | 5/2004 |
| WO | WO-2004/053568 A1 | 6/2004 |
| WO | WO-2004/107024 A1 | 12/2004 |
| WO | WO-2005/057272 A2 | 6/2005 |
| WO | WO-2005/082285 A1 | 9/2005 |
| WO | WO-2007/113832 A2 | 10/2007 |
| WO | WO-2007/117476 A2 | 10/2007 |
| WO | WO-2008/031231 A1 | 3/2008 |
| WO | WO-2009/055099 A1 | 4/2009 |
| WO | WO-2010/010565 A2 | 1/2010 |
| WO | WO-2012/006186 A2 | 1/2012 |
| WO | WO-2012/023133 A1 | 2/2012 |
| WO | WO-2012/067994 A2 | 5/2012 |
| WO | WO-2013/016804 A1 | 2/2013 |
| WO | WO-2015/066502 A1 | 5/2015 |
| WO | WO-2015/148673 A1 | 10/2015 |
| WO | WO-2017/087358 A1 | 5/2017 |
| WO | WO-2017/096087 A1 | 6/2017 |
| WO | WO-2018/222579 A1 | 12/2018 |
| WO | WO-2018/227014 A1 | 12/2018 |
| WO | WO-2020/206343 A1 | 10/2020 |

OTHER PUBLICATIONS

U.S. Appl. No. 14/621,305, filed Feb. 12, 2015, US 2015-0150676.
U.S. Appl. No. 15/914,907, filed Mar. 7, 2018, US 2019-0038401.
U.S. Appl. No. 16/228,454, filed Dec. 20, 2018, US 2019-0183637.
U.S. Appl. No. 16/372,746, filed Apr. 2, 2019, US 2019-0223999.
U.S. Appl. No. 16/372,090, filed Apr. 1, 2019, US 2019-0223998.
U.S. Appl. No. 17/166,680, filed Feb. 3, 2021, US 2021-0259826.
U.S. Appl. No. 17/221,525, filed Apr. 2, 2021, US 2021-0290372.
U.S. Appl. No. 17/364,202, filed Jun. 30, 2021, US 2022-0160495.
U.S. Appl. No. 17/600,571, filed Sep. 30, 2021, US 2022-0168464.
PCT/US21/37354, Jun. 15, 2021, WO 2021/257518.

* cited by examiner

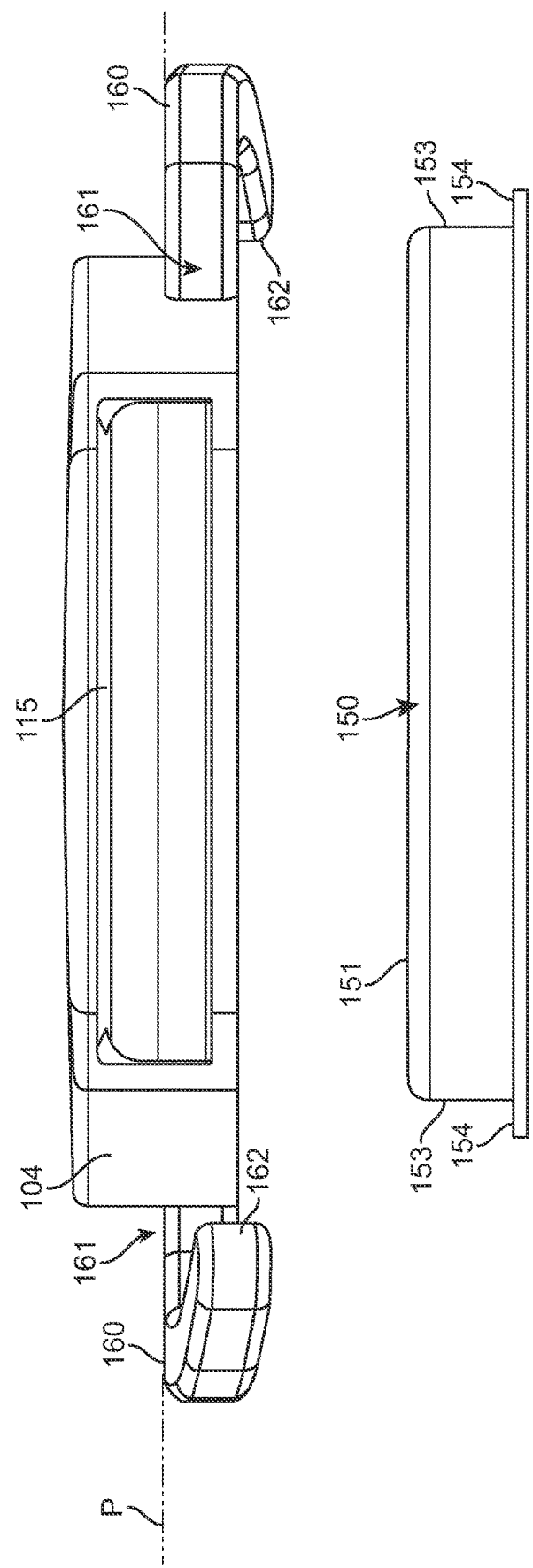

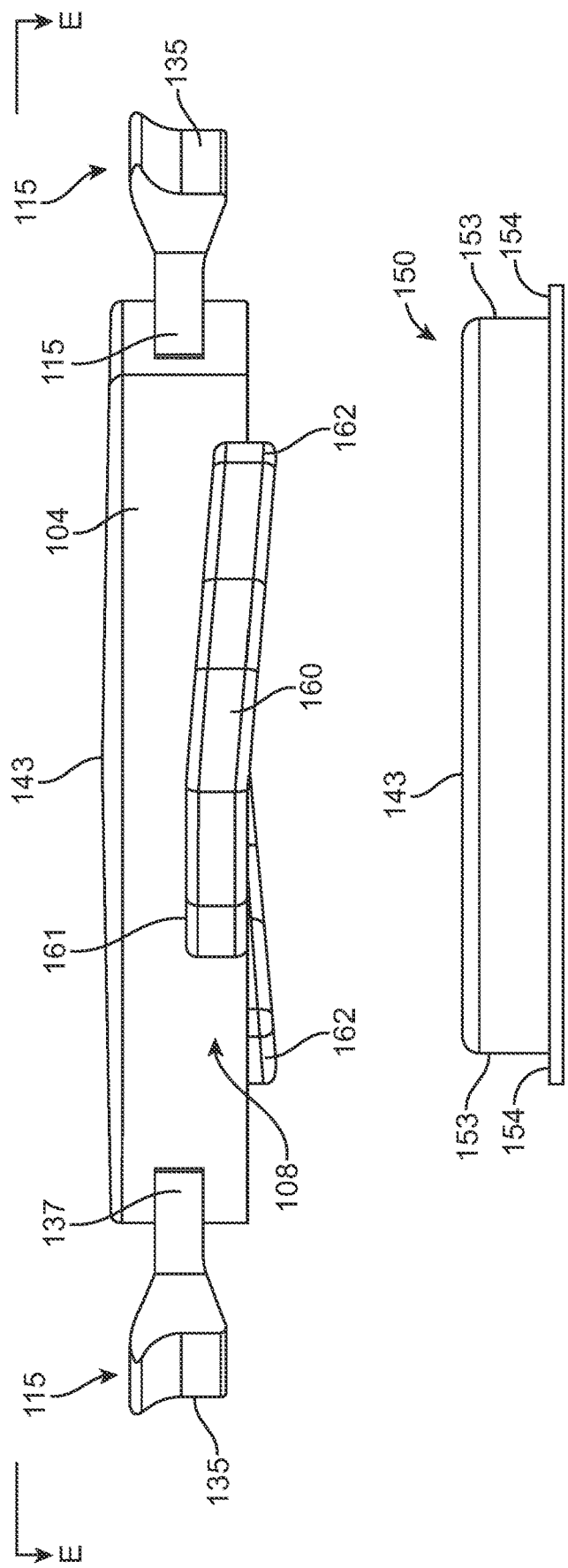

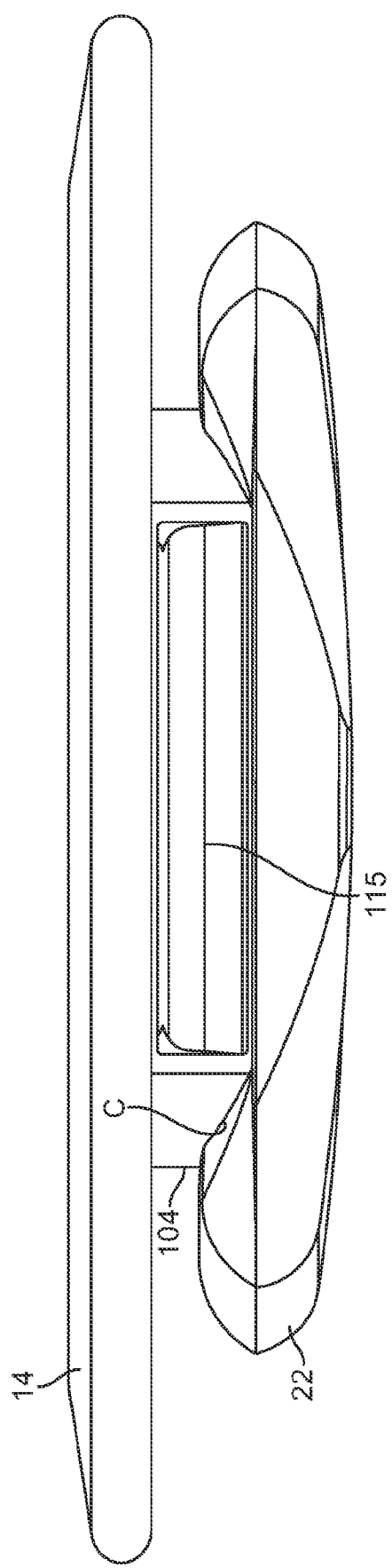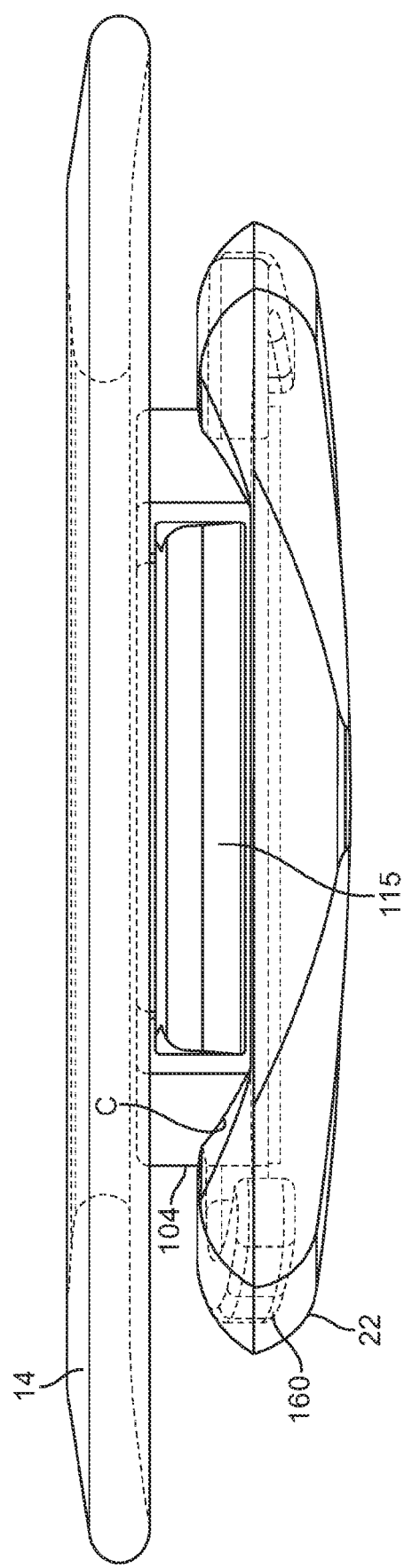

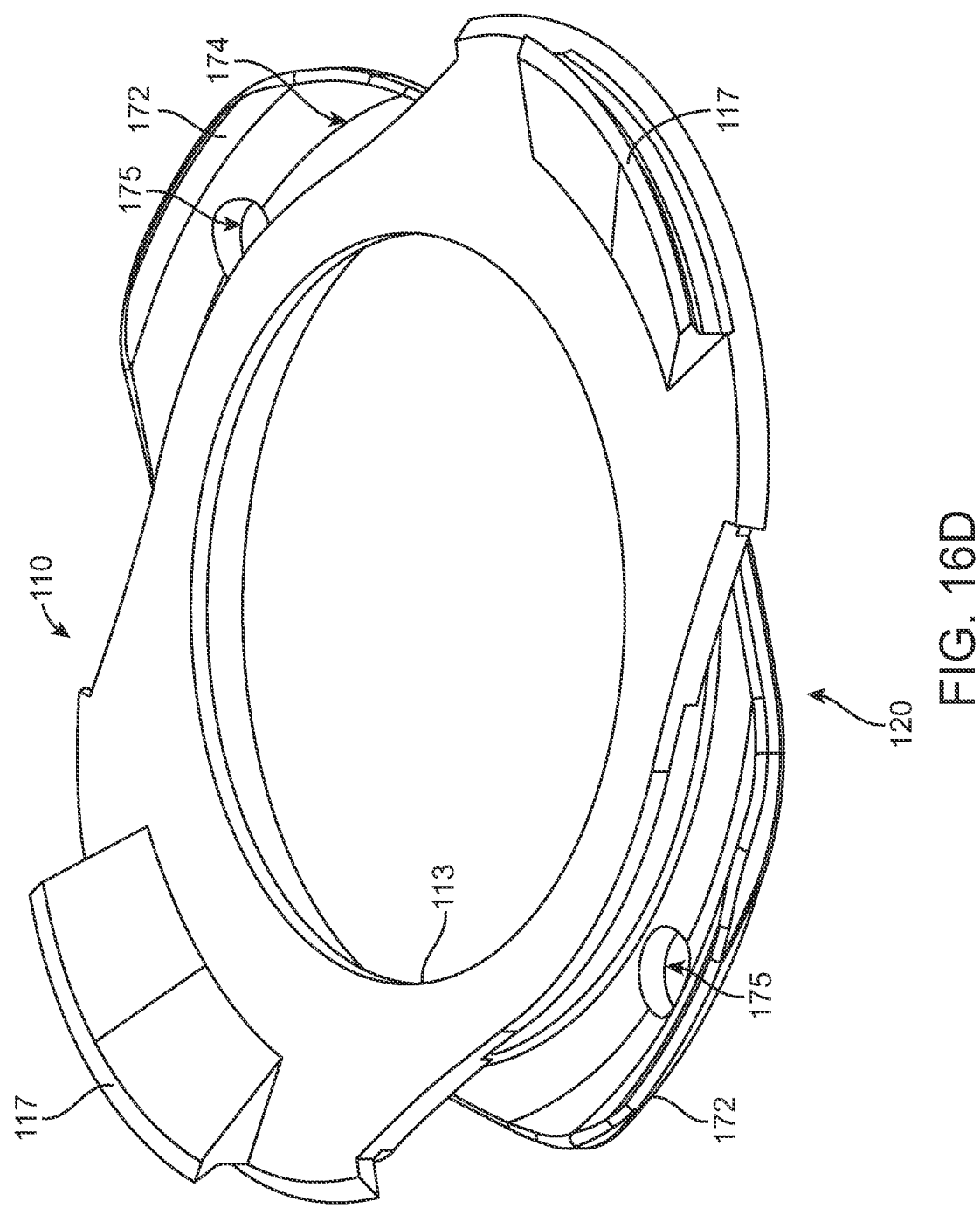

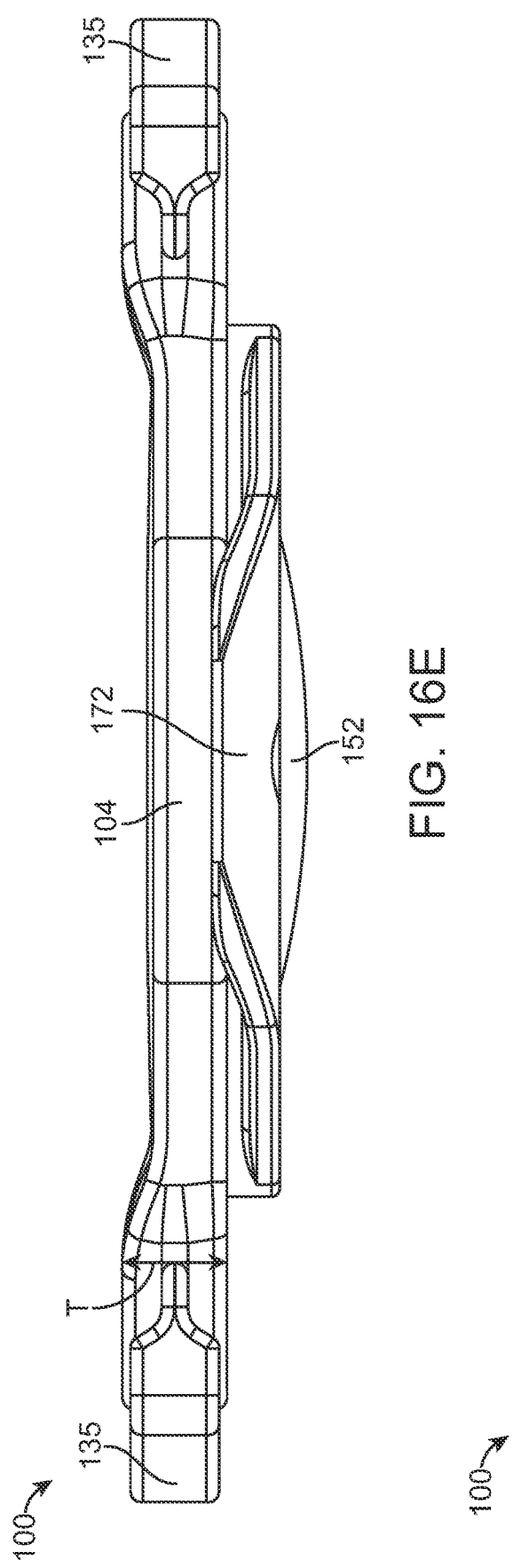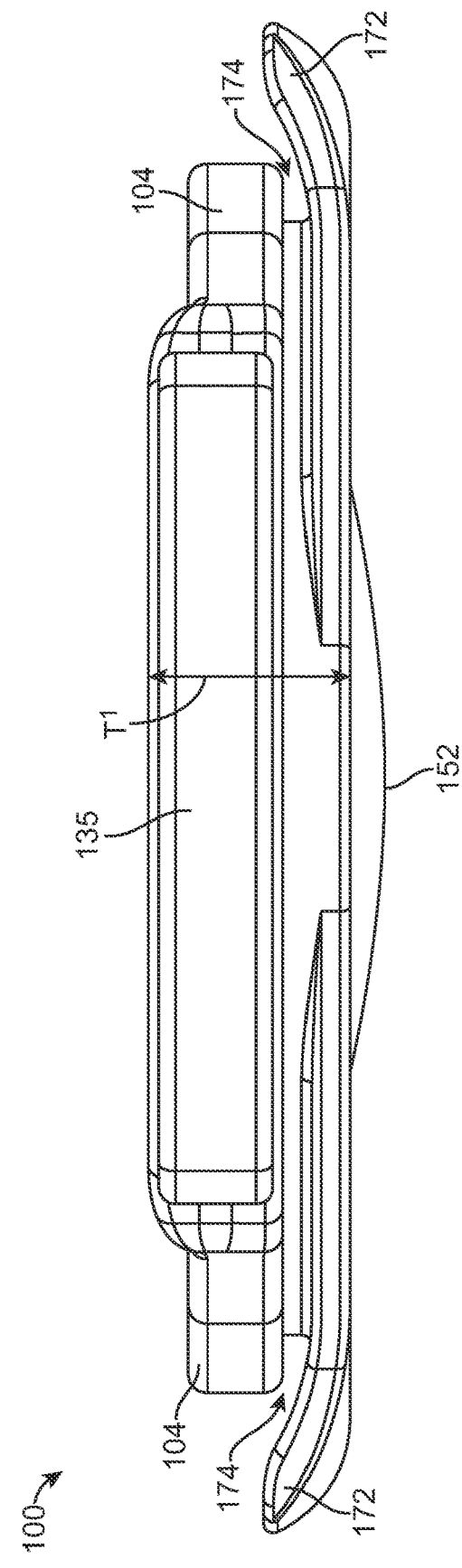

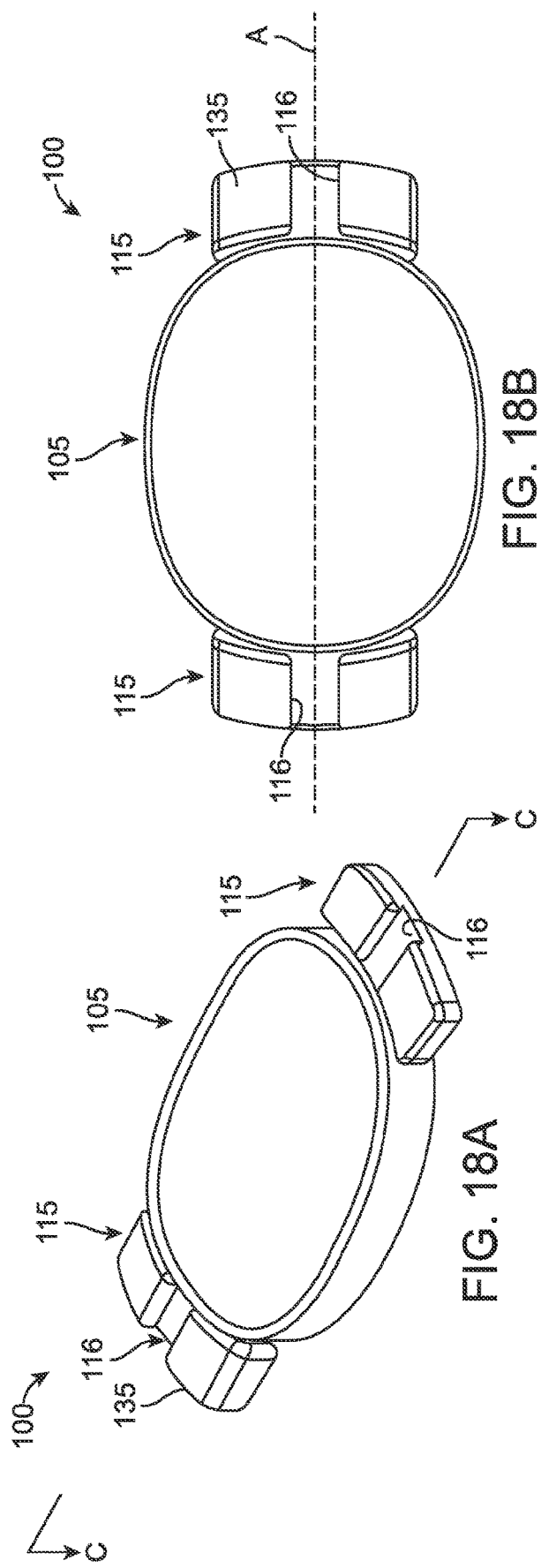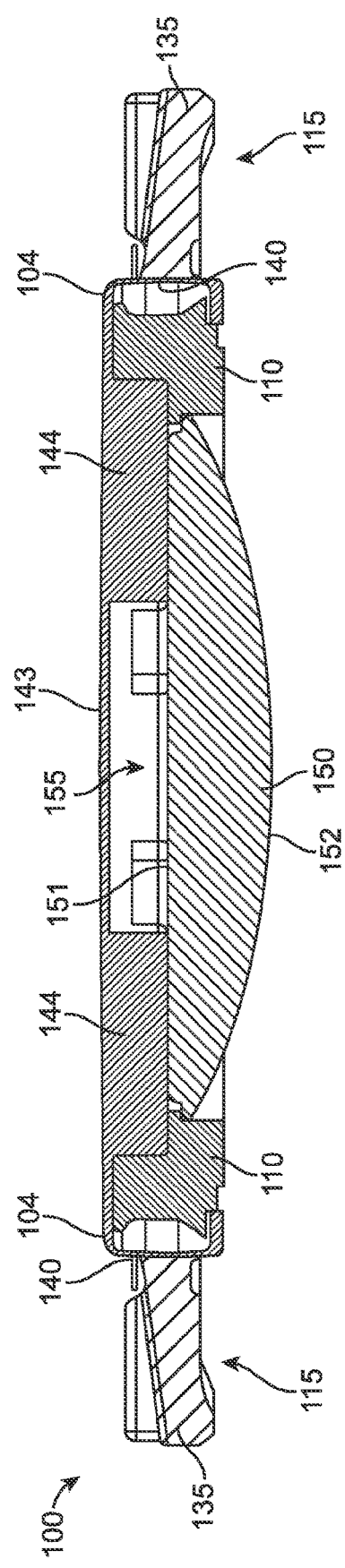

ACCOMMODATING INTRAOCULAR LENS AND METHODS OF IMPLANTATION

CROSS-REFERENCE TO RELATED APPLICATIONS

The present application is a 371 U.S. National Phase Application of PCT Application Ser. No. PCT/US2017/58810, filed on Oct. 27, 2017, which claims the benefit of priority to U.S. Provisional Application Ser. No. 62/414,571, filed Oct. 28, 2016, the entire contents of which are hereby incorporated by reference herein in their entireties.

BACKGROUND

The present disclosure relates generally to the field of ophthalmics, more particularly to ophthalmic devices, including intraocular lenses (IOLs) such as accommodating intraocular lenses.

A healthy, young human eye can focus an object in far or near distance, as required. The capability of the eye to change back and forth from near vision to far vision is called accommodation. Accommodation occurs when the ciliary muscle contracts to thereby release the resting zonular tension on the equatorial region of the capsular bag. The release of zonular tension allows the inherent elasticity of the lens to alter to a more globular or spherical shape, with increased surface curvatures of both the anterior and posterior lenticular surfaces.

The human lens can be afflicted with one or more disorders that degrade its functioning in the vision system. A common lens disorder is a cataract which is the opacification of the normally clear, natural crystalline lens matrix. The opacification can result from the aging process but can also be caused by heredity or diabetes. In a cataract procedure, the patient's opaque crystalline lens is replaced with a clear lens implant or IOL.

In conventional extracapsular cataract surgery, the crystalline lens matrix is removed leaving intact the thin walls of the anterior and posterior capsules together with zonular ligament connections to the ciliary body and ciliary muscles. The crystalline lens core is removed by phacoemulsification through a curvilinear capsulorhexis i.e., the removal of an anterior portion of the capsular sac.

After a healing period of a few days to weeks, the capsular sac effectively shrink-wraps around the IOL due to the collapse of the walls of the capsular sac and subsequent fibrosis. Cataract surgery as practiced today causes the irretrievable loss of most of the eye's natural structures that provide accommodation. The crystalline lens matrix is completely lost and the integrity of the capsular sac is reduced by the capsulorhexis. The "shrink-wrap" of the capsular sac around the IOL can damage the zonule complex, and thereafter the ciliary muscles may atrophy. Thus, conventional IOL's, even those that profess to be accommodative, may be unable to provide sufficient axial lens spatial displacement along the optical axis or lens shape change to provide an adequate amount of accommodation for near vision.

Beyond IOL placement following cataract surgery, it is known that an artificial, "piggy back," lens can be utilized to correct the refractive error of a healthy crystalline lens. Additionally, this "piggy back" approach can be beneficial to a patient who has previously undergone cataract surgery, has an artificial lens in place, but needs additional refractive correction. These "piggyback" IOLs can be placed anterior to the previously implanted IOL or natural lens to improve the refractive results of cataract surgery in the case of pseudophakes or to change the refractive status of the eye in the case of phakic eyes, usually to correct high myopia. Generally, these lenses are implanted in the sulcus or angle and are non-accommodating.

SUMMARY

In an aspect, described is an accommodating intraocular lens device for treatment of an eye including a lens body having an accommodating membrane with a perimeter region and a surface configured to outwardly bow. The lens body has an annular element is coupled to the perimeter of the accommodating membrane. The annular element has a shape deformation membrane extending along an arc of the annular element. The shape deformation membrane is configured to undergo displacement relative to the perimeter region of the accommodating membrane. The lens body has a static element having a perimeter region coupled to the annular element. The static element is positioned opposite the accommodating membrane. The lens body has a fixed volume of optical fluid. An inner surface of the accommodating membrane, an inner surface of the shape deformation membrane and an inner surface of the static element collectively form a sealed chamber of the lens body filled by the fixed volume of optical fluid. An annular, internal support is sealed with the perimeter region of the accommodating membrane on a first side and sealed with the perimeter region of the static element on a second side. A stabilization system includes a haptic having an internal portion and a terminal end. The internal portion of the haptic is coupled to the annular internal support near the perimeter region of the lens body. A force translation arm is included that has a first end operatively coupled to the shape deformation membrane of the lens body and a free end available and configured to engage a ciliary structure of the eye when the lens device is implanted in the eye such that an optical axis of the lens body is substantially aligned with a visual axis of the eye. The force translation arm is movable relative to the lens body to cause inward movement of the shape deformation membrane.

Inward movement of the force translation arm can cause the inward movement of the shape deformation membrane and a deformation of the sealed chamber. Inward movement of the shape deformation membrane can cause the optical fluid in the sealed chamber to press against the inner surface of the accommodating membrane. The internal support can mechanically isolate optical components of the lens body from distortion during movement of the force translation arm relative to the lens body and from distortion due to stresses on the stabilization system. An outer perimeter of the internal support can include a concave geometry to avoid contact with the inner surface of the shape deformation membrane during inward movement of the shape deformation membrane. An outer perimeter of the internal support can include features having a wedge shape that tapers toward a central aperture of the annular, internal support. The internal support can form a partition within the sealed chamber dividing the sealed chamber into a deformable region and a central region. The internal support can include a channel extending through the internal support providing fluid communication between the deformable region and the central region of the sealed chamber. The deformable region can be located outside an optic zone of the lens body or inside an optic zone of the lens body. Inward movement of the shape deformation membrane can deform the deformable region. Inward movement of the shape deformation membrane can compress the sealed chamber. The optical fluid in the sealed chamber can be non-compressible and press against the inner surface of the accommodating membrane to cause the outward bowing of the accommodating membrane upon inward movement of the shape deformation member. The shape deformation membrane can move a distance of between about 50 µm to about 100 µm. Movement of the shape deformation membrane can cause a change in power of the lens body by at least ±3 diopters. A force applied to move the shape deformation membrane can be between about 0.1 gf to about 1 gf.

The terminal end of the haptic can further include a biting element to improve fixation of the haptic within the eye. The biting element can include a grooved edge and/or a hole. The terminal end of the haptic can extend over the force translation arm. The terminal end of the haptic can be positioned on a different plane than the force translation arm. The terminal end of the haptic can extend on a plane anterior to the force translation arm and can be configured to be positioned within a ciliary sulcus or the capsular bag of the eye. The haptic can be flexible, foldable or formed of a shape memory material. The lens body can include a deformable portion that is located outside an optic zone. The deformable portion can be a region of the shape deformation membrane. The lens body can include a deformable portion that is located inside an optic zone. The deformable portion can be a region of the shape deformation membrane. The shape deformation membrane can be annular. The outward bowing of the shape changing membrane can be manually adjustable. The static element can be a static lens having an optical power. The static lens can be positioned posteriorly relative to the eye and the shape changing member can be positioned anteriorly relative to the eye. The shape changing membrane can have a constant thickness. The region of the shape changing membrane can be a reduced thickness region prone to give way upon increased internal pressure within the sealed chamber or upon application of pressure by the optical fluid against the inner surface of the shape changing membrane.

The optical fluid can include a non-compressible liquid or gel of high clarity and transmission in the visible spectrum. The optical fluid can be silicone oil or fluorosilicone oil. The force translation arm can have a length configured to extend between the shape deformation membrane of the lens body and the ciliary structure. The length can be adjustable during insertion of the device in the eye. The adjustment can be mechanical or due to rotation of the device relative to the eye. A perimeter of the device can have a maximum cross-sectional thickness sized to extend between a posterior region of the iris and an anterior region of the capsular bag.

In an interrelated aspect, provided is an accommodating intraocular lens device for treatment of an eye having a lens body. The lens body including an accommodating membrane having a perimeter region and surface configured to outwardly bow. An annular element is coupled to the perimeter of the accommodating membrane. The annular element has a shape deformation membrane extending along an arc of the annular element. The shape deformation membrane is configured to undergo displacement relative to the perimeter region of the accommodating membrane. The device includes a static element having a perimeter region coupled to the annular element. The static element is positioned opposite the accommodating membrane. The device includes a fixed volume of optical fluid. An inner surface of the accommodating membrane, an inner surface of the shape deformation membrane and an inner surface of the static element collectively form a sealed chamber of the lens body filled by the fixed volume of optical fluid. The device includes an annular internal support sealed with the perimeter region of the accommodating membrane on a first side and sealed with the perimeter region of the static element on a second side. The device includes a stabilization system includes an annular ring structure coupled to the annular internal support and a flange extending radially outward from a posterior region of the lens body. The device includes a force translation arm having a first end operatively coupled to the shape deformation membrane of the lens body and a free end available and configured to engage a ciliary structure of the eye when the lens device is implanted in the eye such that an optical axis of the lens body is substantially aligned with a visual axis of the eye. The force translation arm is movable relative to the lens body to cause inward movement of the shape deformation membrane.

Inward movement of the force translation arm can cause the inward movement of the shape deformation membrane causing a deformation of the sealed chamber. Inward movement of the shape deformation membrane can cause the optical fluid in the sealed chamber to press against the inner surface of the accommodating membrane. The internal support can mechanically isolate optical components of the lens body from distortion during movement of the force translation arm relative to the lens body and from distortion due to stresses on the stabilization system. An outer perimeter of the internal support can include a concave geometry to avoid contact with the inner surface of the shape deformation membrane during inward movement of the shape deformation membrane. An outer perimeter of the internal support can include features having a wedge shape that tapers toward a central aperture of the annular, internal support. The internal support can form a partition within the sealed chamber dividing the sealed chamber into a deformable region and a central region. The internal support can include a channel extending through the internal support providing fluid communication between the deformable region and the central region of the sealed chamber. The deformable region can be located outside an optic zone of the lens body. The deformable region can be located inside an optic zone of the lens body. Inward movement of the shape deformation membrane can deform the deformable region. Inward movement of the shape deformation membrane can compress the sealed chamber. The optical fluid in the sealed chamber can be non-compressible and press against the inner surface of the accommodating membrane to cause the outward bowing of the accommodating membrane upon inward movement of the shape deformation member. The shape deformation membrane can move a distance between about 50 µm to about 100 µm. Movement of the shape deformation membrane can cause a change in power of the lens body by at least ±3 diopters. A force applied to move the shape deformation membrane can be between about 0.1 gf to about 1 gf.

The flange extending radially outward can be positioned a distance away from the force translation arm. The flange can be positioned in a posterior position relative to the lens body and to the force translation arm. The anterior surface of the flange may also be on the same plane as the force translation arm. The more anterior the flange, the greater it will pull the lens in a posterior direction. The force translation arm can include first and second force translation arms positioned opposite each other. The flange can include first and second flanges positioned opposite each other. The first and second flanges can be positioned between the first and second force translation arms. The stabilization system can further include a groove located near the annular ring structure. The groove can be formed between a posterior-facing surface of the annular element and an anterior-facing surface of the flange. The groove can be sized to receive a capsular bag edge formed by a capsulorhexis in the capsular bag. The flange can include an outer elevation bending toward an anterior direction. The flange can further include an interruption configured to provide access to the capsular bag. The interruption can be an aperture extending through the flange or an indentation in an outer perimeter of the flange.

The lens body can include a deformable portion that is located outside an optic zone. The deformable portion can be a region of the shape deformation membrane. The lens body can include a deformable portion that is located inside an optic zone. The deformable portion can be a region of the shape deformation membrane. The shape deformation membrane can be annular. Outward bowing of the shape changing membrane can be manually adjustable after implantation of the device in the eye. The static element can be a static lens having an optical power. The static lens can be positioned posteriorly relative to the eye and the shape changing member can be positioned anteriorly relative to the eye. The shape changing membrane can have a constant thickness. The region of the shape changing membrane can be a reduced thickness region prone to give way upon increased internal pressure within the sealed chamber or upon application of pressure by the optical fluid against the inner surface of the shape changing membrane. The optical fluid can include a non-compressible liquid or gel of high clarity and transmission in the visible spectrum. The optical fluid can be silicone oil or fluorosilicone oil. The force translation arm can have a length configured to extend between the shape deformation membrane of the lens body and the ciliary structure. The length can be adjustable during insertion of the device in the eye. The adjustment can be mechanical or due to rotation of the device relative to the eye. A perimeter of the device can have a maximum cross-sectional thickness sized to extend between a posterior region of the iris and an anterior region of the capsular bag. Asymmetric inward movement of the force translation arm relative to the lens body can achieve a spherical outward bowing of the surface of the accommodating membrane. The device can include a single first translation arm or can further include a second force translation arm. The first and second force translation arms can be positioned opposite to one another and symmetrically relative to the lens body.

In an interrelated aspect, described is a method of implanting an accommodating intraocular lens (AIOL) device for treatment of an eye. The method includes forming a capsulorhexis; and implanting an AIOL device.

The AIOL device can include a lens body. The lens body can include an accommodating membrane having a perimeter region and surface configured to outwardly bow. The lens body can include an annular element coupled to the perimeter of the accommodating membrane. The annular element has a shape deformation membrane extending along an arc of the annular element. The shape deformation membrane is configured to undergo displacement relative to the perimeter region of the accommodating membrane. The lens body can include a static element having a perimeter region coupled to the annular element. The static element is positioned opposite the accommodating membrane. The lens body can include a fixed volume of optical fluid. An inner surface of the accommodating membrane, an inner surface of the shape deformation membrane and an inner surface of the static element can collectively form a sealed chamber of the lens body filled by the fixed volume of optical fluid. The device can include an annular internal support sealed with the perimeter region of the accommodating membrane on a first side and sealed with the perimeter region of the static element on a second side. The device can include a stabilization system. The device can include a force translation arm having a first end operatively coupled to the shape deformation membrane of the lens body and a free end available and configured to engage a ciliary structure of the eye when the lens device is implanted in the eye such that an optical axis of the lens body is substantially aligned with a visual axis of the eye. The force translation arm is movable relative to the lens body to cause inward movement of the shape deformation membrane.

The stabilization system can include an annular ring structure coupled to the annular internal support and a flange extending radially outward from a posterior region of the lens body. The stabilization system can include stabilization haptics having an internal portion and a terminal end, the internal portion of the haptic coupled to the annular internal support near the perimeter region of the lens body. The device can include two, opposing force translation arms.

The method can further include positioning the stabilization haptics within the ciliary sulcus to urge the device posteriorly away from the iris of the eye. The method can further include positioning the stabilization haptics inside a capsular bag of the eye and implanting the force translation arms outside the capsular bag. The method can further include extending edges of the capsular bag formed by the capsulorhexis over an anterior surface of the stabilization haptics. An anterior face of the device can be pulled away from the iris of the eye by the edges of the capsular bag. The method can further include orienting the device upon implantation such that a posterior surface of the device is positioned posterior to the capsulorhexis and the force translation arms remain anterior to the capsulorhexis. Orienting the device can include orienting the opposing force translation arms horizontally in a medio-lateral manner relative to the eye to minimize shifting following implantation. Implanting the device can include rotating the device around its optical axis. The method can further include rotating the device around its optical axis, but maintaining a gap between an outermost portion of the force translation arm and the ciliary structure. The gap can have a size of about 0.1 mm. The method can further include rotating the device around its optical axis until an outermost portion of the force translation arm wedges into engagement with the ciliary structure. The ciliary structure can be the ciliary muscle of the eye. Rotating the device can adjust a fit of the force translation arm relative to the ciliary muscle. The device can be implanted by inserting the device through a corneal incision in the eye. The method can further include rolling or folding the device into an applicator and injected through the corneal incision. A tip of the applicator can be about 2.5 mm in cross-sectional diameter. The device can be implanted by inserting the device through a scleral tunnel or a scleral incision. The capsulorhexis can be oval shaped. The capsulorhexis can be about 6 mm×7 mm. The method can further include measuring a diameter of the ciliary body of the eye prior to implanting the AIOL device. The diameter can be measured by ultrasound biomicroscopy (UBM), optical coherence tomography (OCT), or other medical imaging techniques.

In some variations, one or more of the following can optionally be included in any feasible combination in the above methods, apparatus, devices, and systems. More details of the devices, systems, and methods are set forth in the accompanying drawings and the description below. Other features and advantages are apparent from the following description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIG. 2C is a first side view of the AIOL of FIG. 2B;

FIG. 2D is a second side view of the AIOL of FIG. 2B;

FIGS. 4A-4C illustrate an accommodating intraocular lens positioned within the eye relative to the iris and the capsular bag;

FIG. 16D is the internal support and stabilization system of the device of FIG. 16A;

FIGS. 16E-16F are side views of the device of FIG. 16A;

FIG. 18A illustrates a perspective view of an implementation of an accommodating intraocular lens device;

FIG. 18B is a top view of the device of FIG. 18A;

FIG. 18C is a cross-sectional view taken along line C-C of FIG. 18A;

It should be appreciated that the drawings herein are exemplary only and are not meant to be to scale.

DETAILED DESCRIPTION

The present disclosure relates generally to the field of ophthalmics, more particularly to ophthalmic devices, including intraocular lenses (IOLs) such as accommodating intraocular lenses (AIOLs). The dynamic nature of AIOLs allows for a large, continuous range of focusing power, just as in a young accommodative natural eye. The devices described herein can provide focusing power across the full accommodative range from distance to near by mechanically and functionally interacting with eye tissues typically used by a natural lens such as the ciliary body, ciliary processes, and the zonules, to effect accommodation and disaccommodation. The forces generated by these tissues are functionally translated to the devices described herein causing a power change to more effectively accommodate. The devices described herein are configured to be adjusted for size and fit prior to, during, as well as at any time after implantation. The devices described herein can be implanted in the eye to replace a diseased, natural lens. It should be appreciated, however, the devices can also be implanted as a supplement of a natural lens (phakic patient) or an intraocular lens previously implanted within a patient's capsular bag (pseudophakic patient).

Figure 1A:
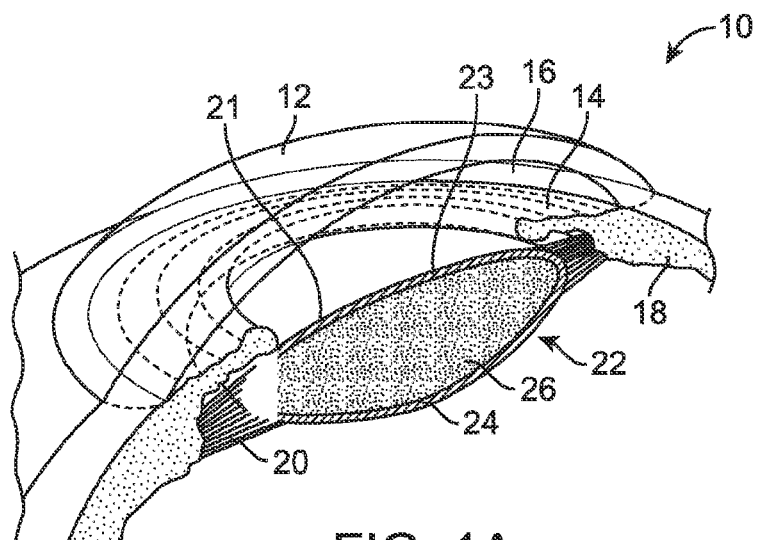
FIG. 1A is a perspective cut-away view of an eye with an opacified lens capsule.
Figure 1B:
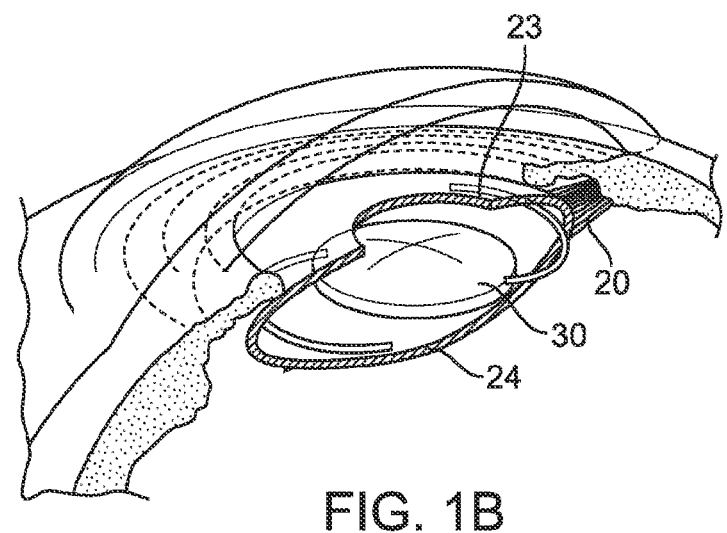
FIG. 1B is a perspective cut-away view of the eye of FIG. 1A with a curvilinear capsulorhexis and the crystalline lens matrix removed with the implantation of a traditional 3-piece IOL.
Figure 1C:
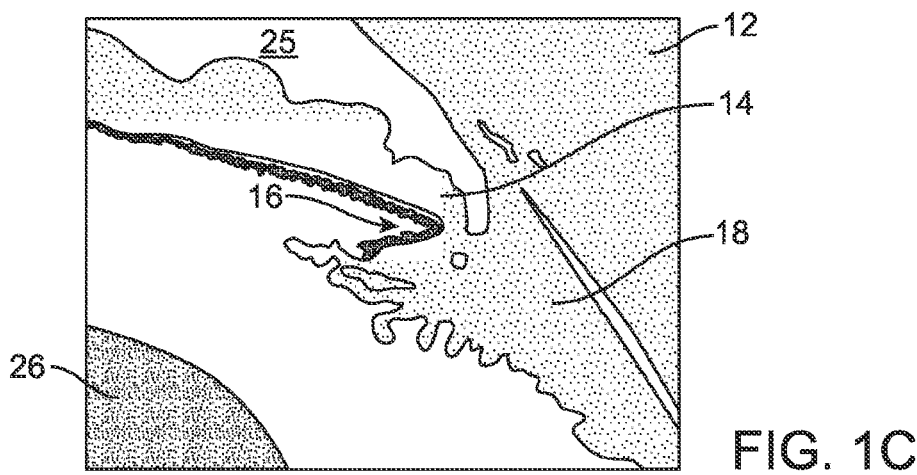
FIG. 1C is a cross-sectional view of an anterior angle of an eye.

With reference to FIGS. 1A and 1C, the human eye 10 includes a cornea 12, iris 14, sulcus 16, ciliary muscle 18, zonules 20, a lens 21 contained within a capsular bag 22. Accommodation occurs when the ciliary muscle 18 contracts to thereby release the resting zonular tension on the equatorial region of the capsular bag 22. The release of zonular tension allows the inherent elasticity of the lens 21 to alter to a more globular or spherical shape, with increased surface curvatures of both the anterior lenticular surface 23 and posterior lenticular surface 24. In addition, the human lens can be afflicted with one or more disorders that degrade its functioning in the vision system. A common lens disorder is a cataract which consists of the opacification of the normally clear, natural crystalline lens matrix 26. The opacification can result from the aging process but can also be caused by heredity, diabetes, or trauma. FIG. 1A shows a lens capsule comprising a capsular bag 22 with an opacified, crystalline lens nucleus 26.

In a cataract procedure, the patient's opaque crystalline lens is replaced with a clear lens implant or IOL 30. In conventional extracapsular cataract surgery as depicted in FIG. 1B, the crystalline lens matrix 26 is removed leaving intact the thin walls of the anterior and posterior capsules together with zonular ligament connections to the ciliary body and ciliary muscles 18. The crystalline lens core is removed by phacoemulsification through a curvilinear capsulorhexis as illustrated in FIG. 1B, i.e., the removal of an anterior portion 23 of the capsular sac. FIG. 1B depicts a conventional 3-piece IOL 30 just after implantation in the capsular bag 22. The capsular bag 22 after a healing period of a few days to weeks can effectively shrink-wrap around a conventional 3-piece IOL 30 due to the collapse of the walls of the sac 22 and subsequent fibrosis. Cataract surgery as practiced today causes the irretrievable loss of most of the eye's natural structures that provide accommodation. The crystalline lens matrix 26 is completely lost and the integrity of the capsular sac 22 is reduced by the capsulorhexis. The fibrosis of the capsular bag limits the dynamic movement of a lens placed in that bag. Thus, conventional IOL's, even those that profess to be accommodative, may be unable to provide sufficient axial lens spatial displacement along the optical axis or lens shape change to provide an adequate amount of accommodation for near vision.

It is known to implant a combination of lenses to address refraction errors in the existing lens in the case of phakic IOLs or improve the refractive results of standard IOL after cataract surgery in the case of pseudophakic patients. These "piggyback" IOLs can be placed anterior to the previously implanted IOL or natural lens to improve the refractive results of cataract surgery in the case of pseudophakes or to change the refractive status of the eye in the case of phakic eyes, usually to correct high myopia. Generally, these lenses are implanted in the ciliary sulcus and are non-accommodating. As best shown in FIG. 1C, the ciliary sulcus 16 is the space between the posterior surface of the base of the iris 14 and the anterior surface of the ciliary body.

Accommodating IOLs are also beneficial for patients not suffering from cataracts, but who wish to reduce their dependency on glasses and contacts to correct their myopia, hyperopia and presbyopia. Intraocular lenses used to correct large errors in myopic, hyperopic, and astigmatic eye are called "phakic intraocular lenses" and are implanted without removing the crystalline lens. In some cases, aphakic IOLs (not phakic IOLs) are implanted via lens extraction and replacement surgery even if no cataract exists. During this surgery, the crystalline lens is extracted and an IOL replaces it in a process that is very similar to cataract surgery. Refractive lens exchange, like cataract surgery, involves lens replacement, requires making a small incision in the eye for lens insertion, use of local anesthesia and lasts approximately 30 minutes. The accommodating IOLs described herein can be used in patients for refractive lens exchange.

Described herein are accommodating IOLs ("AIOLs") that can achieve the desired optical power change, for example in the range of 1 diopter (1 D) to 3 D up to about 5 D or 6 D. As will be described in more detail below, the devices described herein can include an accommodative mechanism including one or more force translation arms configured to be positioned in the eye such that they harness movements of one or more ciliary structures and translate the movements into functional forces to drive shape change of the lens body for accommodation and disaccommodation in a manner independent of capsular bag movements. The devices described herein can further include a stabilization system separate from the accommodative mechanism that is configured to be positioned, for example, within the capsular bag. The devices described herein obviate known issues that tend to occur due to capsular fibrosis described above. It should be appreciated that the devices described herein can be configured to harness movements of one or combinations of ciliary structures including, but not limited to, the ciliary muscle, the ciliary body, ciliary processes, and zonules. For the sake of brevity, the term "ciliary structure" may be used herein to refer to any of the one or more ciliary structures for which movements can be harnessed by the force translation arms to effect accommodation of the lens body.

The devices described herein can be implanted in the eye to replace a diseased, natural lens. In some implementations, the devices described herein can be implanted as aphakic IOLs via refractive lens exchange procedures. The intraocular lenses described herein can also be implanted as a supplement of a natural lens (phakic patient) or an intraocular lens previously implanted within a patient's capsular bag (pseudophakic patient). The lenses described herein can be used in combination with intraocular lenses described in U.S. Patent Publication Nos. 2009/0234449, 2009/0292355, 2012/0253459, and PCT Publication No. WO 2015/148673, which are each incorporated by reference herein in their entirety. As such, the lenses described herein can be used independently or as so-called "piggyback" lenses. Piggyback lenses can be used to correct residual refractive errors in phakic or pseudophakic eyes. The primary IOL used to replace the natural lens is generally thicker and usually has a power that can be in the range of ±10 D to ±25 D. The thicker, larger power lenses generally do not accommodate. In contrast, the supplemental lens need not provide significant optical power to the system. The supplemental lens can be relatively thin compared to the primary IOL and can undergo more accommodation. Shape change and movement of the thinner lens is generally more easily accomplished relative to a thick primary lens. The AIOLs described herein can be used independently and need not be used in combination as piggyback lenses with the natural lens or an implanted IOL. One or more components of the AIOLs described herein can be configured to be positioned in the sulcus 16, against the ciliary processes, within the capsular bag 22 or a combination thereof.

Turning now to FIGS. 2A to 2F, the accommodating intraocular lens ("AIOL") 100 can include a lens body 105 and one or more force translation arms 115, each of which will be described in more detail below. As will be described in more detail below, the force translation arms 115 are configured to harness movements of one or more of the ciliary structures such that they are bi-directionally movable relative to the lens body 105 to effect accommodative shape change of the lens body 105. For example, and without limiting this disclosure to any particular theory or mode of operation, the ciliary muscle 18 is a substantially annular structure or sphincter. In natural circumstances, when the eye is viewing an object at a far distance, the ciliary muscle 18 within the ciliary body relaxes and the inside diameter of the ciliary muscle 18 gets larger. The ciliary processes pull on the zonules 20, which in turn pull on the lens capsule 22 around its equator. This causes a natural lens to flatten or to become less convex, which is called disaccommodation. During accommodation, the ciliary muscle 18 contracts and the inside diameter of the ring formed by the (ciliary ring diameter, CRD) ciliary muscle 18 gets smaller. The ciliary processes release the tension on the zonules 20 such that a natural lens will spring back into its natural, more convex shape and the eye can focus at near distances. This inward/anterior movement of the ciliary muscle 18 (or one or more ciliary structures) can be harnessed by the force translation arms 115 to cause a shape change in the lens body 105.

Figure 2A:
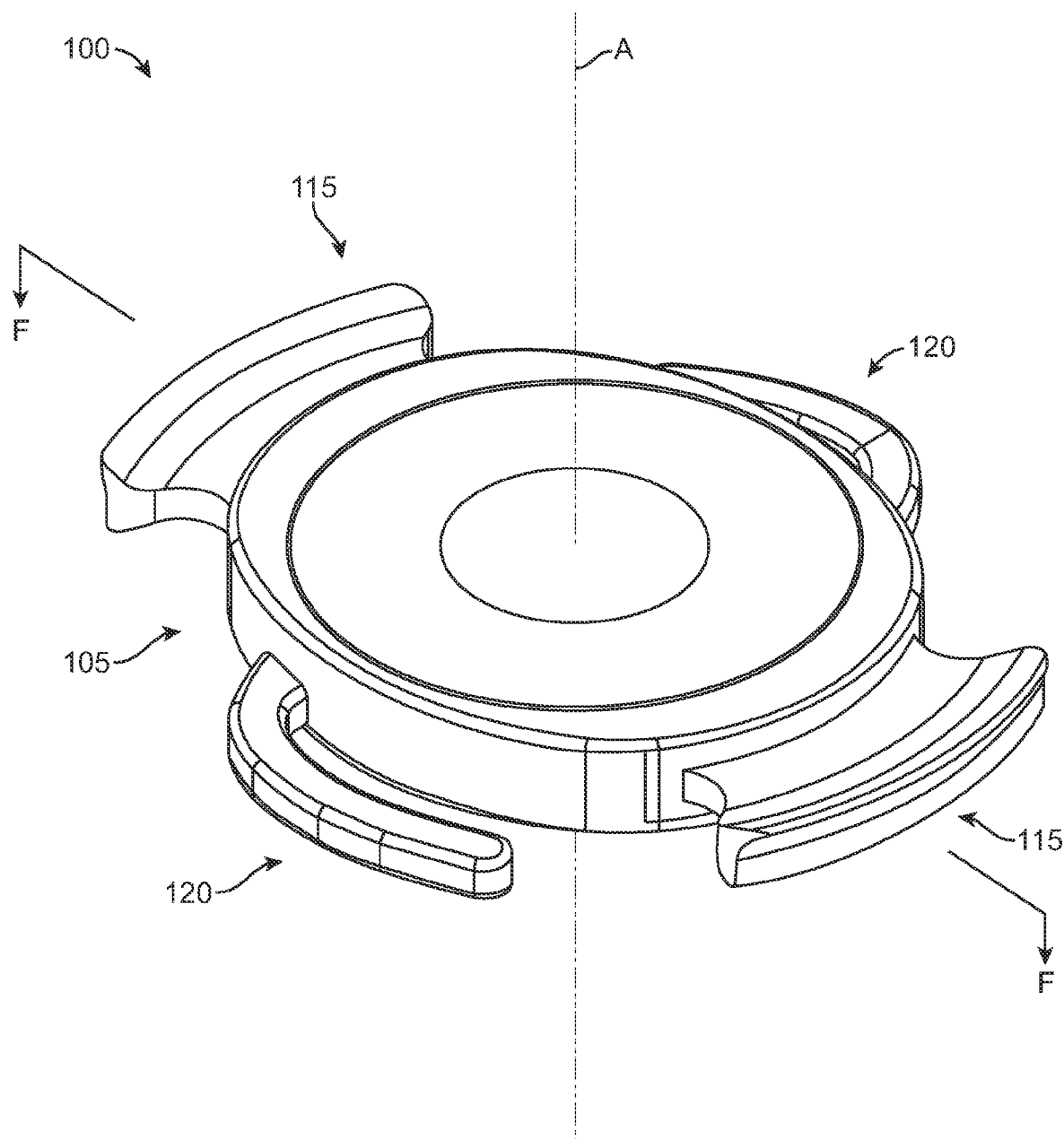
FIG. 2A is a perspective view of an implementation of an accommodating intraocular lens ("AIOL")
Figure 2B:
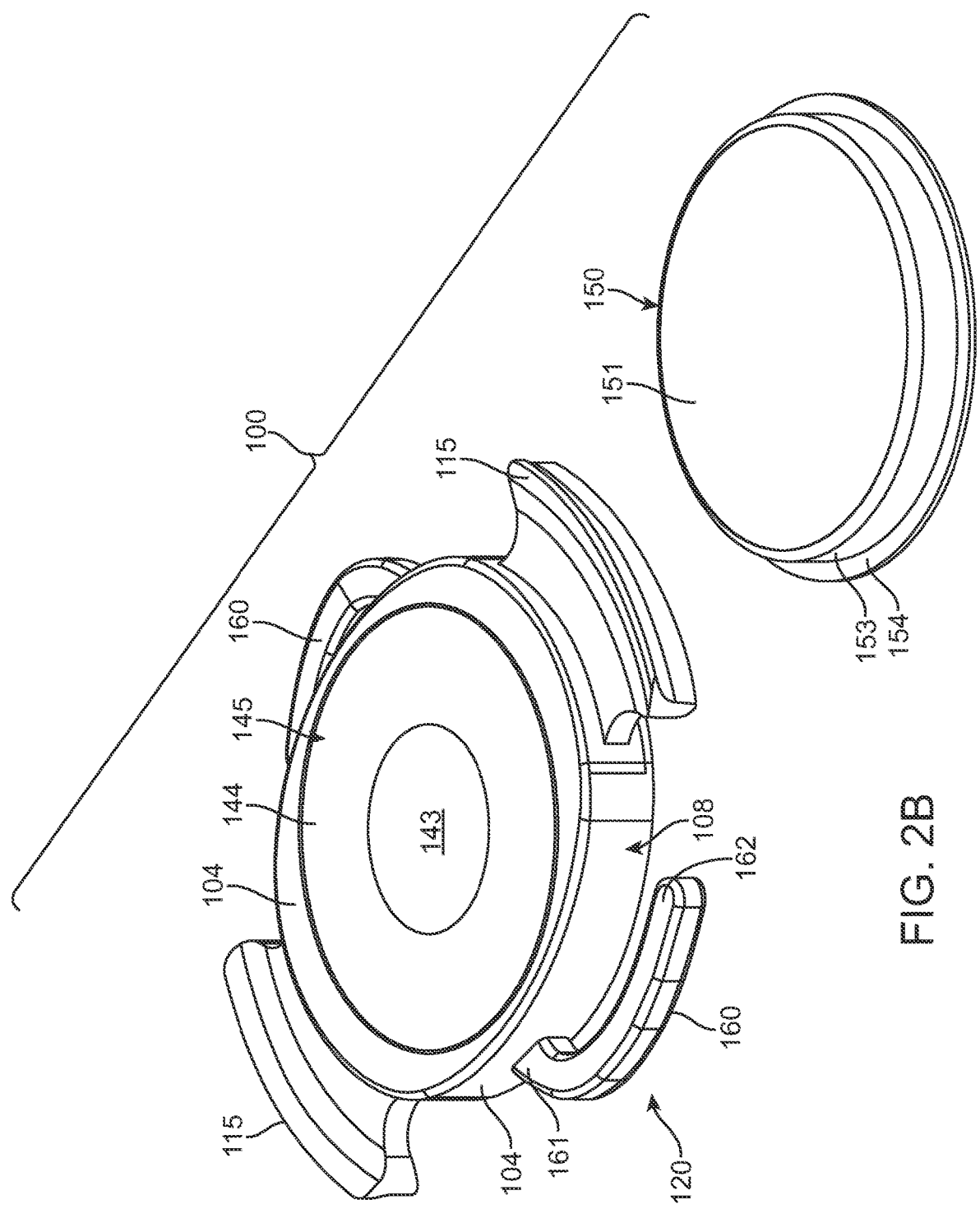
FIG. 2B is an exploded view of the AIOL of FIG. 2A.

Still with respect to FIGS. 2A to 2F, the lens body 105 can include a generally ring-shaped perimeter region or annular element 104, an anterior optic 145, a static element 150, and a fixed volume, sealed chamber 155 filled by a fixed volume of an optical fluid 156. The annular element 104 can include an anterior end region, a posterior end region 107, and an intervening equator region 108. The anterior end region of the annular element 104 can be coupled to the anterior optic 145 and the posterior end region of the annular element 104 can be coupled to the static element 150 such that the anterior optic 145 is positioned opposite the static element 150. FIGS. 3A-3B also illustrate the posterior end region 107 and the equator region 108 of annular element 104. The anterior optic 145 of the lens body 105 can include a central, dynamic membrane 143 surrounded by a perimeter region 144. The perimeter region 144 can be coupled to or integral with the annular element 104 of the lens body 105. The dynamic membrane 143 of the anterior optic 145 is configured to undergo a shape change whereas the perimeter region 144 can be configured to resist or not to undergo a shape change. The static element 150, which can be a static lens, may not undergo a shape change as well.

The terms "anterior" and "posterior" as used herein are used to denote a relative frame of reference, position, direction or orientation for understanding and clarity. Use of the terms is not intended to be limiting to the structure and/or implantation of the lens. For example, the orientation of the lens body 105 within the eye can vary such that the anterior optic 145 can be positioned anteriorly along the optical axis A of the AIOL 100 and the static element 150 positioned posteriorly along the optical axis A of the AIOL 100 relative to the eye anatomy. However, the anterior optic 145 can be positioned posteriorly and the static element 150 positioned anteriorly relative to the eye anatomy.

Figure 2E:
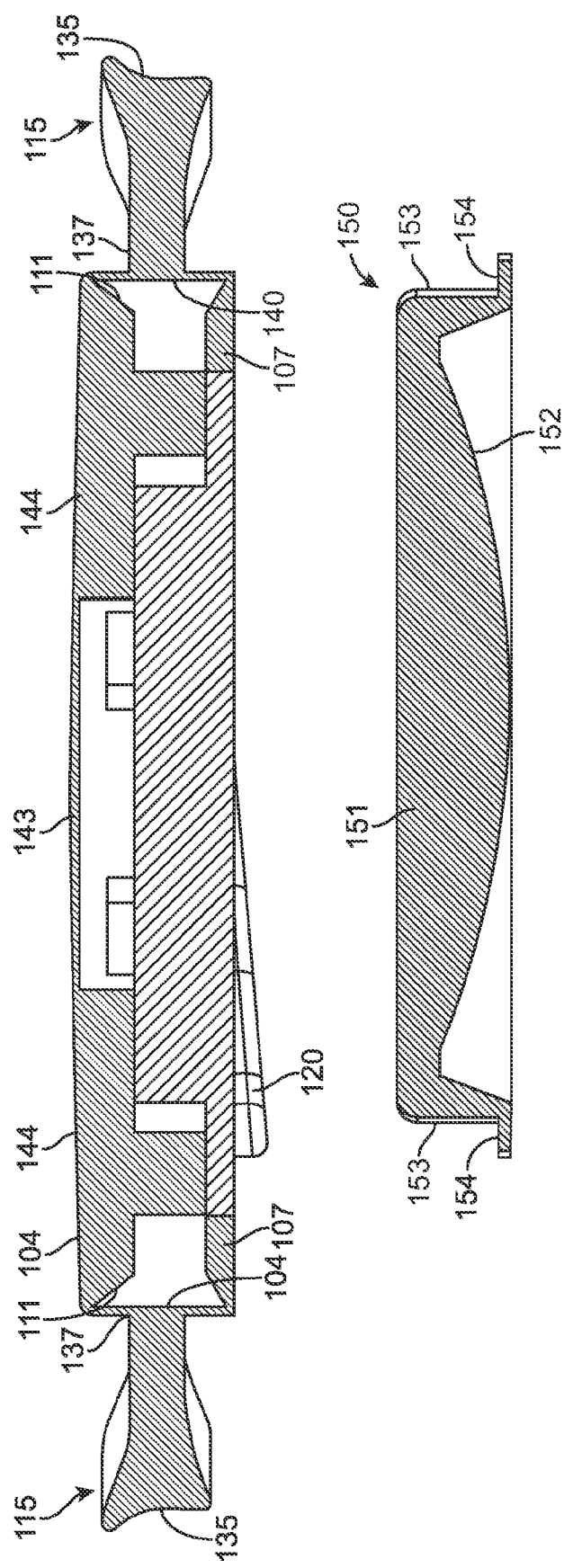
FIG. 2E is a cross-sectional view of the AIOL of FIG. 2D taken along line E-E.
Figure 2F:
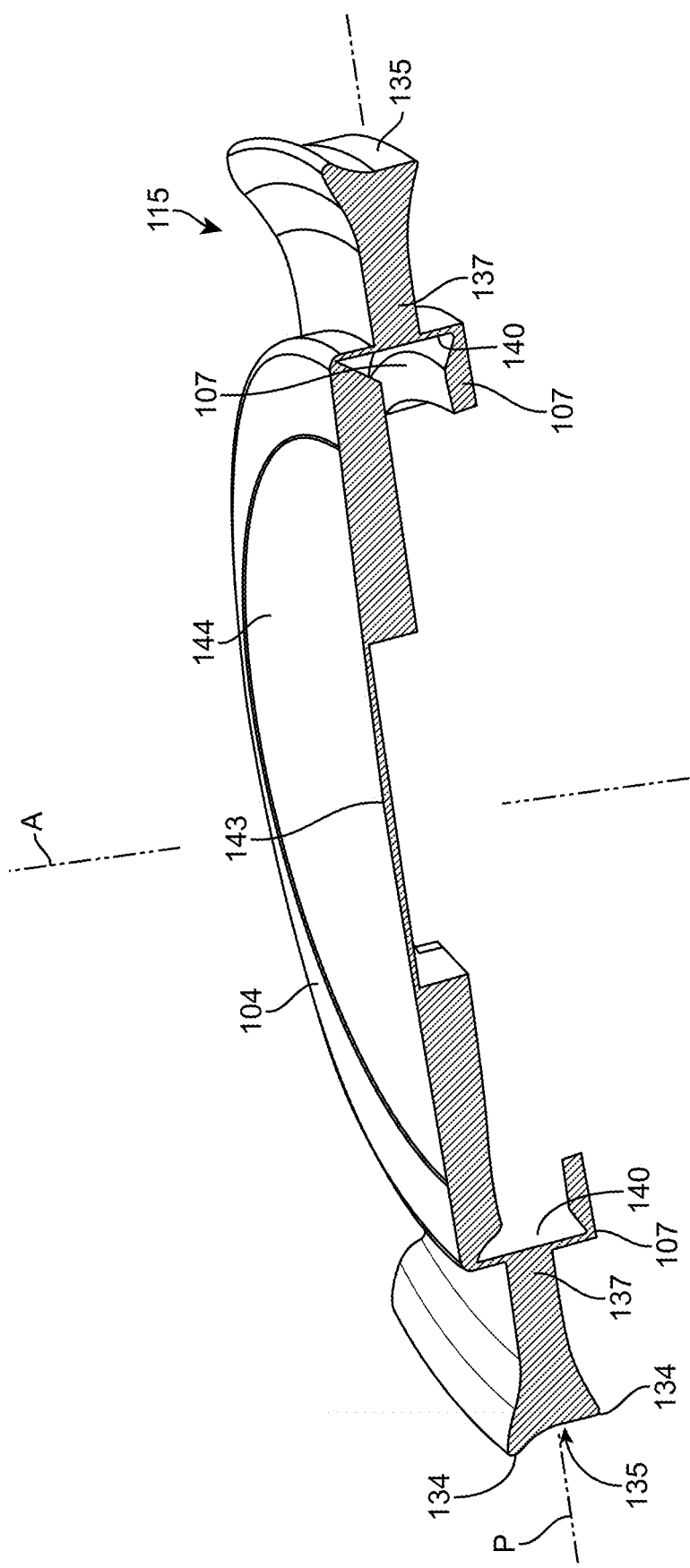
FIG. 2F is a cross-sectional view of the AIOL of FIG. 2A taken along line F-F.
Figure 3A:
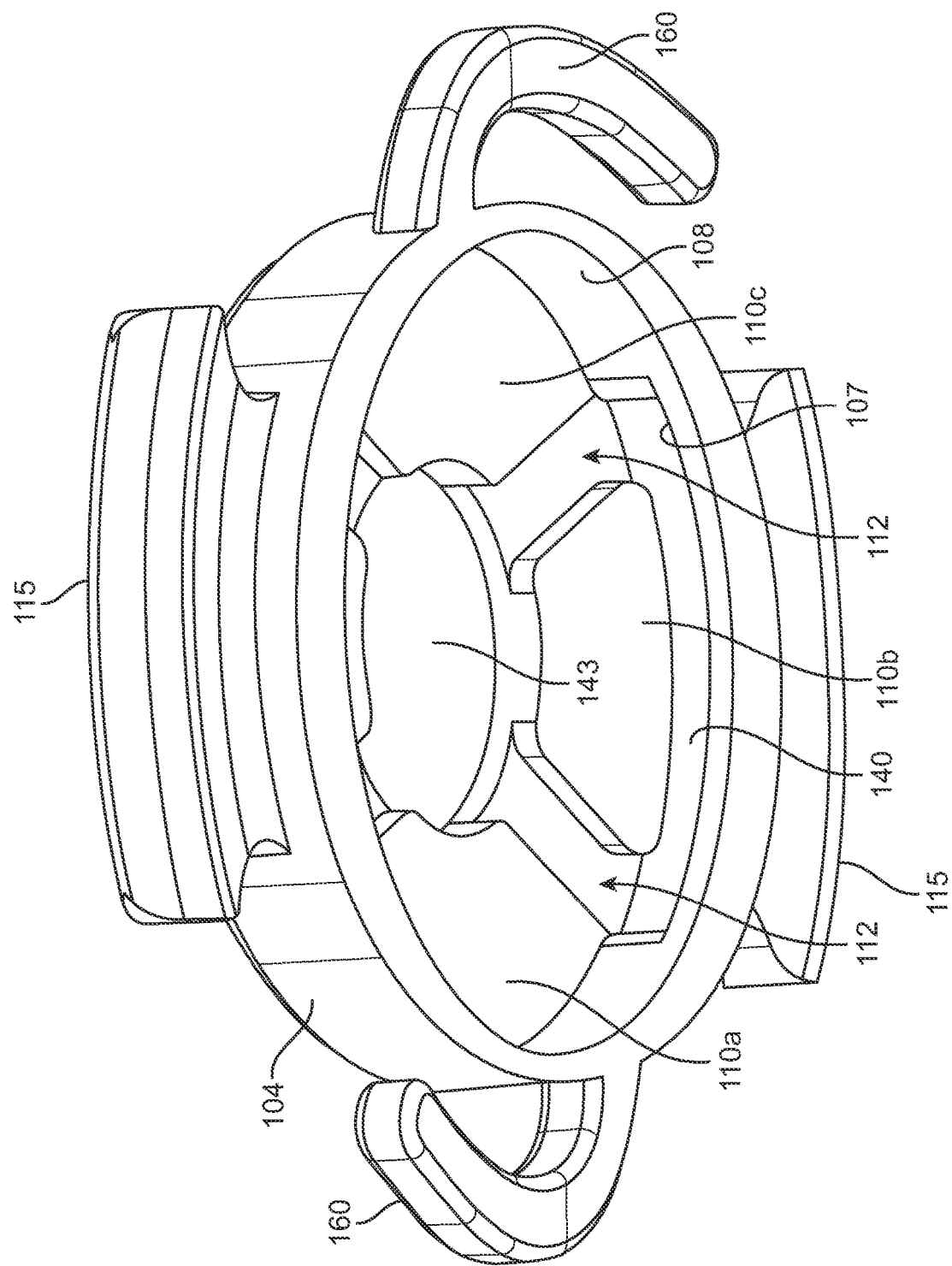
FIGS. 3A-3B are perspective views of an anterior lens portion of the AIOL of FIG. 2A.
Figure 3B:
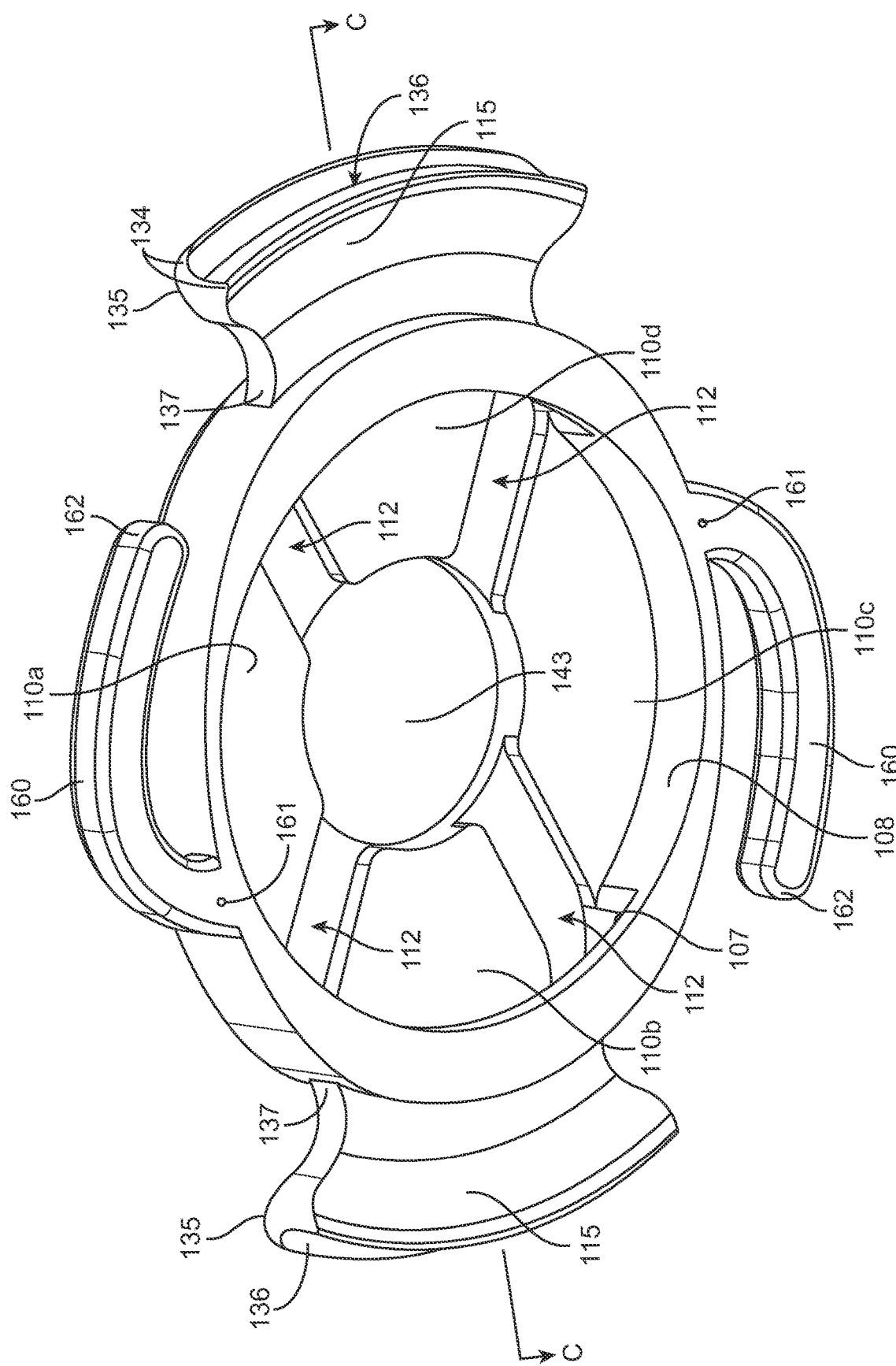

The equator region 108 of the annular element 104 of the lens body 105 can include at least one shape deformation membrane 140 (best shown in FIGS. 2E-2F). The inner surfaces of the anterior optic 145, the dynamic membrane 143, the perimeter region 144 of the anterior optic 145, the shape deformation membrane 140 and the static element 150 can collectively form the fixed volume, sealed chamber 155 filled by the fixed volume of optical fluid 156. The shape deformation membrane 140 is positioned adjacent the at least one force translation arm 115. As will be described in more detail below, movements of the force translation arms 115 cause movements of the shape deformation membrane 140 thereby deforming the optical fluid 156 and the sealed chamber 155 to cause a change in the shape of the dynamic membrane 143 of the lens body 105.

The anterior optic 145 can be a flexible optic formed of an optically clear, low modulus polymeric material such as silicone, polyurethane, or flexible acrylic. As mentioned above, the anterior optic 145 can include a perimeter region 144 surrounding a central, dynamic membrane 143 configured to outwardly bow. The dynamic membrane 143 can be positioned relative to the lens body 105 such that the optical axis A of the lens extends through the dynamic membrane 143. The perimeter region 144 of the anterior optic 145 surrounding the dynamic membrane 143 can be coupled to or integral with the annular element 104 of the lens body 105. In some implementations, the perimeter region 144 of the anterior optic 145 can be coupled to or integral with the anterior end region of the annular element 104 (see FIG. 3C). The anterior optic 145 can have a constant thickness such that it is a planar element. Alternatively, the anterior optic 145 can have a variable thickness. For example, the dynamic membrane 143 can have a reduced thickness compared to the perimeter region 144. The thinner cross-sectional thickness of the dynamic membrane 143 compared to the cross-sectional thickness of the perimeter region 144 can render it relatively more prone to give way upon application of a force on its inner surface. For example, upon an increased force applied against inner surfaces of the anterior optic 145 during deformation of the sealed chamber 155, the dynamic membrane 143 can bow outward along the optical axis A of the lens 100 while the perimeter region 144 maintains its shape. The dynamic membrane 143 can be configured to give way due to pressure applied by the optical fluid 156 within the sealed chamber 155 onto the internal surface of the anterior optic 145 causing an outward bowing of the outer face (e.g., anterior face). Outer perimeter region 144 of the anterior optic 145 can have a thickness greater than the inner dynamic membrane 143 of the optic 145 and can be more resistant to reshaping under such internal pressure applied by the optical fluid 156 in the sealed chamber 155. The outer perimeter region 144 of the anterior optic 145 can provide distance vision correction even when the inner dynamic membrane 143 is reshaped for near vision. The dynamic membrane 143 can have a substantially constant thickness. Alternatively, the dynamic membrane 143 can have a variable thickness. For example, the dynamic membrane 143 can have a linear gradient thickness, curved gradient thickness, 2, 3 or more thicknesses with a step including radiused or right angles. The dynamic membrane 143 can also include multiple materials, for example, materials configured to flex near a center of the dynamic membrane 143 and other materials configured to reinforce the optic zone and limit distortion. Thus, the dynamic membrane 143 of the anterior optic 145 can be formed of a material that is relatively more susceptible to outward bowing than the material of outer perimeter region 144. The various regions of the optic 145 can be injection or compression molded to provide a relatively seamless and uninterrupted outer face. The material of the regions can be generally consistent, though the dynamic membrane 143 can have different stiffness or elasticity that causes it to bow outward farther than the perimeter region 144.

The anterior optic 145 can be configured to have varied multifocal capabilities to provide the wearer of the AIOLs described herein with enhanced vision over a wider range of distances, for example, as described in U.S. Publication No. 2009/0234449, which is incorporated by reference herein in its entirety. The "optic zone" as used herein generally refers to a region of the lens body 105 that surrounds the optical axis A of the lens and is optically clear for vision. The "accommodating zone" as used herein generally refers to a region of the lens body 105 capable of undergoing shape change for focusing (e.g. the dynamic membrane 143). The optic zone is configured to have a corrective power although the entire optic zone may not have the same corrective power. For example, the dynamic membrane 143 and the perimeter region 144 of the anterior optic may each be positioned within the optic zone. The dynamic membrane 143 may have corrective power whereas the perimeter region 144 may not have corrective power. Or, for example, the diameter defined by the dynamic membrane 143 may have an optical power and the perimeter region 144 may have a power that is greater or lesser than that of the dynamic membrane 143. The dynamic membrane 143 can be equal to or smaller than the overall optical zone can create a multifocal lens. The accommodating zone of the lens body 105 can be equal to or smaller than the overall optic zone.

Figure 13A:
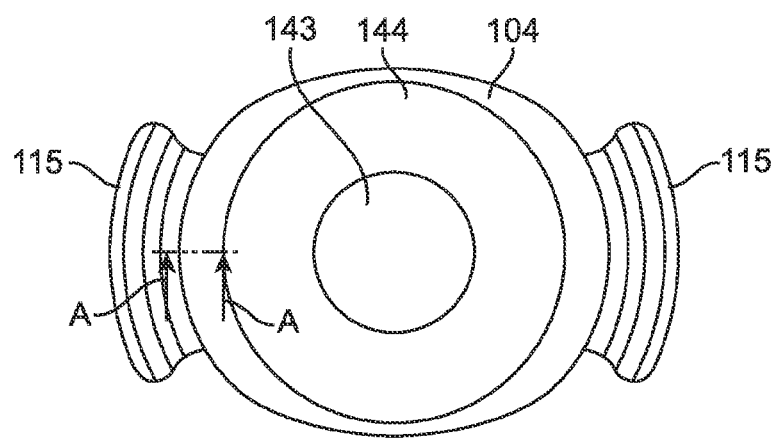
FIG. 13A illustrates a top view of an accommodating intraocular lens device.
Figure 13B:
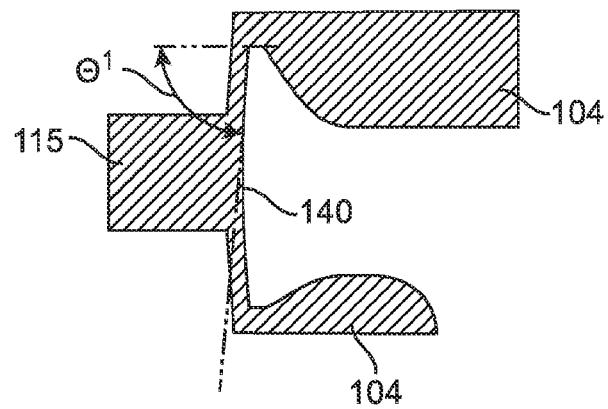
FIG. 13B illustrates a cross-sectional, partial view of the device of FIG. 13A taken along section A-A.
Figure 13C:
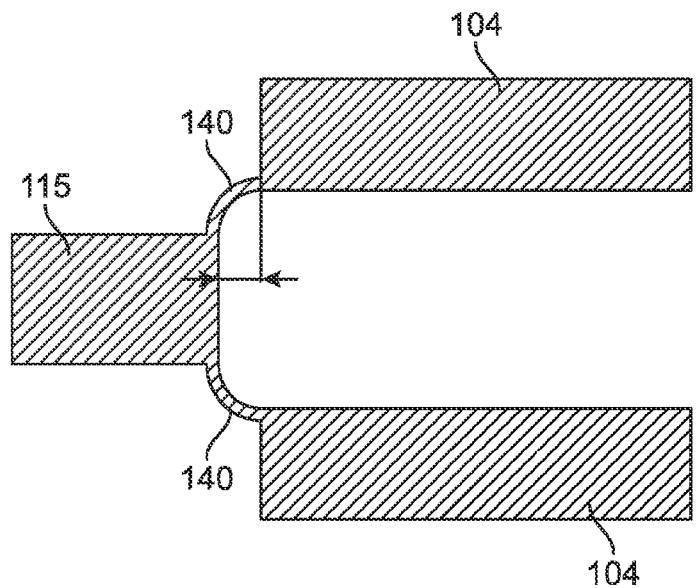
FIG. 13C illustrates another implementation of a cross-sectional, partial view of the device of FIG. 13A taken along section A-A.

As mentioned above and still with respect to FIGS. 2A-2F, the equator region 108 of the annular element 104 of the lens body 105 can include at least one shape deformation membrane 140. The shape deformation membrane 140 can extend along an arc length of the equator region 108 of the annular element 104 between the anterior end region of the annular element 104 and the posterior end region 107 of the annular element 104. The arc length can be sufficient, either individually or in combination with other shape deformation membranes 140, to cause a reactive shape change in the dynamic membrane 143 upon inward (or outward) movement of the deformation membrane 140. Movement of the shape deformation membrane 140 in a generally inward direction towards the optical axis A of the AIOL 100 during accommodation can cause outward flexure or bowing of the dynamic membrane 143 without affecting the overall optic zone diameter in any axis. The shape deformation membrane 140 can have a flexibility such that it is moveable and can undergo displacement relative to the annular element 104 of the lens body 105, the static element 150, and the anterior optic 145. For example, the shape deformation membrane 140 can be more flexible than adjacent regions of the annular element 104 such that it is selectively moveable relative to the annular element 104 and the perimeter region 144 of the anterior optic 145. The shape deformation membrane 140 can have a resting position. The resting position of the shape deformation membrane 140 can vary. In some implementations, the resting position is when the shape deformation membrane 140 is positioned generally perpendicular to a plane P parallel to the anterior optic 145 such that it has a cross-sectional profile that is vertically oriented, parallel to the optical axis A (see FIG. 2F). The resting position of the shape deformation membrane 140 can also be angled relative to the optical axis A of the lens body 105. As shown in FIGS. 13A-13B, the cross-section of the side deformation membrane 140 may be angled peripherally at an angle $\Theta^1$ relative to the annular structure 104. In some implementations, the angle $\Theta^1$ is between 45-89 degrees. In some implementations, the $\Theta^1$ is 80-89 degrees. Alternatively, the cross sectional profile of the deformation membrane 140 may be a curvilinear structure protruding peripherally from the optical axis A of the lens body 105 (see FIG. 13C). The peripheral protruding side deformation membrane 140 may protrude peripherally 0.05 mm-0.5 mm. In some implementations, the curvilinear protrusion extends 0.1 mm-0.3 mm away from optical axis A of the lens body 105 relative to the equator region 108 of the annular structure 104. The shape and relative arrangement of the one or more side deformation membranes 140 provides the lens with a low force, low movement, high accommodative function, as will be described in more detail below.

The movement of the shape deformation membrane 140 can be a compression, collapse, indentation, stretch, deformation, deflection, displacement, hinging or other type of movement such that it moves in a first direction (such as generally toward an optical axis A of the lens body 105) upon application of a force on the shape deformation membrane 140. The movement of the shape deformation membrane 140 can be located inside or outside the optic zone. Upon release of the force on the shape deformation membrane 140, the membrane 140 and/or other components of the AIOL 100 (e.g. the optical fluid 156 filling the sealed chamber 155) can have elastic memory such that the shape deformation membrane 140 returns towards its resting position. Depending on the coupling of the AIOL 100 within the eye, the shape deformation membrane 140 can also be pulled outward away from the optical axis A of the AIOL 100.

The shape deformation membrane 140 lies adjacent or is coupled to a respective force translation arm 115. In some implementations, as the force translation arm 115 is moved inwardly toward the optical axis A of the AIOL 100 due to ciliary muscle contraction, the force translation arm 115 abuts an outer surface of the shape deformation membrane 140 and applies a force against the outer surface. Thus, the contact between the shape deformation membrane 140 and the force translation arm 115 can be reversible contact such that upon ciliary muscle contraction the force translation arm 115 is urged against the outer surface abutting the membrane 140 and urging it inwardly. Upon ciliary muscle relaxation, the shape deformation membrane 140 returns to its resting position and the force translation arm 115 returns to its resting position. The elastomeric nature of the movable components (i.e. the dynamic membrane and/or the shape deformation membranes) can cause a return of the force translation arms 115 to their resting position. In other implementations and as best shown in FIG. 2F, the shape deformation membrane 140 is coupled to or integral with its respective force translation arm 115. As with the other implementation, upon ciliary muscle contraction the force translation arm 115 and shape deformation membrane 140 move in concert from a resting position to a generally inwardly-displaced position causing shape change of the dynamic membrane 143.

The number and arc length of each deformation membrane 140 can vary and can depend on the overall diameter and thickness of the device, the internal volume, refractive index of the material, etc. Generally, the annular element 104 provides sufficient rigidity and bulk to the AIOL such that it can be handled and manipulated during implantation while the deformation membrane(s) 140 are sufficiently flexible to allow the force translation arms to change the shape of the sealed chamber 155. Depending on the overall diameter and thickness of the AIOL 100, the arc length of the shape deformation membrane 140 can be at least about 2 mm to about 8 mm. In some implementations, the AIOL has a single shape deformation membrane 140 with an arc length of between about 2 mm to about 8 mm. The single shape deformation membrane 140 can be designed to move between about 10 µm and about 100 µm upon application of forces as low as about 0.1 grams of force (gf) to achieve at least a 1 D, or 1.5 D, or 2 D, or 2.5 D, or 3 D change in the dynamic membrane 143. In another implementation, the AIOL can have two, opposing shape deformation membranes 140 each having an arc length that is between about 3 mm and about 5 mm. The shape deformation membranes 140 can be designed to move between about 25 µm and about 100 µm each upon application of about 0.25 g force to 1.0 g force achieve at least a 1 D change in the dynamic membrane 143. This is described in more detail below.

The shape deformation membranes 140 can move or collapse relative to the rest of the lens body upon application of a degree of force. Generally, the AIOL is designed such that very low forces are sufficient to cause micron movements to cause sufficient diopter changes and with reliable optics. The force applied to achieve movement of the dynamic membrane 143 of the lens body 105 to effect accommodation can be as low as about 0.1 grams of force (gf). In some implementations, the force applied can be between about 0.1 gf to about 5.0 gf or between about 0.25 gf to about 1.0 gf or between about 1.0 gf to about 1.5 gf. The movements of the deformable regions of the lens body 105 (e.g. shape deformation membrane 140) relative to the central portion of the lens body 105 (e.g. dynamic membrane 143) in response to forces applied to achieve accommodation can be as small as about 50 µm. The movements of the shape deformation membrane 140 of the lens body relative to the dynamic membrane 143 in response to forces applied can be between about 50 µm to about 500 µm, between about 50 µm to about 100 µm, between about 50 µm to about 150 µm, or between about 100 µm to about 150 µm. The ranges of forces applied (e.g. about 0.1 gf to about 1 gf) that result in these ranges of movement in the shape deformation membrane 140 (e.g. 50 µm-100 µm) can provide the devices described herein with an accommodating capability that is within a dynamic range of greater than at least ±1 D and preferably about ±3 diopters (D). In some implementations, the power is between ±4 D and ±6 D for about 100-150 µm movement. The devices described herein can have an accommodating range that is at least ±1 D for about 100 µm movement of the shape deformation membrane 140 and about a force of at least 0.25 gf applied to the shape deformation membrane 140. In other implementations, the devices can have an accommodating range that is at least ±1 D for about 50 µm movement and at least about 1.0 gf. In other implementations, the devices can have an accommodating range that is at least ±3 D for about 100 µm movement and at least about 1.0 gf. In other implementations, the devices can have an accommodating range that is at least ±3 D for about 50 µm movement and at least about 0.1 gf.

The micron movements described herein can be asymmetrical micron movements (e.g. from one side of the device) or can be symmetrical micron movements from opposing sides of the device or evenly distributed around the device relative to the optical axis. Whether the micron movements are asymmetric or symmetrical, the outward bowing of the dynamic membrane 143 achieved is spherical. The micron movements described herein also can be a total collective movement of the shape deformation membranes 140. As such, if the lens 100 includes a single shape deformation membrane 140, that single membrane is capable of desired micron movement (e.g. 50 µm-100 µm) to achieve desired dioptric change (e.g. at least 1 D to about 3 D change). If the lens 100 includes two shape deformation membranes 140, the membranes together are capable of the achieving between 50 µm-100 µm movement to achieve the at least 1 D dioptric change. The dioptric change achieved by the devices described herein can be at least about 1 D up to approximately 5 D or 6 D change. In some implementations, the dioptric change can be between 7 D and 10 D, for example, for patients having macular degeneration.

As mentioned above and still with respect to FIGS. 2A-2F, the lens body 105 can include a static element 150 coupled to the annular element 104. The static element 150 can couple to the posterior end region 107 of the annular element 104 whereas the anterior optic 145 can be coupled to an anterior end region of the annular element 104 such that the static element 150 and anterior optic 145 are located opposite one another along the optical axis A of the AIOL 100. The way in which the static element 150 couples with the annular element 104 can vary. For example, as shown in FIG. 2E-2F, the static element 150 can have a flat surface 151 on a first side, a curved surface 152 on a second, opposite side, and a peripheral connecting ring 153 having a sealing surface 154 configured to mate with the posterior end region 107 of the annular element 104. The static element 150 can be positioned outside the lens body 105 such that the flat surface 151 forms the inner surface facing the sealed chamber 155 of the lens body 105 and the curved surface 152 is in contact with the fluid of the eye. Alternatively, the static element 150 can be positioned inside the lens body 105 such that the flat surface 151 is in contact with the fluid of the eye and the curved surface 152 forms the inner surface facing the sealed chamber 155 of the lens body 105. The sealing surface 154 of the peripheral connecting ring 153 can connect with the posterior end region 107 of the annular element 104 such that the peripheral connecting ring 153 is spaced a distance away from the equator region 108 of the annular element 104. The internal flat surface 151 of the static element 150 can abut an inner surface of the perimeter region 144 of the anterior optic 145.

The static element 150 can be optically clear and provide support function without affecting the optics of the AIOL 100. As such, the static element 150 can have zero power and can form a posterior support to the lens body 105. The static element 150 can be formed of silicone, urethane, acrylic material, a low modulus elastomer, or combinations thereof. The static element 150 can be or include a static optic to correct to emmetropic state, or can be of an appropriate power for an aphakic patient (usually ±10 D to ±30 D). If the AIOL 100 is being used in conjunction with a separate capsular IOL (e.g. as a "piggyback" lens), the power can be in the range of about −5 D to about +5 D to correct for residual refractive or other optical aberrations in the optical system of the eye. The static element 150 can be plano-convex, convex-plano, convex-convex, concave-convex or any other combination. The static element 150 (or the lens positioned posteriorly) can be a toric lens, spherical lens, aspheric lens, diffractive lens or any combination of both, for example, in order to reduce or compensate for any aberrations associated to the flexible lens. The relative refractive indices of the static element 150 and the fluid surrounding it (whether that is the fluid of the eye or optical fluid 156 within the sealed chamber 155) will determine the power of the static element 150 for any given shape.

The AIOL 100 can include any of a variety of combinations of reinforcements and/or supports to provide mechanical stability to the assembled lens 100. For example, the reinforcements may be in the peripheral regions of the anterior lens 145 and/or the static element 150. The reinforcements can be either optically clear or opaque. The reinforcing structures may be formed of a rigid polymer, including but not limited to silicone, polyurethane, PMMA, PVDF, PDMS, polyamide, polyimide, polypropylene, polycarbonate, etc., or combinations thereof. Other regions of the lens 100 can include one or more reinforcements or supports as well. In some implementations, the one or more supports can be positioned external to the sealed chamber 155 such that the supports surround at least an outside portion of the lens body 105. For example, the external support can be a generally annular element extending around a perimeter of the lens body 105 and have a central opening through which at least the dynamic membrane 143 of the anterior optic 145 is aligned such that the dynamic membrane 143 is available for outward deformation.

Figure 3C:
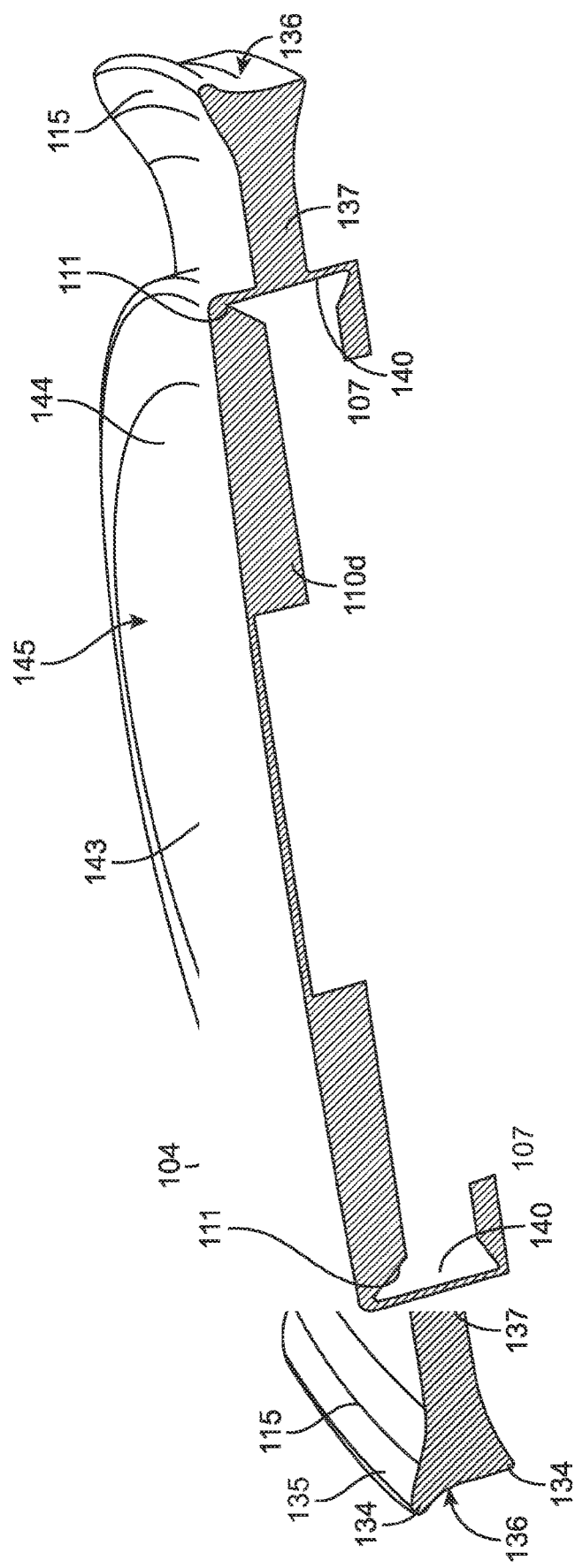
FIG. 3C is a cross-sectional view of the anterior lens portion of FIG. 3B taken along line C-C.

In other implementations, the AIOL 100 includes one or more internal supports 110 located within the AIOL 100, such as within or facing the sealed chamber 155 of the lens body 105 (see FIGS. 3A-3C). The one or more internal supports 110 can be thickened portions on an interior side of the outer, perimeter region 144 of the anterior optic 145. The one or more internal supports 110 can also be separate components coupled to the AIOL. The one or more internal supports 110 can be coupled to and/or embedded inside the perimeter region 144 of the anterior optic 145. The internal supports 110 can act to mechanically isolate the optical components of the lens body 105 from optical distortion during movement of the moving parts of the AIOL 100, such as the force translation arms 115, the shape deformation membrane 140, and the dynamic membrane 143. The internal supports 110 can be formed of a material (or materials) that is harder, thicker and/or more rigid than the shape deformation membrane 140 or the dynamic membrane 143 of the anterior optic 145 to prevent inadvertent movements of the moving parts of the device. Alternatively, the internal supports 110 may be made of the same material as the shape deformation membrane 140 or the dynamic membrane 143 of the anterior optic 145 and accomplish the mechanically isolating function due to the geometry of the support structure. The support 110 can be formed of a rigid polymer, including but not limited to silicone, polyurethane, PMMA, PVDF, PDMS, polyamide, polyimide, polypropylene, polycarbonate, etc., or combinations thereof. For example, the internal support 110 can be a combination of multiple silicones or silicone with a rigid or semi-rigid skeletal insert.

Figure 3D:
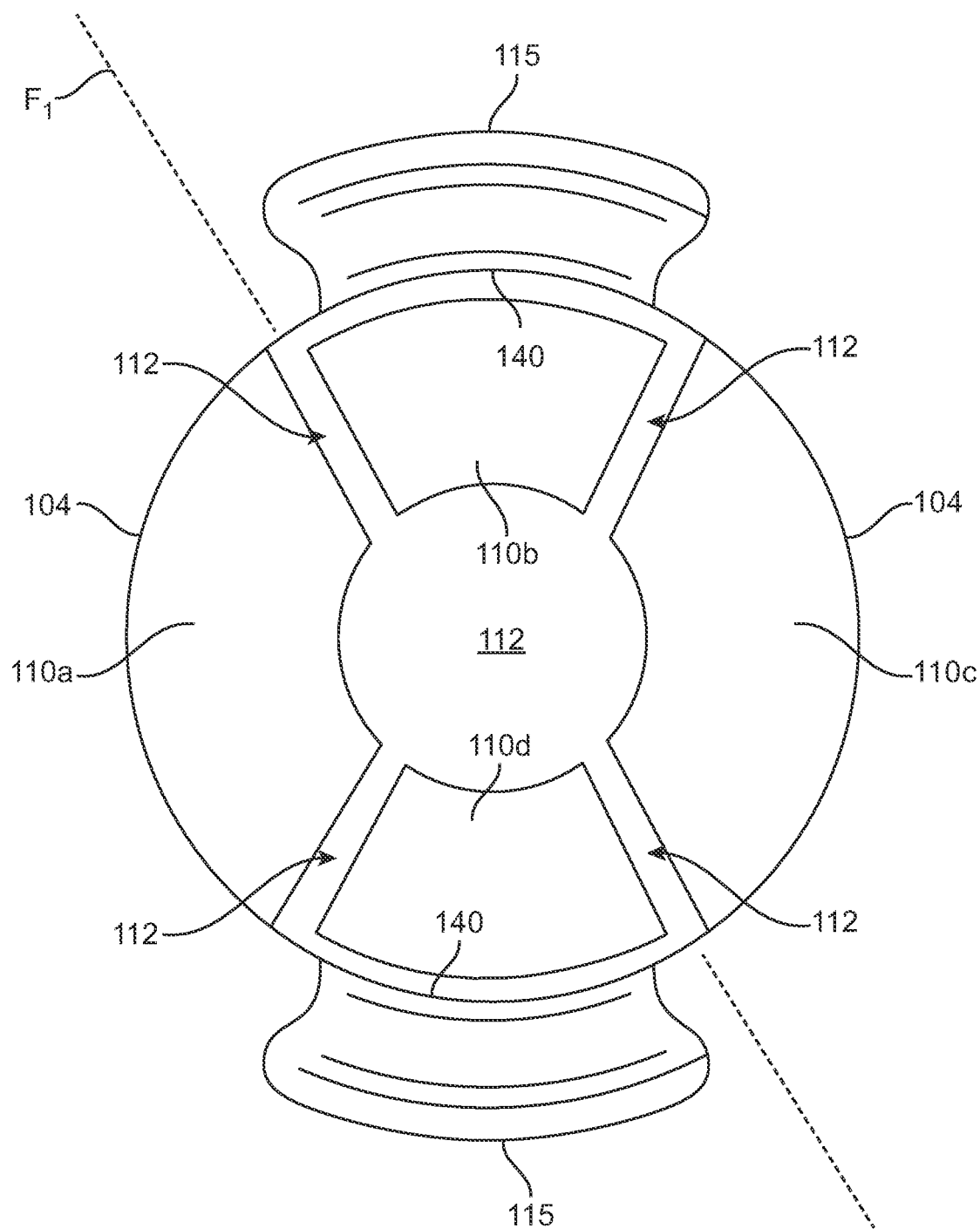
FIGS. 3D-3G are schematic views of anterior lens portions of various implementations of an AIOL.
Figure 3E:
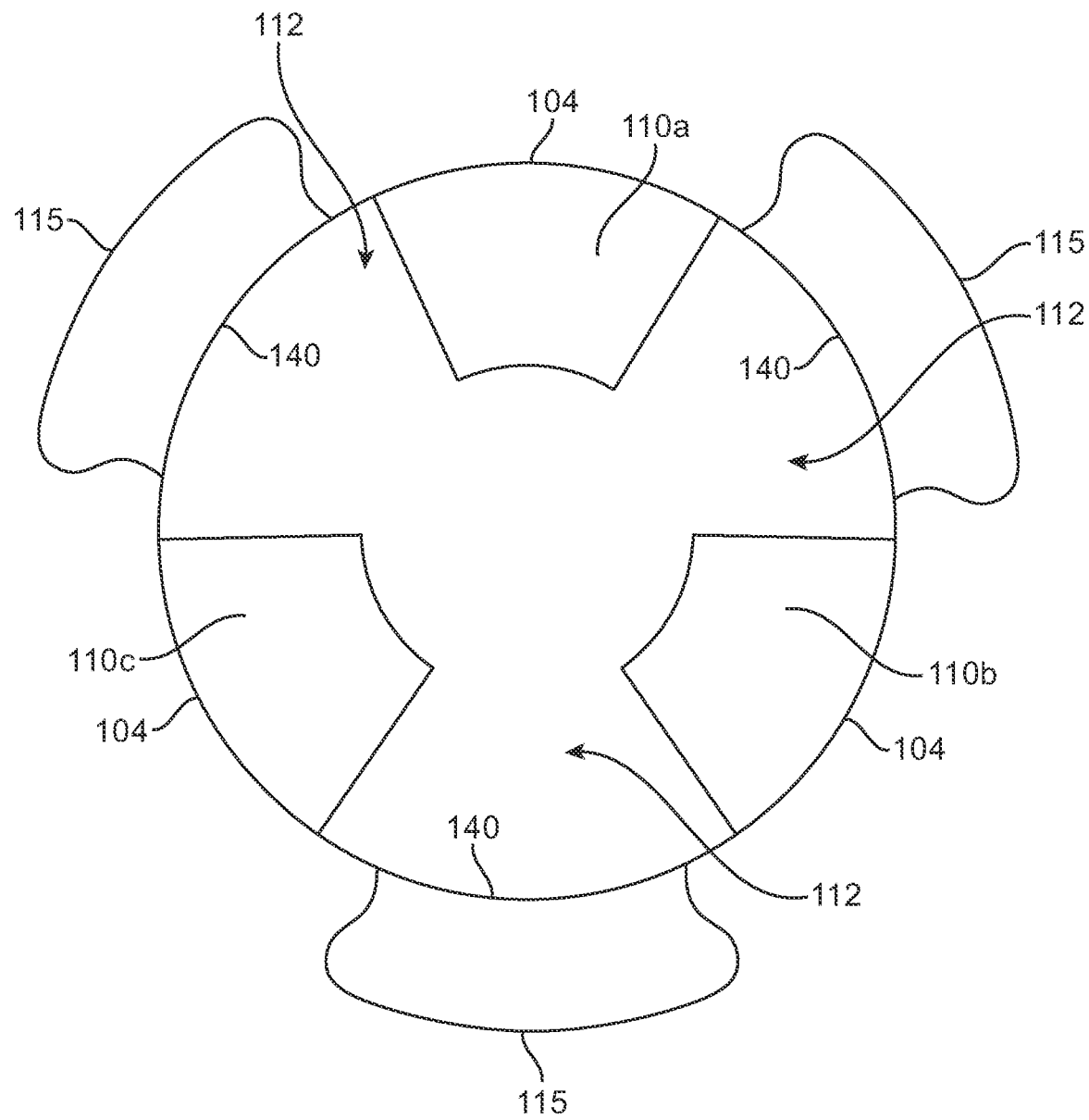
Figure 3F:
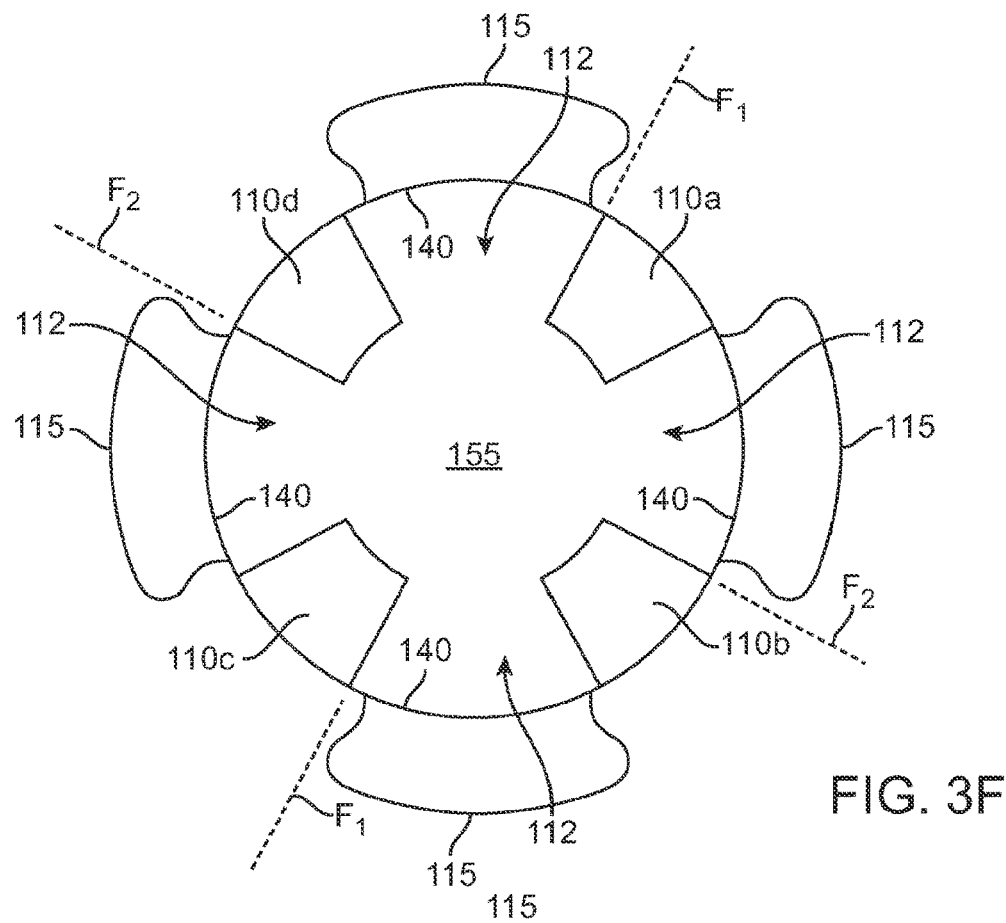
Figure 3G:
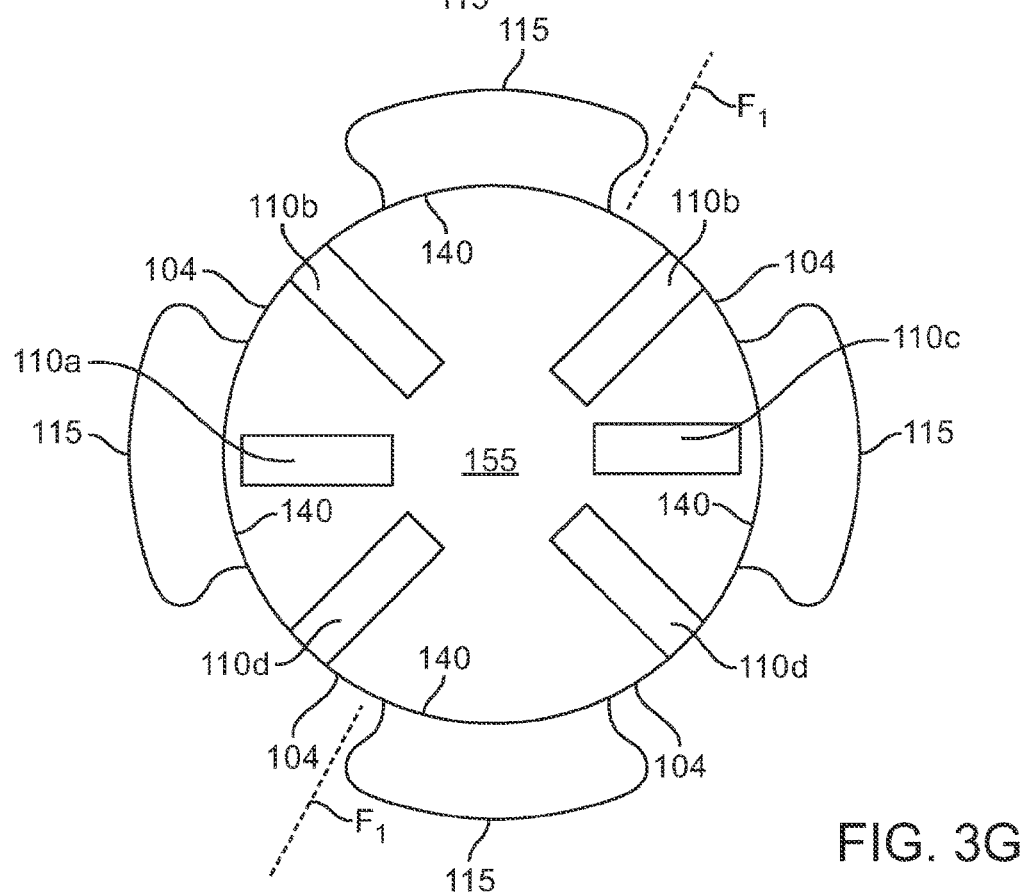

FIGS. 3A-3C illustrate an implementation of the lens body 105 including a perimeter region 144 having a plurality of internal supports 110a, 110b, 110c, 110d. The internal supports 110 can be relatively planar elements that lie generally parallel to the central, longitudinal plane P of the AIOL 100. An outer region of each support 110 can be positioned adjacent to the equator region 108 of the annular element 104 of the lens body 105 and extend inward towards the dynamic membrane 143 of the anterior optic 145. The outer region of the support 110 can be coupled to or integral with the equator region 108 of the annular element 104 or the outer region of the support 110 can be spaced away from the equator region 108 of the annular element 104. FIG. 3A illustrates an implementation having a support 110b that is spaced away from the equator region 108 of the annular element 104 near where the deformation membrane 140 extends along an arc length of the equator region 108. This spacing away from the deformation membrane 140 provides tolerance such that the deformation membrane 140 does not prematurely abut or contact the support 110b during inward accommodative movements. As another example, FIG. 3D shows the outer region of two of the inner supports 110a and 110c support the lens body 105 along an arc of the outer perimeter region such that they are coupled to, integral with, or otherwise contiguous with the equator region 108 of the annular element 104 of the lens body 105. The outer region of the other two inner supports 110b and 110d are spaced a distance away from the equator region 108 of the annular element 104 of the lens body 105, for example, near where the shape deformation membrane 140 extends along an arc length of the annular element 104. This allows for unhindered inward movements of the shape deformation membrane 140 and prevents contact between the inner support 110b, 110d and the respective shape deformation membrane 140. Similarly, the inner supports 110 of FIG. 3G shows the outer region of supports 110b, 110d are coupled to, integral, or otherwise contiguous with the equator region 108 of the annular element 104 of the lens body 105 whereas the outer region of supports 110a, 110c are spaced a distance away from the equator region 108 of the annular element 104 of the lens body 105 near where the shape deformation membrane 140 is located.

The distribution of the internal supports 110 on the perimeter region 144 of the anterior optic 145 can ensure the supports 110 do not interfere with movements of the shape deformation membrane 140. For example, FIG. 3E shows the internal supports 110a, 110b, and 110c are distributed such that their outer regions couple to the annular element 104 between where the shape deformation membrane 140 and force translation arms 115 are located. Similarly, the internal supports 110a, 110b, 110c, and 110c of the implementation shown in FIG. 3F are distributed such that the outer regions couple with the annular element 104 in between where the shape deformation membrane 140 and force translation arms 115 are located.

The distribution and spacing of the one or more internal supports 110 relative to the shape deformation membrane 140 can minimize their contact with the moving parts of the lens whether near the perimeter region of the lens body 105 or the central region of the lens body 105. The shape of the internal supports 110 can also minimize or limit contact between the internal supports 110 and the shape deformation membrane 140. For example, as best shown in FIG. 3C, the outer region of the supports 110b, 110c can be beveled near where the supports couple to the annular element 104 such that the bevel 111 allow for inward movement of the shape deformation membrane 140 while avoiding contact between the membrane 140 and the outer perimeter of the supports. The bevel 111 can be a single bevel having an angle that is between about 10-80 degrees. It should be appreciated that the outer region of the one or more supports need not include a bevel. Contact between the shape deformation membrane 140 and the one or more internal supports 110 can be avoided in other ways aside from incorporating a bevel. For example, the one or more supports 110 can be spaced a distance away from the shape deformation membrane 140 (e.g. along the perimeter and/or away from the perimeter) to avoid contact. The internal supports 110 can also have a length between the outer regions to their inner regions such that they extend a distance towards the center of the lens body providing stability and support, but generally stop short of the central, dynamic membrane 143 of the anterior optic 145. As such, the internal supports 110 distributed around the lens body 105 can aid in creating a central step-down in thickness from the outer perimeter region 144 of the anterior optic 145 to the dynamic membrane 143 of the anterior optic 145.

As mentioned, the overall shape of each of the one or more supports 110 can vary. The internal supports 110 can have any of a variety of shapes including, but not limited to polygonal, pyramidal, triangular, rectangular, square, trapezoidal, and any of a variety of curvilinear shapes. In some implementations, the one or more supports 110 can have a wider dimension near the perimeter of the lens body 105 and a narrower dimension near the central, dynamic membrane 143 of the anterior optic 145. In other implementations, the one or more supports 110 can be elongate rod shapes. The perimeter region 144 of the anterior optic 145 can include a single inner support 110, two, three, four, five, six, or more separate internal supports 110. Thus, the distribution, size, shape, and number of the internal supports 110 can vary.

The lens body 105 can include a fixed volume, sealed chamber 155 filled collectively formed by the inner-facing surfaces of the shape deformation membrane 140, the anterior optic 145, and the static element 150 and filled by a fixed volume of an optical fluid 156. The inner-facing surfaces of the one or more inner supports 110 of the perimeter region 144 and the inner-facing surface of the dynamic membrane 143 of the anterior optic 145 also form part of the sealed chamber 155. Thus, the distribution, size, shape and number of the one or more supports 110 impacts the overall shape of the sealed chamber 155. Again with respect to FIGS. 3A-3G, the adjacent internal supports 110 can be spaced a distance away from one another forming a plurality of corridors 112 through the sealed chamber 155 between the pillars of support. The pillars of support can be shaped to form corridors 112 that are relatively narrow as shown in FIG. 3D. These narrower corridors 112 can create a sealed chamber 155 having a generally H- or X-shape. The pillars of support can be shaped to form relatively wider corridors 112 such as shown in FIGS. 3E-3G. These wider corridors 112 can create a sealed chamber 155 having the general shape of a plus, cross, star, trefoil, quadrafoil, cinquefoil, nephroid, or other shape.

The optical fluid 156 filling the sealed chamber 155 can be a non-compressible optical fluid and the volume of the sealed chamber 155 can be substantially identical to the volume of optical fluid 156. As such, the optical fluid 156 filling the chamber 155 does not cause significant outward bowing of either the dynamic membrane 143 or the deformation membrane 140 in the resting state when no substantial outside forces are applied to the AIOL 100. In some implementations, the sealed chamber 155 can be slightly overfilled with optical fluid 156 such that the dynamic membrane 143 has some outward bowing at rest. A small degree of resting outward bowing in the dynamic membrane 143 can reduce optical artifacts in the lens. However, no matter how much resting outward bowing is present in the dynamic membrane 143, the membrane 143 can still undergo additional outward bowing upon application of compressive forces on the shape deformation membrane 140 to provide accommodation. The pressure inside the sealed chamber 155 can be substantially equal to the pressure outside the sealed chamber 155. Because the optical fluid 156 in the sealed chamber 155 is non-compressible its shape deforms along with the shape of the chamber 155. Deformation of the chamber 155 in one location (e.g. micrometer inward movements of the shape deformation membrane 140) causes the non-compressible optical fluid 156 contained within the fixed-volume sealed chamber 155 to press against the inner-facing surfaces forming the sealed chamber 155. A reactive deformation of the sealed chamber 155 occurs in a second location to create sufficient accommodating change. The dynamic membrane 143 of the anterior optic 145 is configured to bow outward upon application of a force (e.g. due to relative thickness and/or elasticity) compared to other parts of the anterior optic 145 such as the perimeter region 144. Thus, inward movement of shape deformation membrane 140 urges the optical fluid 156 to deform along with the chamber 155 and press against the inner-facing surface of the anterior optic 145. This results in outward bowing and reshaping of the outer surface of the dynamic membrane 143 to cause the accommodative portion of the optic zone to become more convex increasing the power of the AIOL 100. The internal supports 110 provide sufficient stability to the lens body 105 so that application of the compressive forces on the shape deformation membrane 140 causes the micrometer movements with minimal distortion of the optics.

The optical fluid 156 contained within the sealed chamber 155 of the lens body 105 remains substantially within the optic zone during rest in both the unaccommodated, resting state and during accommodation. The optical fluid 156 remains within the lens body 105 and can contribute to the accommodative shape change of the dynamic membrane 143 by deforming in shape along with the deformation of the shape of the sealed chamber 155. It should be appreciated that this shape change of the dynamic membrane 143 can occur without actual flow of the optical fluid 156 within the sealed chamber 155, for example, from one part of the chamber to another. Rather, a force being applied on the shape deformation membrane 140 deforms the sealed chamber 155 in a first region that can cause a reactive deformation of the sealed chamber 155 in at least a second region. The sealed chamber 155 has a fixed volume and is deformable. The optical fluid 156 filling the sealed chamber 155 changes shape along with and depending on the shape of the sealed chamber 155. Inward deformation of one or more portions of the chamber 155, for example, movement of the shape deformation membrane 140 near the perimeter region of the lens body 105, can cause a reactive outward deformation of another portion of the chamber 155, for example, outward bulging of the dynamic membrane 143 of the anterior optic 145, due to the non-compressible optical fluid 156 inside the sealed chamber 155 pressing against its inner surface. The optical fluid 156 need not flow between separate chambers of the AIOL, but rather the optical fluid 156 can change shape along with the changing shape of the sealed chamber 155 to cause the accommodative portion of the optic zone of the anterior optic 145 to bow outward and increase the power of the AIOL 100. As described elsewhere herein, very small movements of the force translation arms 115 (or single force translation arm 115 in the case of an asymmetric mechanism) result in immediate, small movements in the shape deformation membrane 140 to change the shape of the dynamic membrane 143 and sufficient dioptric change. Whether these very small movements are symmetrical due to at least a pair of opposing force translation arms 115 or asymmetrical due to a single force translation arm 115, the outward bowing of the dynamic membrane 143 that is achieved is spherical and symmetrical.

Again with respect to FIGS. 2A-2F, the AIOL 100 can include one or more force translation arms 115 configured to move back and forth relative to the lens body 105 to cause the dioptric changes described elsewhere herein. The AIOLs described herein are particularly suited to harness the movements of the ciliary body applied directly onto the force translation arms 115 positioned against the ciliary structures into shape change of the lens. The force translation arms 115 are configured to harness and translate forces applied by the ciliary structures into the shape changes of the movable parts of the lens body 105 described above. Each force translation arm 115 can include an outer, contact portion 135 and an inner region 137 operatively coupled to a perimeter or equator region of the lens body 105 (see FIGS. 2E-2F). Inner regions 137 of each force translation arm 115 can be positioned in contact with or adjacent the shape deformation membrane 140 such that the force translation arm 115 can move relative to the relaxed, shape deformation membrane 140. For example, the force translation arm 115 can be spaced away from the membrane 140 during rest, moved inward during accommodation to abut against the membrane 140 urging the membrane 140 inward, and then upon release of force during disaccommodation move away from the membrane 140 to release the membrane 140 from the inward, deforming force. As such, the inner region 137 of the force translation arm 115 can come into reversible contact with the shape deformation membrane 140 depending on whether an accommodating force is applied by the surrounding eye tissue. Alternatively, the inner region 137 of each force translation arm 115 can be physically coupled to or integral with the outer surface of the shape deformation membrane 140 such that the force translation arm 115 and the membrane 140 move in concert with one another.

In some implementations, the inner region 137 of the force translation arm 115 can have a cross-sectional thickness taken along a plane between an anterior surface of the lens body 105 and the posterior surface of the lens body 105 that is narrower than a cross-sectional thickness of the annular element 104 of the lens body 105 taken along the same plane. This can allow for the inner region 137 of the force translation arm 115 to displace the deformation membrane 140 a distance inward between the anterior end region and the posterior end region of the annular element 104 without abutting against the annular element 104. The cross-sectional thickness of the inner region 137 of the force translation arm 110 can also allow for inward movement of the arm 115 without making contact with an internal support 110 positioned adjacent the deformable membrane 140 (see FIG. 2F). It should be appreciated however, that the cross-sectional thickness of the inner region 137 of the force translation arm 115 need not be narrower than the annular element 104. The outer contact portion 135 of the force translation arms 115 can, but need not, have a larger cross-sectional thickness than the inner region 137. It should be appreciated, however, that the outer contact portion 135 of the force translation arms 115 can also have the same cross-sectional thickness as the inner region 137. The outer contact portion 135 can also have rounded or curved contours.

The contact portions 135 of the force translation arms 115 can incorporate features that improve their connection with one or more of the ciliary structures without causing damage. Generally, the contact portions 135 avoid piercing or causing trauma to the ciliary structures. In some implementations, the contact portions 135 can interfere with the ciliary structures while providing an atraumatic surface to engage adjacent eye tissues such that movement can be transferred without causing trauma to the tissues themselves. The outer contact portion 135 can also be molded to have one or more concavities, indentations, grooves, teeth, combs, or other surface features to improve, for example, contact and/or interdigitation with eye tissues such as the ciliary process or zonular process.

Figure 5A:
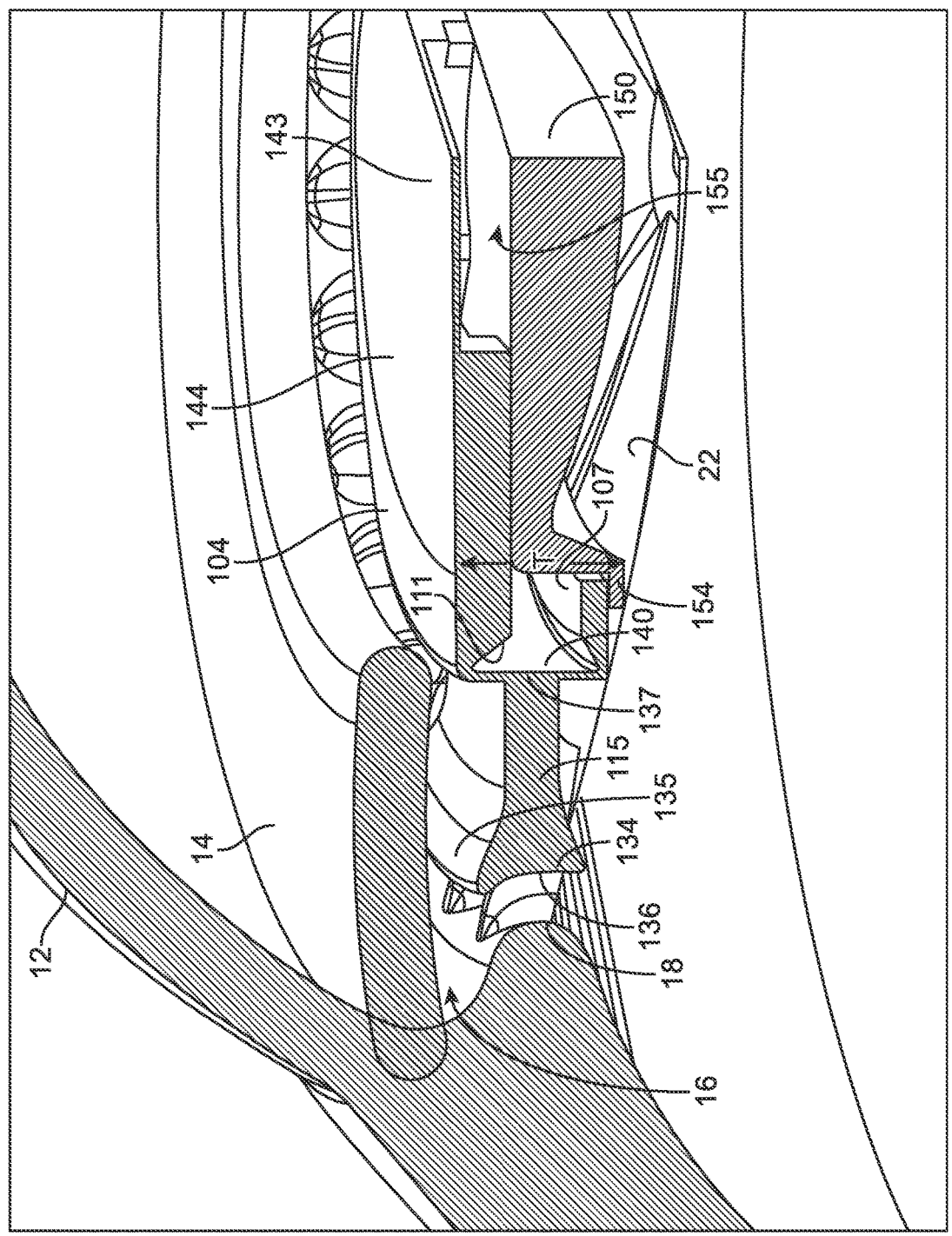
FIGS. 5A-5B are cross-sectional, partial perspective views of an accommodating intraocular lens device positioned within the eye.

In some implementations, the outer contact portion 135 can include one or more concavities 136. The concavities 136 can have a contour that matches a contour of a region of the eye with which the contact portion 135 associates. For example, upon implantation of the AIOL 100, the outer contact portion 135 of the force translation arms 115 can remain external to the capsular bag 22 such that the contact portion 135 can abut, contact, engage, functionally couple to or be in close association with one or more ciliary structures during accommodation and disaccommodation. The concavity 136 in the contact portion 135 can be sized to receive one or more portions of these eye tissues. For example, as shown in FIG. 5A, the concavity 136 can engage with the generally convex anatomy of the ciliary processes of the ciliary muscle 18. The convex anatomy of the eye can rest within the concavity 136 of the outer contact portion 135 providing for better fixation of the AIOL 100 within the ciliary sulcus of the eye. The concavity 136 can be centered and symmetrical within the outer contact portion 135 such that it creates upper and lower lips 134 on either side of the concavity 136 having the same length. Alternatively, the concavity 136 can be somewhat asymmetric such that it creates a slightly longer upper lip 134 compared to the slightly shorter lower lip 134 (see FIG. 3B). In some implementations, the upper lip 134 can have a length sufficient to extend within a portion of the ciliary sulcus when the ciliary process is received by the concavity 136. The lower lip 134 can also be longer than the upper lip 134. The outer surface of the contact portion 135 can also have a sharpened or beveled edges on an upper and/or lower edge such that the contact portion 135 has generally an S-shape in cross-section. The outer contact portion 135 can also include more than a single concavity 136 creating a plurality of smaller grooves in the surface of the outer contact portion 135 providing a surface texture and improve the friction between the force translation arm 115 and the surrounding anatomy.

Figure 7A:
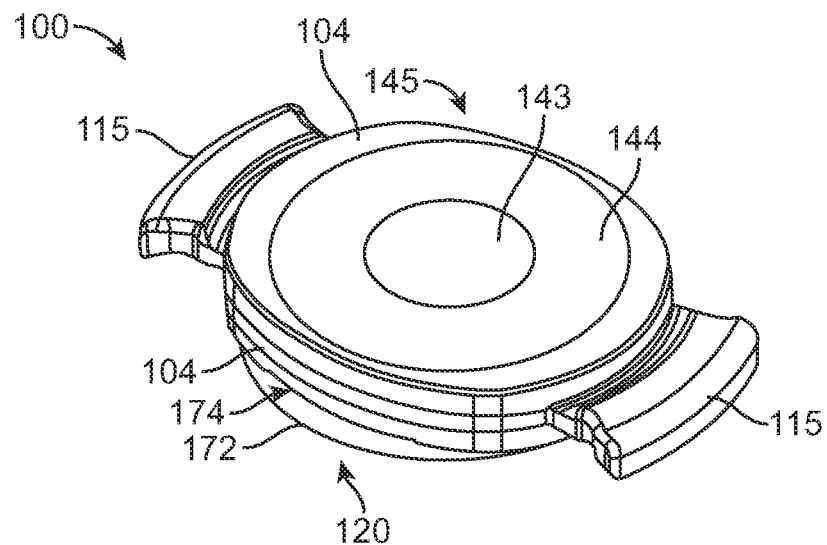
FIG. 7A is a perspective anterior view of an accommodating intraocular lens device having a stabilization system.
Figure 7B:
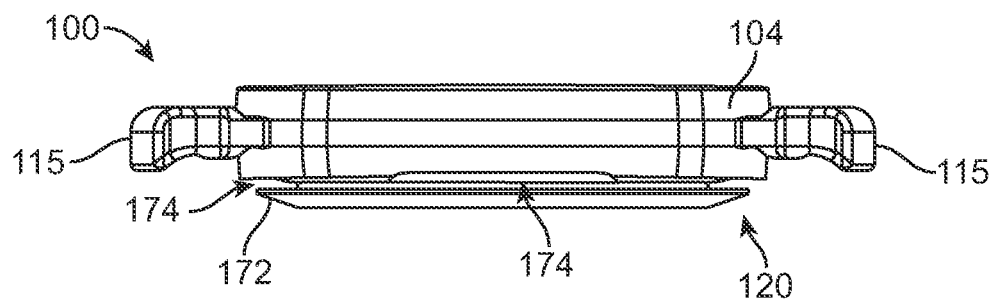
FIG. 7B is a side elevational view of the lens device of FIG. 7A.
Figure 7C:
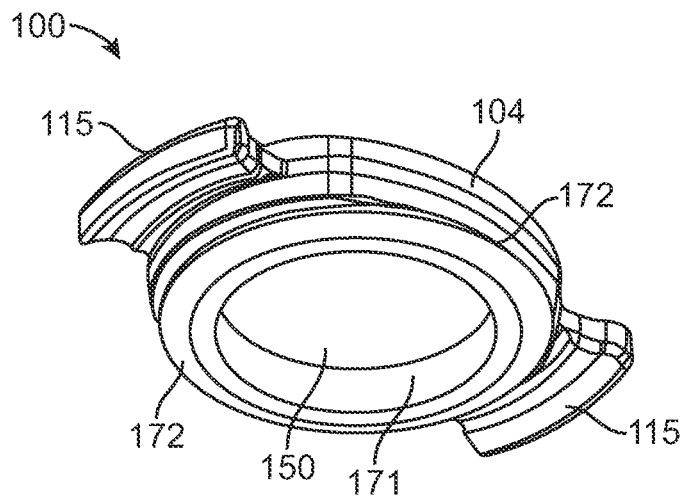
FIG. 7C is a perspective posterior view of the lens device of FIG. 7A.
Figure 7D:
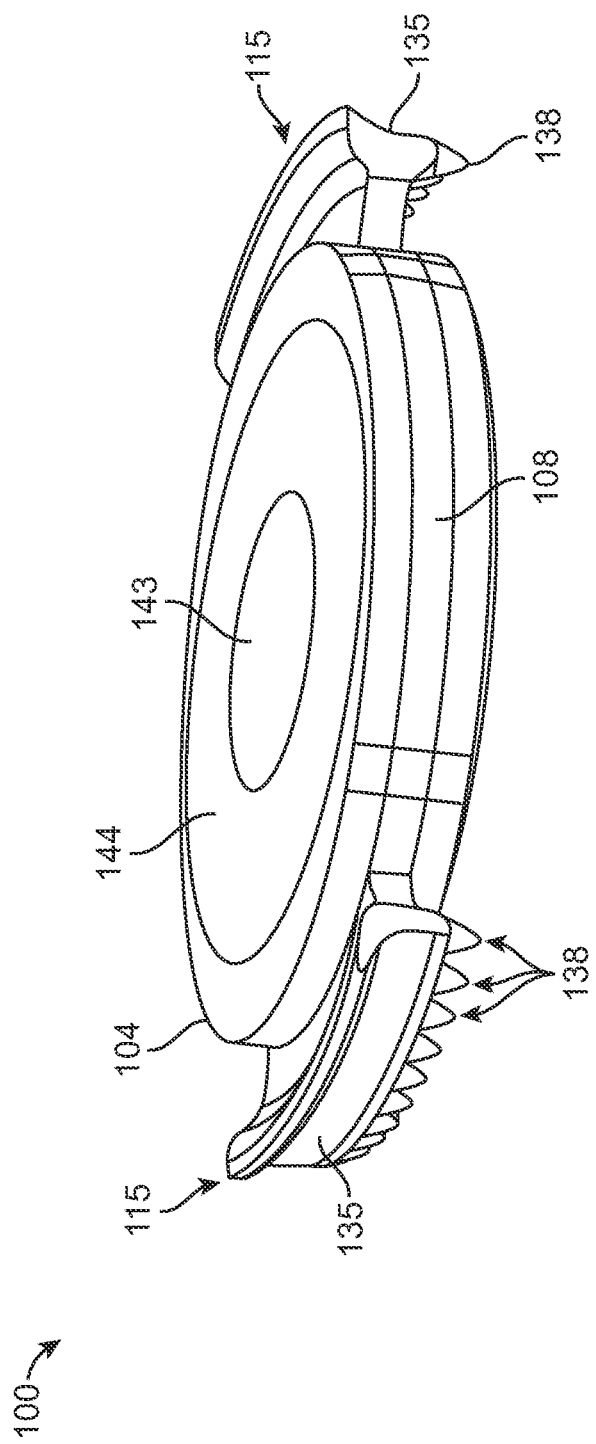
FIG. 7D is a perspective anterior view of a lens device incorporating prongs on an outer portion of the force translation arms.

In some implementations, the outer contact portion 135 can additionally include a plurality of prongs 138 extending posteriorly from the lower lip 134 of the force translation arm 115 (see FIG. 7D). The prongs 138 can have any of a variety of shapes such as conical, wedge, spear, hook, or other shape such that the prongs 138 can extend between the zonules and/or the ciliary processes. The prongs 138 can, but need not be sharp. In some implementations, the prongs 138 can terminate at an atraumatic end such that they do not damage or tear eye tissues. The prongs 138 can be flexible such that they are more easily positionable between the zonules or processes. In other implementations, the prongs 138 are relatively rigid. The prongs 138 can have a length sufficient to extend at least a distance between adjacent zonules and/or processes in order to provide fixation of the force translation arms 115 within the eye.

The outer portion 135 can have an overall shape such that it extends along an arc length configured to engage with a corresponding arc length of the annular ciliary structures (see FIG. 3A). The arc length of the outer portion 135 can be longer than the arc length of the inner region 137 such that the force translation arms 115 take on a flared shape. The arc length of the outer portion 135 can also be generally the same or slightly shorter than the arc length of the inner region 137 such that the force translation arms 115 take on a rectangular shape or tapered shape, respectively. In some implementations, the force translation arms 115 can be wider such that they have a longer arc length. A wider arm 115 can displace more material than a narrower force translation arm 115 even with small (micro-range) inward movements by the arm 115. A force translation arm 115 that extends along a greater circumference of the lens body (i.e. have a longer arc length) can be made thinner from an anterior-to-posterior direction and still result in the same amount of displacement with each movement as an arm that extends along a shorter arc length and as a greater thickness in an anterior-to-posterior direction. A thinner force translation arm 115 has an advantage over the thicker arm in that it can be more easily folded or urged into a "taco" shape for implantation through smaller openings. Each force translation arm 115 can include a region configured to provide sufficient accommodation upon inward movement as well as cross-sectional dimension to encourage folding or bending of the arms 115 and thus the AIOL 100. For example, in some implementations, each arm 115 can have a central region 116 that has a thinner cross-sectional dimension in an anterior-to-posterior direction compared to a cross-sectional dimension on either side of the central region 116 (see FIGS. 18A-18B). This allows for the force translation arms 115 and thus, the AIOL 100 to be folded down the center along a central axis A extending through these central regions 116.

Figure 14A:
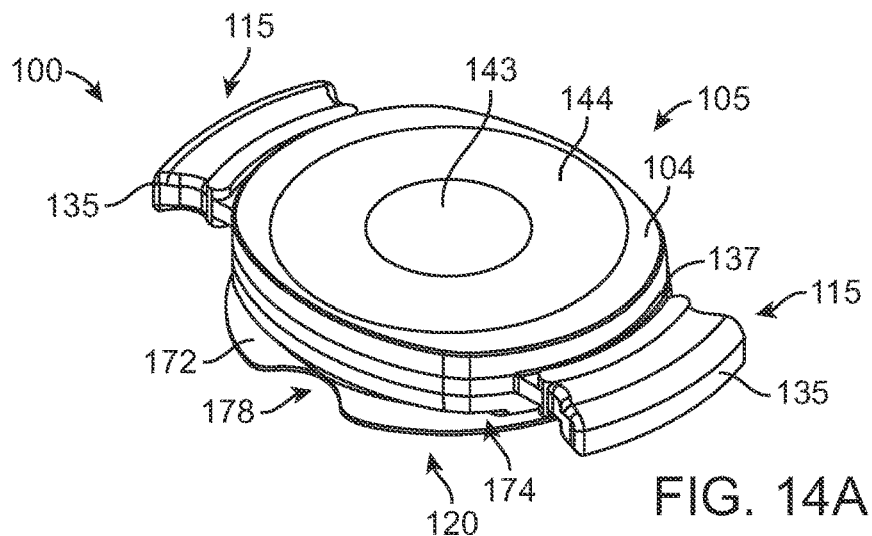
FIG. 14A illustrates a perspective view of an implementation of an accommodating intraocular lens device.
Figure 14B:
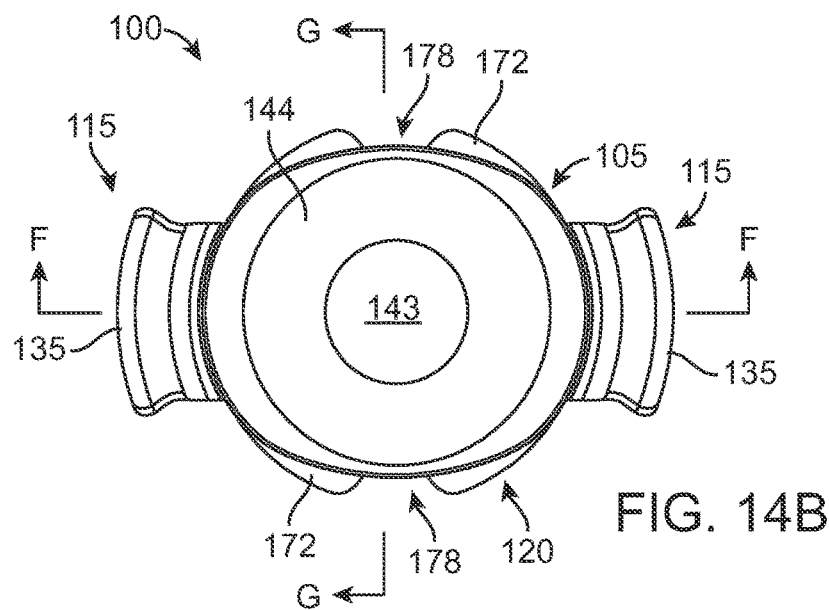
FIGS. 14B-14C illustrate a top plan view and a bottom plan view, respectively, of the device of FIG. 14A.
Figure 14C:
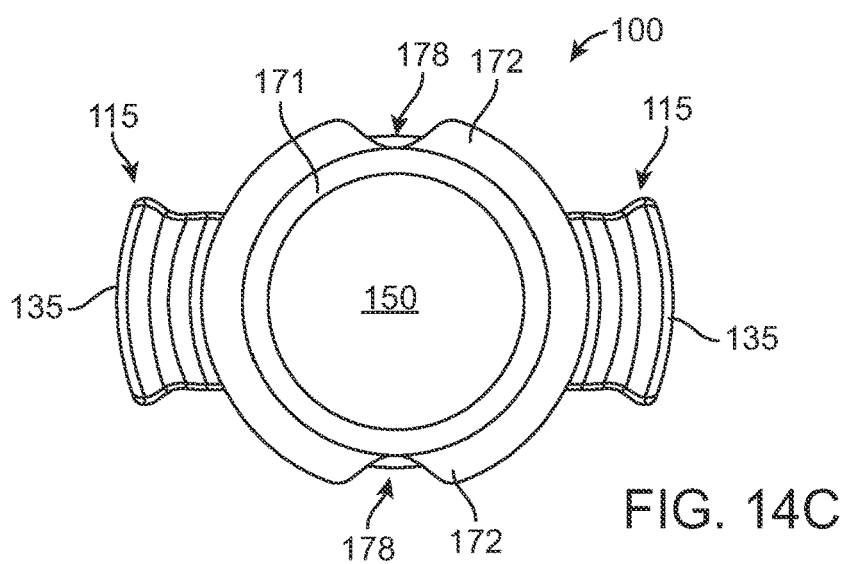
Figure 14D:
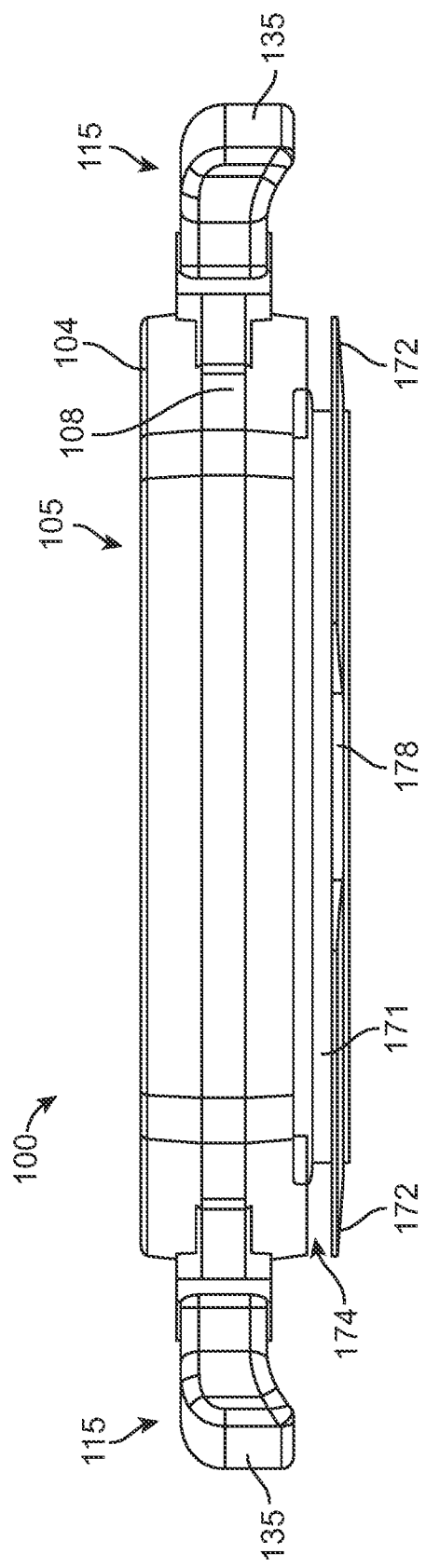
FIGS. 14D-14E illustrate side elevational views of the device of FIG. 14A.
Figure 14E:
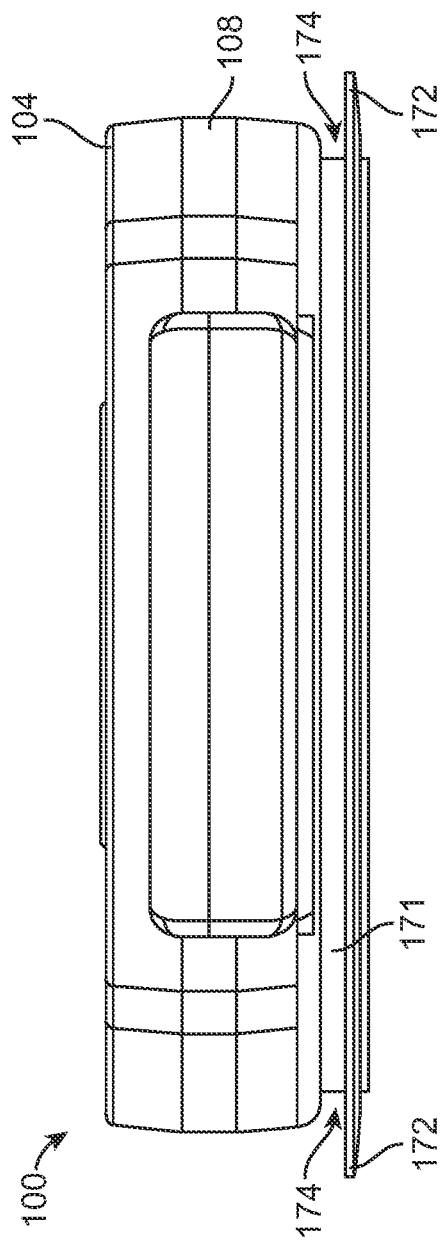
Figure 14F:
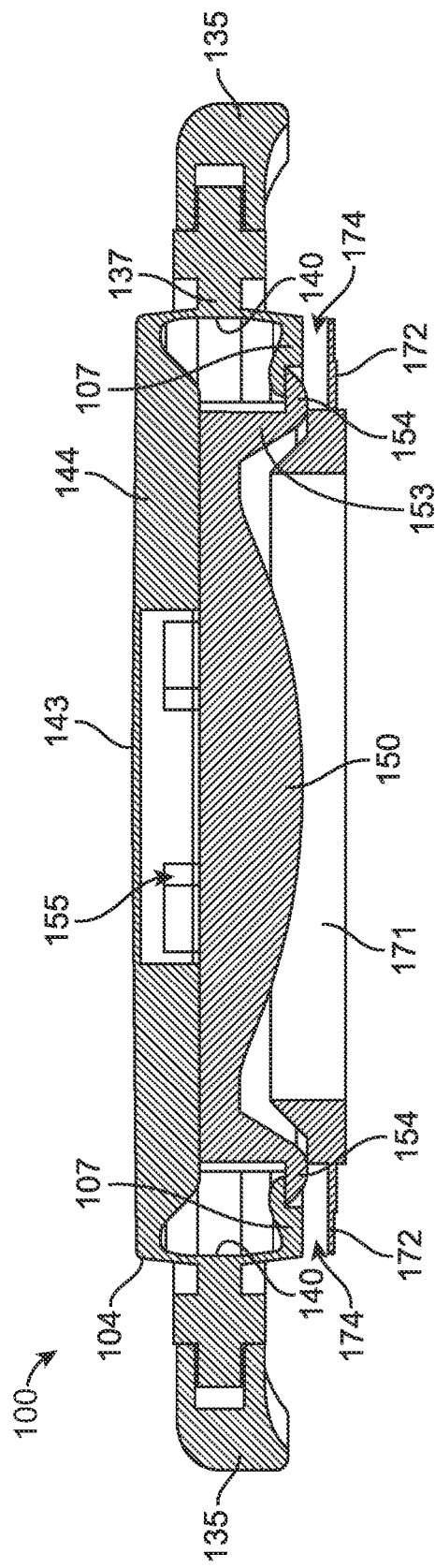
FIG. 14F illustrates a cross-sectional view of the device of FIG. 14B taken along line F-F.
Figure 14G:
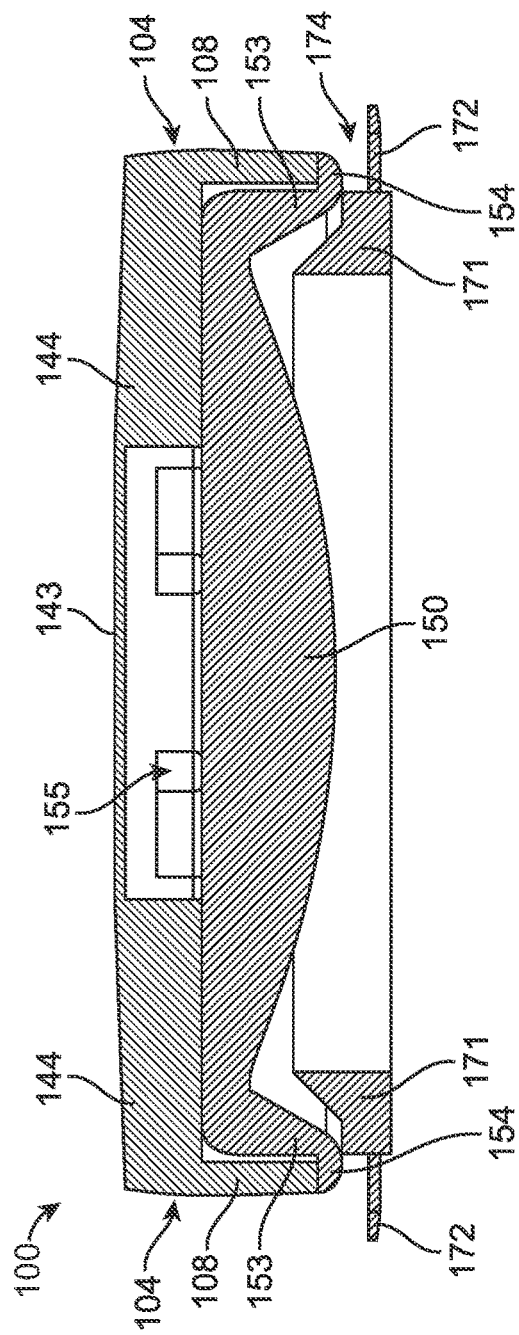
FIG. 14G illustrates a cross-sectional side view of the device of FIG. 14B taken along line G-G.
Figure 14H:
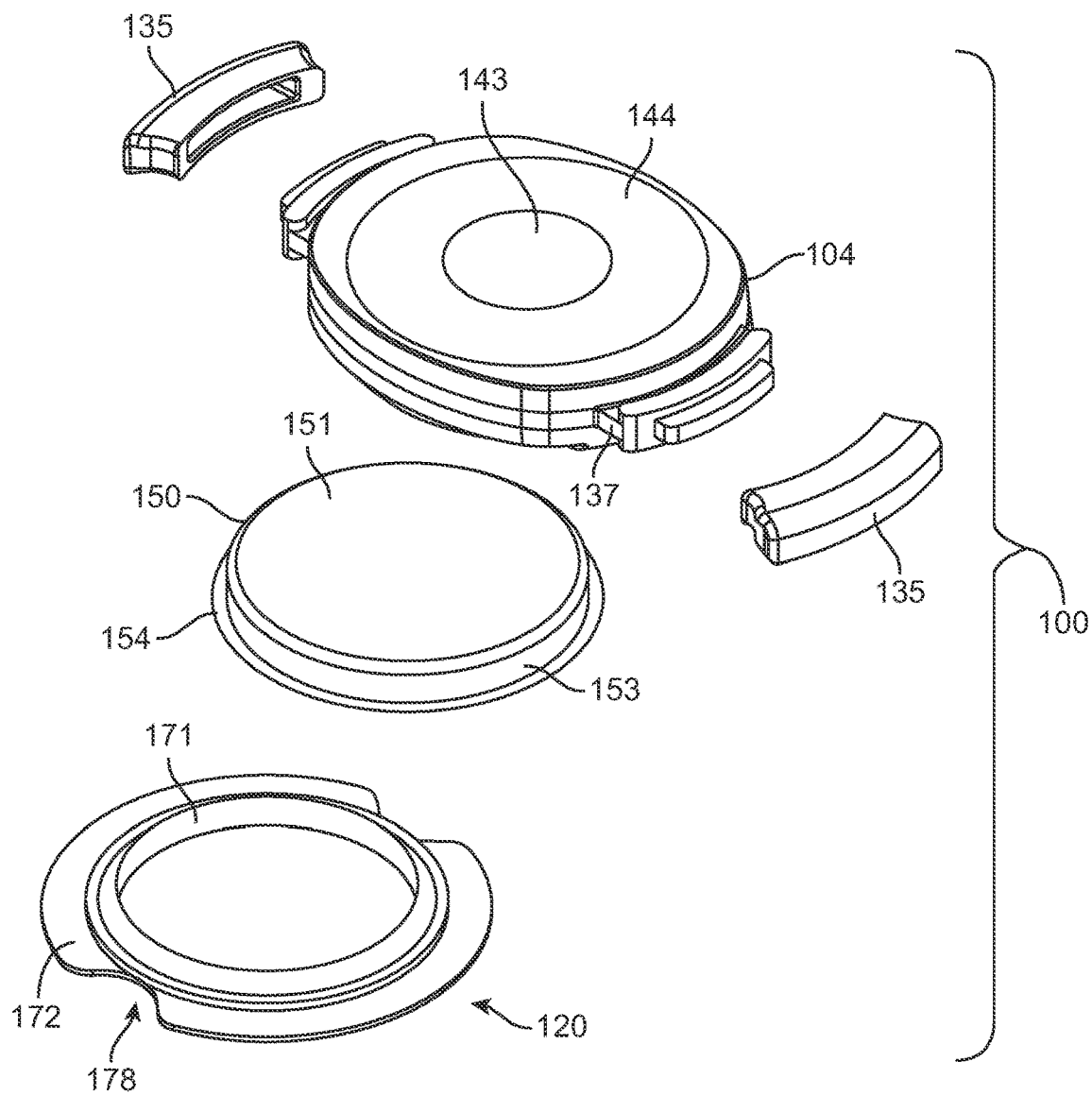
FIG. 14H illustrates an exploded, perspective view of the device of FIG. 14A.

In some implementations, the force translation arm 115 is a unitary element having an inner portion 137 and an outer portion 135. The outer portion 135 also can be a separate element capped onto a peripheral end of the force translation arm 115 such that the force translation arm 115 is formed of two components coupled together. FIG. 14F illustrates an implementation in which the outer portion 135 is formed of a separate element capping the inner portion 137. The outer portion 135 can be manufactured to have a customized length suitable for a particular patient. For example, the lens body 105 and inner portion 137 of the force translation arms 115 can be manufactured as a standard size component and the outer portion 135 can be manufactured separately to have a thickness and/or length sized according to measurements taken of a patient. Thus, coupling the customized outer portion 135 onto the inner portion 137 provides an overall diameter of the lens 100 that is sized for the diameter of a specific patient. Further, the outer portion 135 can be formed of a material that is significantly softer than the material of the inner portion 137 such that the outer portion 135 provides a softer contact surface for abutting against delicate eye tissues outside the capsular bag as described elsewhere herein.

It should be appreciated that the various components and features described herein can be incorporated into the AIOL 100 in any of a number of combinations. As such, description of a particular feature shown with respect to a particular drawing is not intended to be limiting in that the feature can be incorporated into another implementation of an AIOL 100 described herein. For example, the outer portion 135 that can be a separate component from the inner portion 137 in order to provide customization of length and fit can, but need not include any of the various features described for the outer portion 135 including, but not limited to prongs, grooves, concavities and the like.

The AIOL 100 can be implanted such that the contact portion 135 of the force translation arms 115 is either in resting contact or readily in contact upon contraction of the ciliary muscle 18 with at least one of the ciliary structures (i.e. zonules, ciliary processes, ciliary muscle, and/or ciliary body) to drive shape change of the optics during accommodation and disaccommodation. In a preferred implementation, the AIOL 100 is implanted such that the contact portion 135 of the force translation arms 115 lies in resting contact or ready contact with the ciliary body apex. In another preferred implementation, the AIOL 100 is implanted such that the contact portion 135 of the force translation arms 115 lies in resting or ready contact with the ciliary body. In some instances, the AIOL 100 is sized such that it is generally oversized relative to the ciliary structures. This can ensure contact between the force translation arms 115 and the ciliary structure during accommodation. In some implementations, the AIOL is oversized by at least about 0.80 mm, 0.75 mm, 0.70 mm, 0.65 mm, 0.60 mm, 0.55 mm, or 0.05 mm to guarantee ciliary contact with the force translation arms 115. It should be appreciated that the AIOL need not be oversized and in some circumstances oversizing of the AIOL may be avoided. For example, accurate measurements of the ciliary diameter at the plane of the AIOL may be relied upon to ensure the fit of the AIOL is suitable and optimized for a particular patient.

The force translation arms 115 described herein can have a fixed length. The fixed length force translation arms 115 can have a size selected that is appropriate for each patient based on pre-operative measurements. Alternatively, the length of the force translation arms 115 can be adjustable. The adjustment of the force translation arms 115 length can be performed prior to, during, or any time after insertion in the eye. Along with the adjustment of the length of the force translation arms 115, the position of the force translation arms 115 relative to the one or more ciliary structures can vary. In some implementations, the force translation arms 115 can extend generally parallel to the plane of the AIOL 100 or can be angled relative to the plane of the AIOL 100.

Contraction of the ciliary muscle and inward/anterior movement of one or more of the ciliary structures towards the optical axis A of the AIOL 100 applies a force against the contact portions 135 of the force translation arms 115. The force translation arms 115 are rigid enough relative to the deformation membrane 140 to transfer the forces applied by one or more moving parts of the eye (e.g. one or more ciliary structures) to cause inward movement of the deformation membrane 140. In some implementations, the force translation arms 115 can be a rigid polymer such as silicone, polyurethane, PMMA, PVDF, PDMS, polyamide, polyimide, polypropylene, polycarbonate, etc., or combinations thereof. In some implementations, the force translation arms 115 can be an element reinforced with a rigid material. For example, the force translation arms 115 can have an inner, rigid element such as silicone elastomer, polyurethane, PMMA, PVDF, PDMS, polyamide, polyimide, polypropylene, polycarbonate, etc. that is covered by a softer material such as silicone elastomer, polyurethane, or flexible acrylic materials that are hydrophobic or hydrophilic. In some implementations, the force translation arms 115 can include an inner, rigid element that extends between the outer contact portion 135 to the inner contact portion 137. In other implementations, the inner, rigid element extends only along a partial length of the force translation arms 115 between the outer portion 135 and the inner portion 137. For example, the inner, rigid element need not extend clear to the outer contact portion 135 where the force translation arms 115 make contact with the ciliary structures to provide a softer and atraumatic surface so as not to damage the ciliary structures. The inner, rigid element also need not extend clear to the inner contact portion 137 such that upon inward movement of the shape deformation membrane 140 by the force translation arm 115, the inner, rigid element of the force translation arm 115 remains outside the lens body 105. Generally, the force translation arms 115 are formed of a material and/or sized in a manner that they maintain their shape when forces are applied to them by a ciliary structure and they do not collapse or deform upon transferring that force to move the shape deformation membrane 140. As described above, movement of the shape deformation membrane 140 causes a shape change in the sealed chamber 155, which changes the shape of the optical fluid filling the sealed chamber 155. When the optical fluid presses against the inner surfaces of the lens body 105 it causes an outward bowing in the dynamic membrane 143 of the anterior optic 145. This outward bowing results in a more spherical or convex lens body 105 shape thereby increasing the power of the lens suitable for near vision focus.

The number of force translation arms 115 and shape deformation membrane 140 can vary. The AIOL 100 can include two force translation arms 115 positioned on opposing sides of the device lying adjacent to two shape deformation membrane 140, as shown in FIGS. 2A-2F. Alternatively, the AIOL 100 can include a single force translation arm 115 movable in a manner sufficient to change the shape of the dynamic membrane 143 of the anterior optic 145 to achieve a desired dioptric change. The AIOL 100 can also include more than two arms, such as three, four, or more force translation arms 115 distributed around the lens body 105. The force translation arms 115 can be distributed in a symmetric manner around the perimeter of the AIOL 100 or in an asymmetric manner. It should be appreciated that the number of force translation arms 115 need not match the number of shape deformation membranes 140. For example, the AIOL 100 can include a single shape deformation membrane 140 extending along an arc length of the equator region 108 of the annular element 104 and more than one force translation arms 115 configured to make contact with or coupled to different regions of the single shape deformation membrane 140.

The AIOL 100 can also include a stabilization system 120. The stabilization system 120 can be configured to maintain alignment of the optics of the device and resist movement of the device once the device is implanted and undergoing shape changes. Unlike the force translation arms 115, the stabilization system 120 does not cause accommodation of the AIOL 100. And because the force translation arms 115 are independent from the stabilization system 120 and are not necessary to fix, center, stabilize, and/or hold the AIOL 100 in position within the eye, the AIOLs 100 described herein can incorporate a single, asymmetric force translation arm 115 sufficient to provide the dioptric change of the dynamic membrane.

The stabilization system 120 can be coupled to a perimeter region of the device 100, for example, bonded, coupled, or molded as part of the lens body 105 or to an exterior support, if present. In some implementations, the stabilization system 120 can be coupled to a posterior region of the device 100 such that it can provide stabilization and engagement with a portion of the capsular bag, such as with the anterior capsule.

The stabilization system 120 can vary. In some implementations, the stabilization system 120 includes one or more of a stabilization haptic, static haptic, ring-like element, a flange element, or other stabilizing feature. In some implementations, the stabilization system 120 can include a ring-like structure 171 having a flange 172 extending outward from a region of the ring-like structure 171, such as the posterior end (see, for example, FIGS. 7A-7C, FIGS. 11A-11L, FIGS. 14A-14H, FIGS. 15A-15C, and FIGS. 16A-16F). An anterior end of the ring-like structure 171 can be coupled to the peripheral connecting ring 153 of the static element 150 such that the flange 172 on its posterior end extends posterior to the lens body 105. For example, an outer diameter of the ring-like structure 171 can be sized to be received within an inner diameter of the peripheral connecting ring 153 of the static element 150. It should be appreciated, however, that other coupling arrangements between the stabilization system 120 and the lens body 105 are considered herein. The ring-like structure 171 and flange 172 can be coupled to or integral with other portions of the lens body 105 such as the annular element 104 or the annular internal support and need not be coupled to the static element 150. Generally, the coupling of the stabilization system 120 to the lens body 105 is such that the flange 172 is positioned in a posterior position relative to the lens body 105 and to the force translation arms 115 along the optical axis A of the lens 100. Additionally, the stabilization system 120 and its components such as the flange 172 are coupled to the lens body 105 in a manner that does not interfere with movement of the force translation arms 115 and the shape deformation membrane 140. For example, as shown in FIG. 7A, FIG. 11A, FIG. 14A, FIG. 15A, and FIG. 16A, the stabilization ring 171 can include a pair of flanges 172 that extend outward from the periphery of the lens body 105 between the location of the force translation arms 115. In some implementations, the flanges 172 can have an outer elevation, but because they are positioned 90 degrees relative to the force translation arms 115 that can provide stability without interfering with accommodative movements of the arms 115. Forces applied to the flange 172 or the ring-like structure 171 do not get transferred by the stabilization system 120 to the lens 100 in a manner that causes deformation of the sealed chamber 155 or shape change in the dynamic membrane 143. The flange 172 can be positioned in a posterior position relative to the lens body 105 and to the force translation arm 115. An anterior surface of the flange 172 may also be on the same plane as the force translation arm 115. The more anterior the flange 172, the greater the flange 172 can pull the lens body 105 in a posterior direction.

Figure 14I:
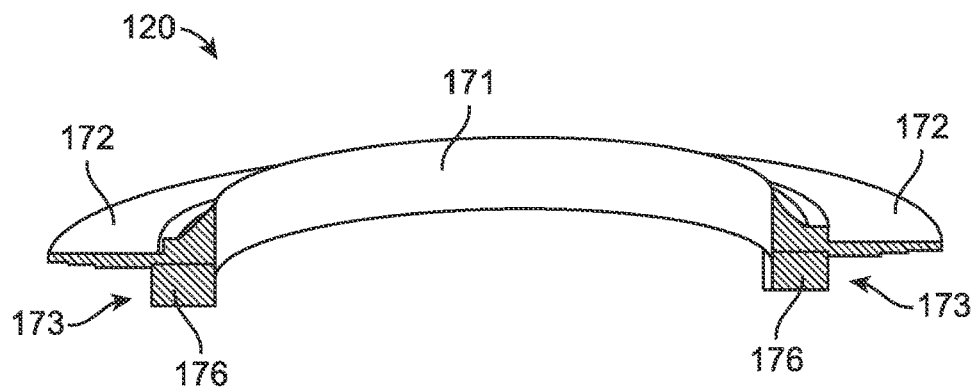
FIG. 14I illustrates a cross-sectional, perspective view of an implementation of a stabilization system.
Figure 15A:
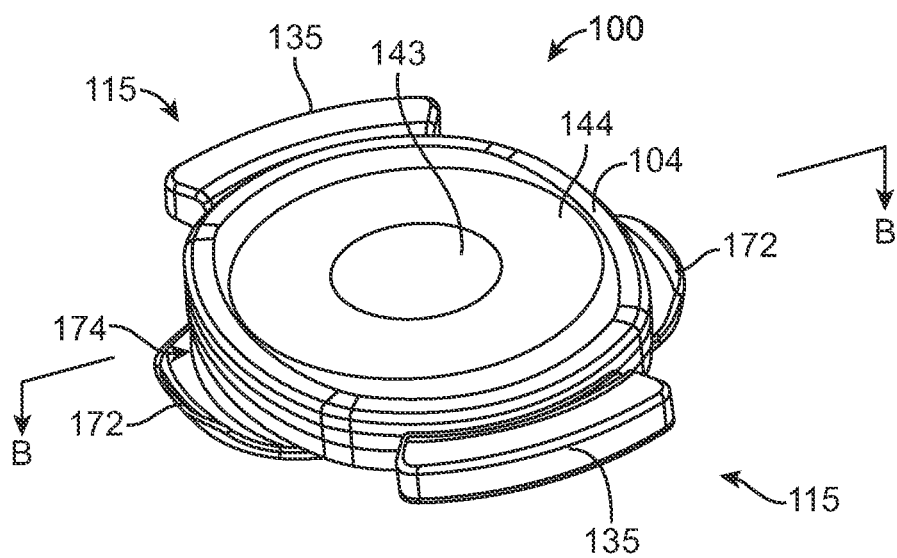
FIG. 15A illustrates a perspective view of an implementation of an accommodating intraocular lens device having a stabilization system.
Figure 15B:
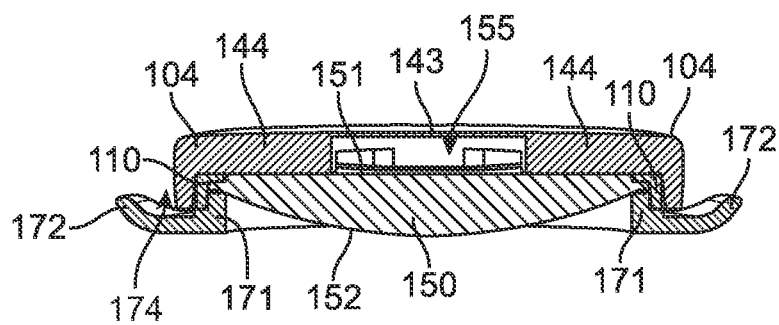
FIG. 15B is a cross-sectional view taken along line B-B of FIG. 15A.
Figure 15C:
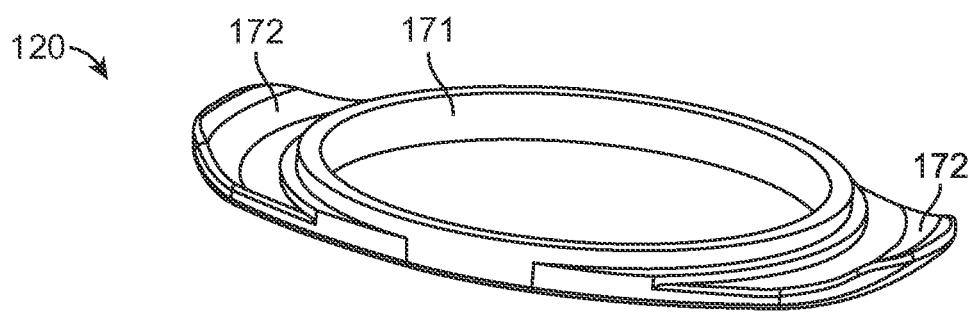
FIG. 15C is the stabilization system of the device of FIG. 15A.

The stabilization system 120 can further include a ring 173 protruding from its posterior surface. For example, the ring 173 can extend from a posterior surface of the ring-like structure 171 having the flange 172. The ring 173 can have a narrow, generally square edge 176 (see FIG. 14I). The ring 173 of the stabilization system 120 can be positioned relative to the lens 100 such that it can be positioned within the capsular bag 22. The ring 173 can have an inner diameter that is about 5 mm and an outer diameter that is about 6 mm thereby creating an approximately 1 mm flat posterior surface. The ring 173 can have a height this is between about 50 μm-about 700 μm. As such, the edge 176 of the ring 173 is generally square- or rectangular-shaped. The edge 176 of the ring 173 can create a 360 degree surface for contact against the posterior capsule. The edge 176 of the ring 173 can provide a barrier to lens epithelial cell migration towards the central posterior capsule that contributes to posterior capsule opacification (PCO). The edge 176 of the ring 173 can have other shapes besides square, however, the edge 176 provides a relatively sharp contact site between the lens 100 and the posterior capsular to prevent issues with PCO.

It should be appreciated that other portions of the lens 100 such as the lens body 105, the static element 150, or other region of the stabilization system 120 can incorporate a similar edge to engage the posterior capsule in such a way to minimize the risk of PCO. Additionally, a combination of features may be used to promote fluid flow in the capsular bag and around the lens in order to maintain a healthy capsular environment with limited PCO. For example, the stabilization system 120 may engage the lens equator while the static element 150 and lens body 105 engage the anterior and posterior capsule to prevent the collapsing of the capsular walls. In another embodiment, stabilization system 120 can be configured to engage multiple capsular surfaces, thereby keeping the capsule open without assistance from other lens components.

The ring-like structure 171 of the stabilization system 120 can be generally cylindrical in shape and the flange 172 can have a generally oval or elliptical outer dimension such that the flange 172 extends out beyond the outer diameter of the ring-like structure 171 in at least two regions along the perimeter of the lens body 105. The anterior end of the ring-like structure 171 can be coupled to the peripheral connecting ring 153 of the static element 150 and the flange 172 can be dimensioned to remain outside the lens body 105 on a posterior end and extends out beyond the outer diameter of the lens body 105 at the at least two regions. The at least two regions where the flange 172 extends out beyond the outer diameter of the lens body 105 can be oriented relative to the lens body 105 such that the flange 172 provides stabilization support relative to the force translation arms 115. For example, if the lens 100 includes a pair of opposing force translation arms 115, the flange 172 can be arranged relative to the lens body 105 such that the flange 172 extends outward from the lens body 105 between the location of the opposing force translation arms 115 (see, for example, FIG. 7A, FIGS. 11A-11B, FIGS. 14A-14C, FIGS. 15A-15C, and FIG. 16A). It should be appreciated that the flange 172 can have other shapes besides oval and elliptical. For example, the flange 172 can also be cylindrical and have an outer diameter configured to extend outward beyond the outer diameter of the ring-like structure 171 and the lens body 105 along 360 degrees. Alternatively, the flange 172 can have more than two locations where it extends beyond the outer diameter of the lens body 105 such as three, four, five, or more locations. The ring-like structure 171 and the flange 172 can provide 360 degree support and stabilization to the lens 100.

As mentioned above, the ring-like structure 171 can incorporate a pair of flanges 172 that are positioned between or rotated 90 degrees relative to the location of the force translation arms 115. An outermost edge of the flanges 172 can project anteriorly such that a channel or groove 174 is formed near an inner region of the flange 172, for example between the posterior surface of the annular element 104 and an anterior surface of the flange 172 (see FIGS. 15A-15C and 16A-16B). When the ring-like structure 171 is positioned within the capsular bag, this outer elevation of the flanges 172 can engage with a posterior-facing internal surface of the capsular bag to help urge the lens 100 in a posterior direction relative to the bag. Additionally, the edge of the capsulorhexis can be received and held within the groove 174. In some implementations, the edge can be captured between the groove 174 of the flange 172 and a posterior-facing edge of the annular element 104.

As described elsewhere herein, the force translation arms 115 are configured to extend outside the capsular bag 22 to engage with ciliary structures such that the physiological forces from ciliary muscle contraction can cause a change in optical power of the lens in a manner that is independent of the capsular mechanism or movement of the capsular bag 22. The flange 172 extending outward from a posterior end region 107 of the annular element 104 can remain inside the capsular bag 22 while the force translation arms 115 extending generally from the equator region 108 or anterior end region of the annular element 104 extend outside the capsular bag 22 to engage with the ciliary structures. The flange 172 can be arranged to engage the posterior-facing surface of the edge of the capsular bag 22 formed by the anterior capsulorhexis C to improve the fixation of the lens 100 within the eye. The edge of the capsular bag 22 formed by the capsulorhexis C can be received within a groove 174 formed between the posterior surface of the annular element 104 and an anterior surface of the flange 172 (see FIG. 7B and also FIGS. 14D-14G). The capsulorhexis C can thus, aid in fixing the lens position.

The flange 172 can have interruptions providing for flexibility during handling as well as allow the surgeon to access portions of the lens 100 and capsular bag 22 posterior to the flange 172. This may be preferred in case the surgeon needs to clean the capsular bag, remove viscoelastic, adjust the position of the lens, or any other procedure in which the surgeon uses a tool to manipulate the environment posterior to the AIOL. In some implementations, the interruptions can include one or more apertures 175 extending through a region of the flange 172 (see FIG. 11A, and also FIGS. 16A, 16D). The interruptions can also include one or more indentations 178 or grooves or other feature at an outer perimeter of the flange 172 (see FIGS. 14A-14H). The indentations 178 can allow for easy insertion into the eye as well as allow for withdrawal of viscoelastic from inside the capsular bag 22 using a cannula or other tool known in the art.

Because the shape deformation membrane 140 is sensitive to small forces imparted by the ciliary structures via the force translation arms 115, implantation of the posterior end region of the lens 100 within the anterior capsular fragment can result in inadvertent contact between the edge of the capsulorhexis C and the shape deformation membrane 140. Such contact can cause power changes with undesirable optical consequences. Thus, the stabilization system 120 can stabilize the lens position within the eye as well as protect the shape deformation membrane 140 from coming into contact with the edge of the capsulorhexis C. Generally upon implantation, a plane of the capsulorhexis C will intersect a plane of the shape deformation membrane 140. At least a portion of the stabilization system 120 can be designed to extend between where the shape deformation membrane 140 and the capsulorhexis C edge intersect. Thus, the portion of the stabilization system 120 providing a surface for the capsulorhexis C edge to contact thereby preventing the edge from contacting with the shape deformation membrane 140 to cause optical or accommodative changes in the AIOL 100.

Figure 12:
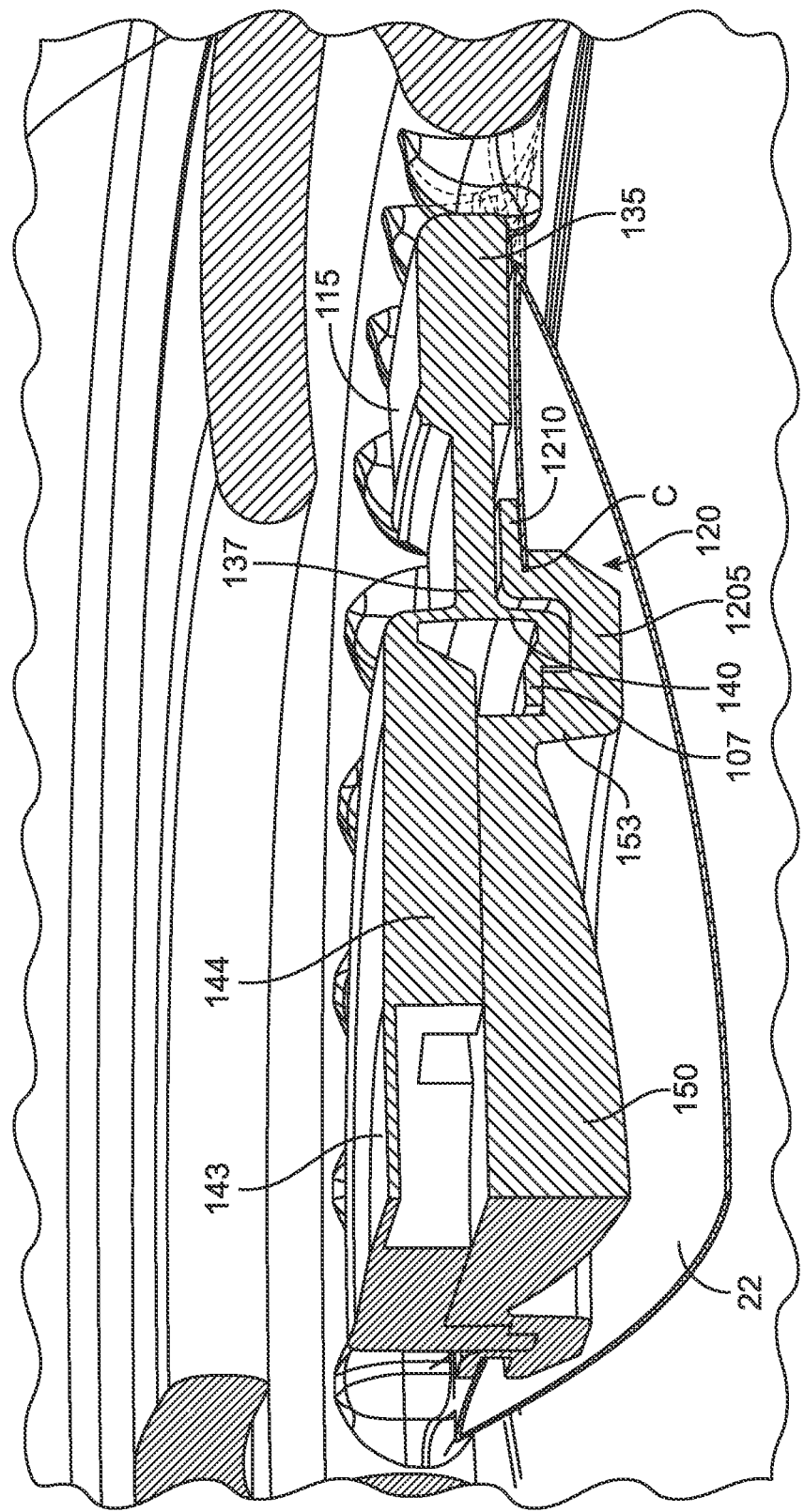
FIG. 12 illustrates a cross-sectional, partial perspective view of an accommodating intraocular lens device positioned within the eye and having a stabilization system preventing contact between the capsular bag and the shape deformation membrane.

FIG. 12 illustrates an implementation of a stabilization system 120 that prevents contact between the edge of the capsulorhexis C and the shape deformation membrane 140. The stabilization system 120 can be positioned near a posterior region of the lens body 105. The stabilization system 120 can include a shield 1205 having a protective rim 1210 positioned at its outermost terminus. It should be appreciated that the actual shape and configuration of the shield 1205 and rim 1210 can vary. The shield 1205 can be a generally annular-shaped element configured to be positioned external the lens body 105. The shield 1205 can couple to an outer perimeter of a posterior side of the lens body 105. The shield 1205 can be coupled to or otherwise extend from the peripheral connecting ring 153 of the static element 150 over the posterior region 107 of the annular element 104 and at least a portion of the equator region 108 of the annular element 104. Thus, the shield 1205 forms an annular cap of the peripheral region on the posterior-facing surface of the lens body 105 as well as at least a portion of the equator region 108 of the annular element 104. Because the shape deformation membrane 140 extends along an arc length of the equator region 108 of the annular element, the shield 1205 covers at least a portion of the shape deformation membrane 140 as well. The protective rim 1210 can extend outward from a region of the shield 1205 (the region where the shield 1205 covers the portion of the shape deformation membrane 140) thereby forming an angle relative to that region of the shield 1205. The region of the shield 1205 covering the portion of the shape deformation membrane 140 can align generally parallel with the shape deformation membrane 140 such that it covers, but avoids contact the shape deformation membrane 140. The protective rim 1210 can have a width such that it extends along a least a length of the underneath surface (or posterior-facing surface) of the force translation arms 115 near its inner, contact region 137 where it abuts or is coupled to the shape deformation membrane 140. The protective rim 1210 can extend generally parallel with the length of the force translation arms 115 along which it extends such that the protective rim 1210 forms an approximate 90 degree angle relative to where it extends outward from the shield 1205. The width of the protective rim 1210 can vary and thus, the length it extends under the force translation arms 115 can vary. Generally, the width of the protective rim 1210 along with the shield 1205 from which it extends is sufficient to engage a portion of the anterior surface of the capsular bag 22 such that the edge of the capsulorhexis C sits within the region where the protective rim 1210 and the shield 1205 meet. This prevents contact between the shape deformation membrane 140 and the edge of the capsulorhexis C. It should be appreciated, that the stabilization system 120 can include a combination of the protective rim 1210 and one or more flanges 172 as described above. Thus, the stabilization system 120 can have one or more components configured to remain outside the capsular bag 22 (e.g. the protective rim 1210) such that the component extends over an edge of the capsulorhexis C and the stabilization system 120 can have one or more components configured to remain inside the capsular bag 22 (e.g. the flange 172 or a stabilization haptic) such that the edge of the capsulorhexis C extends over the component.

Figure 17A:
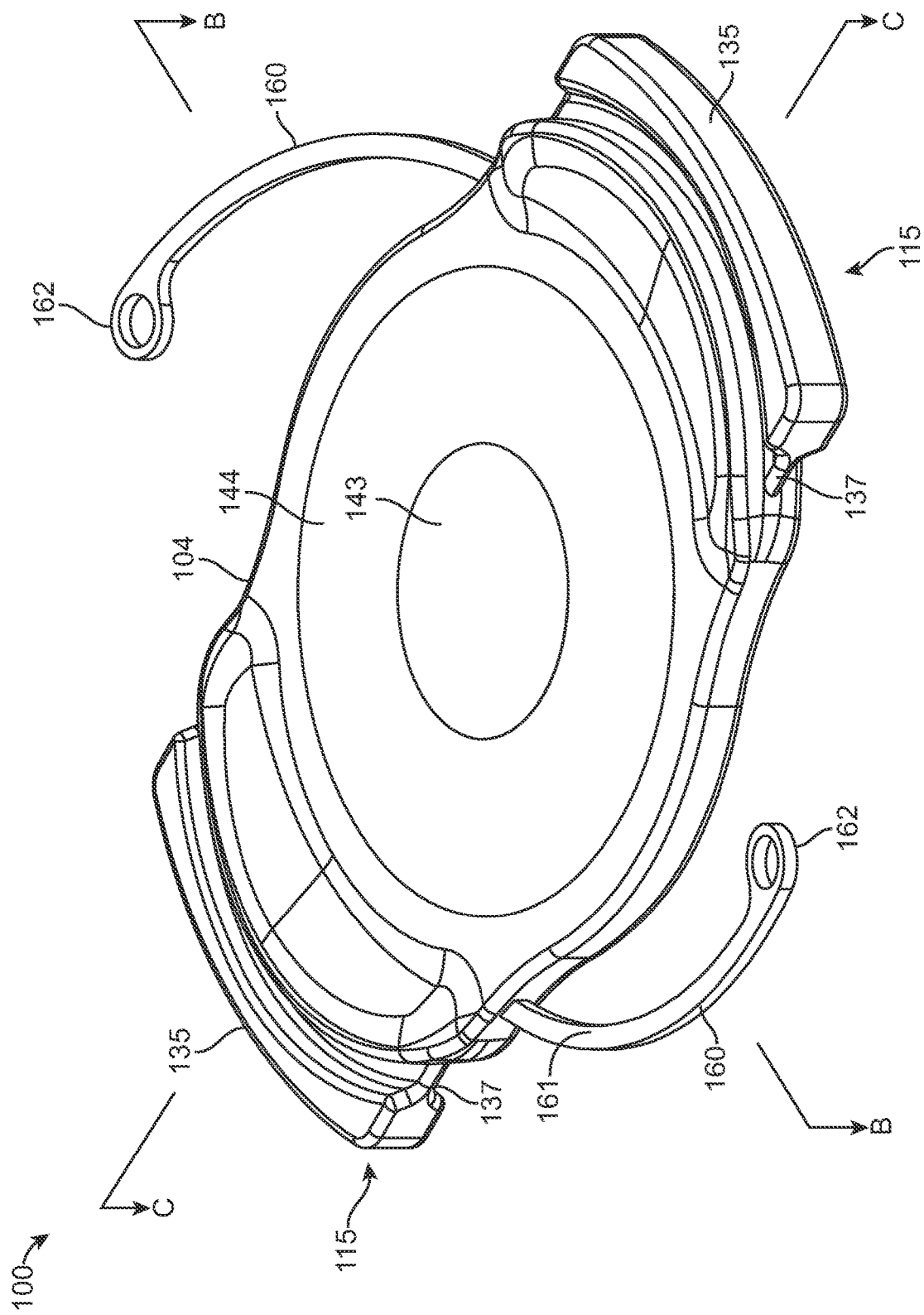
FIG. 17A illustrates a perspective view of an implementation of an accommodating intraocular lens device having a stabilization system.
Figure 17B:
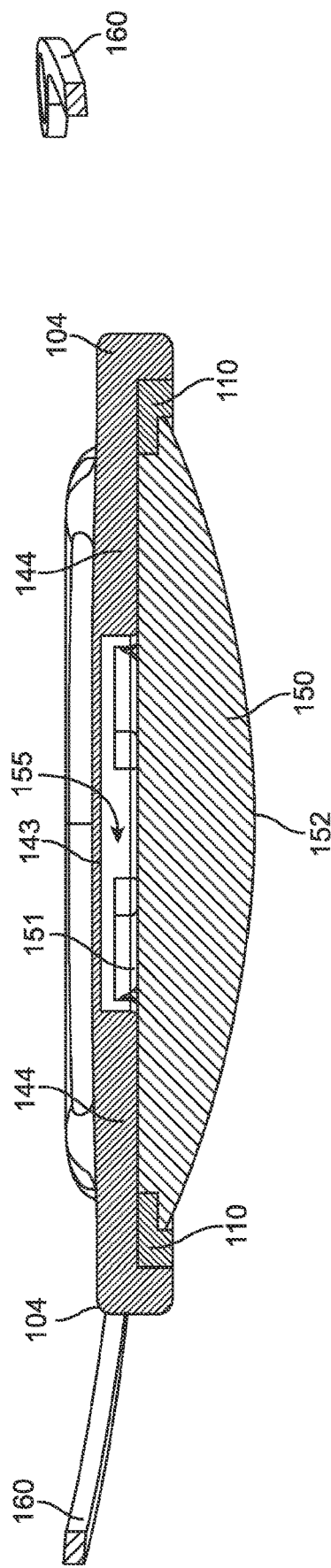
FIG. 17B is a cross-sectional view taken along line B-B of FIG. 17A.
Figure 17C:
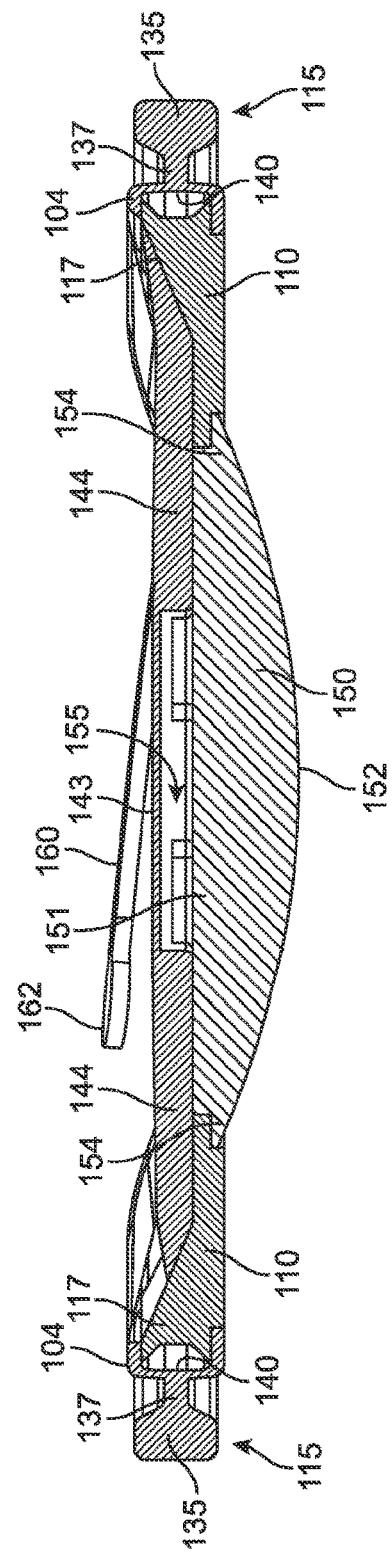
FIG. 17C is a cross-sectional view taken along line C-C of FIG. 17A.
Figure 19A:
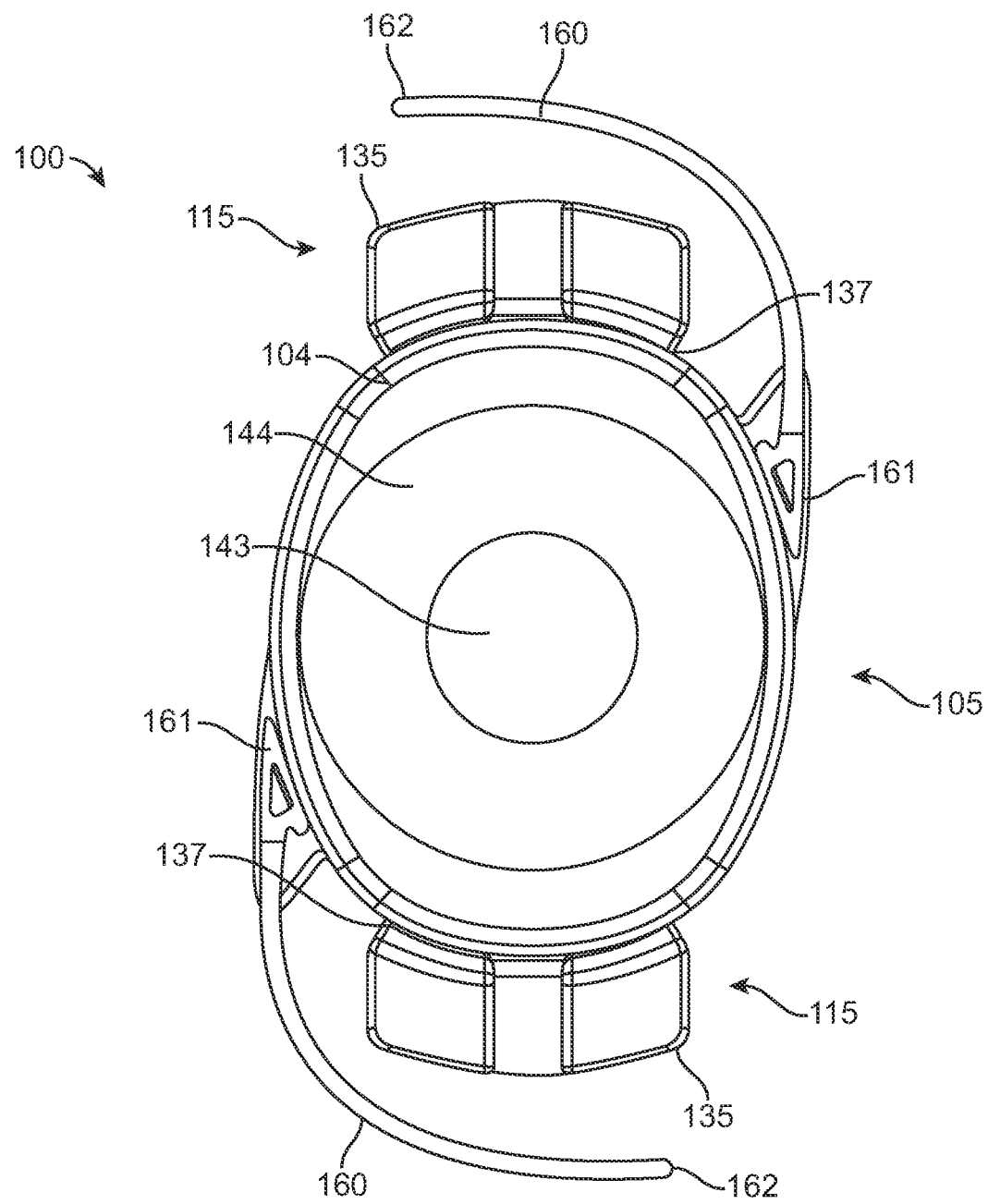
FIG. 19A illustrates a top view of an implementation of an accommodating intraocular lens device having a stabilization system.
Figure 19C:
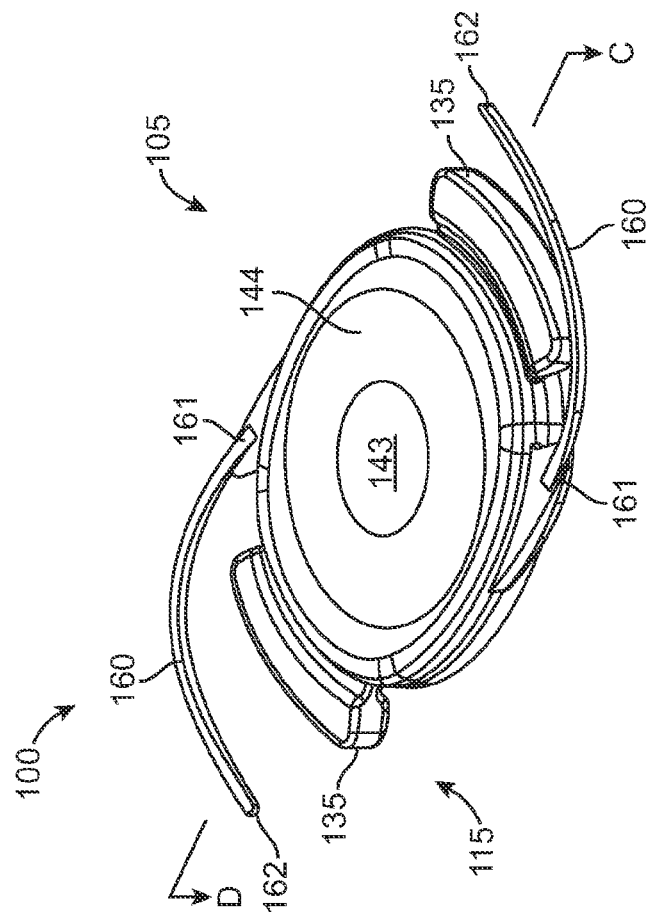
FIG. 19C illustrates a perspective view of the device of FIG. 19B.
Figure 19B:
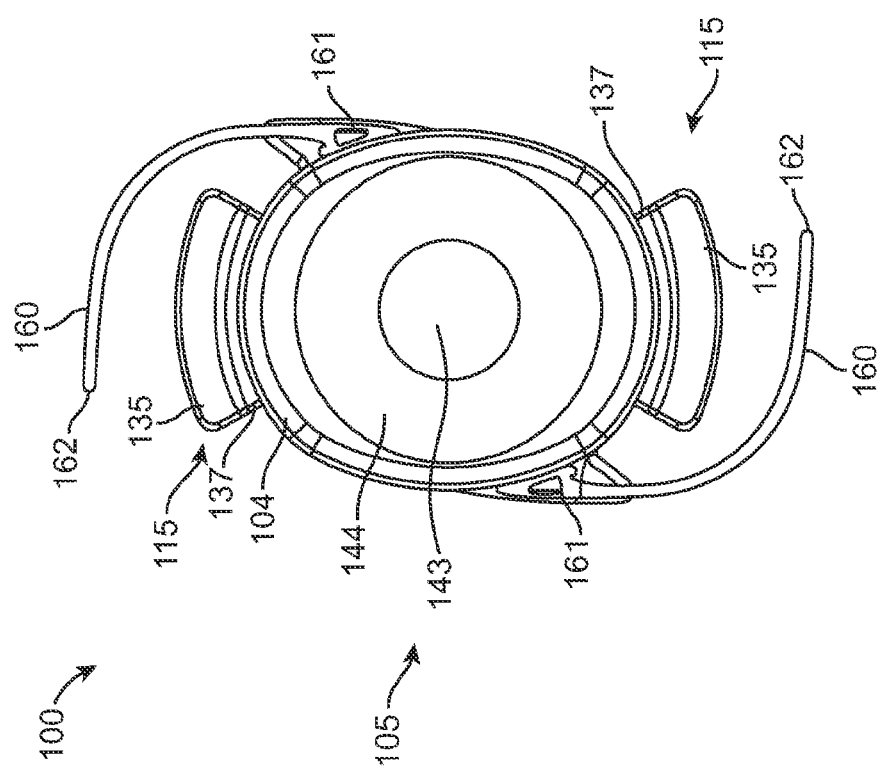
FIG. 19B illustrates a top view of an implementation of an accommodating intraocular lens device having a stabilization system.
Figure 19D:
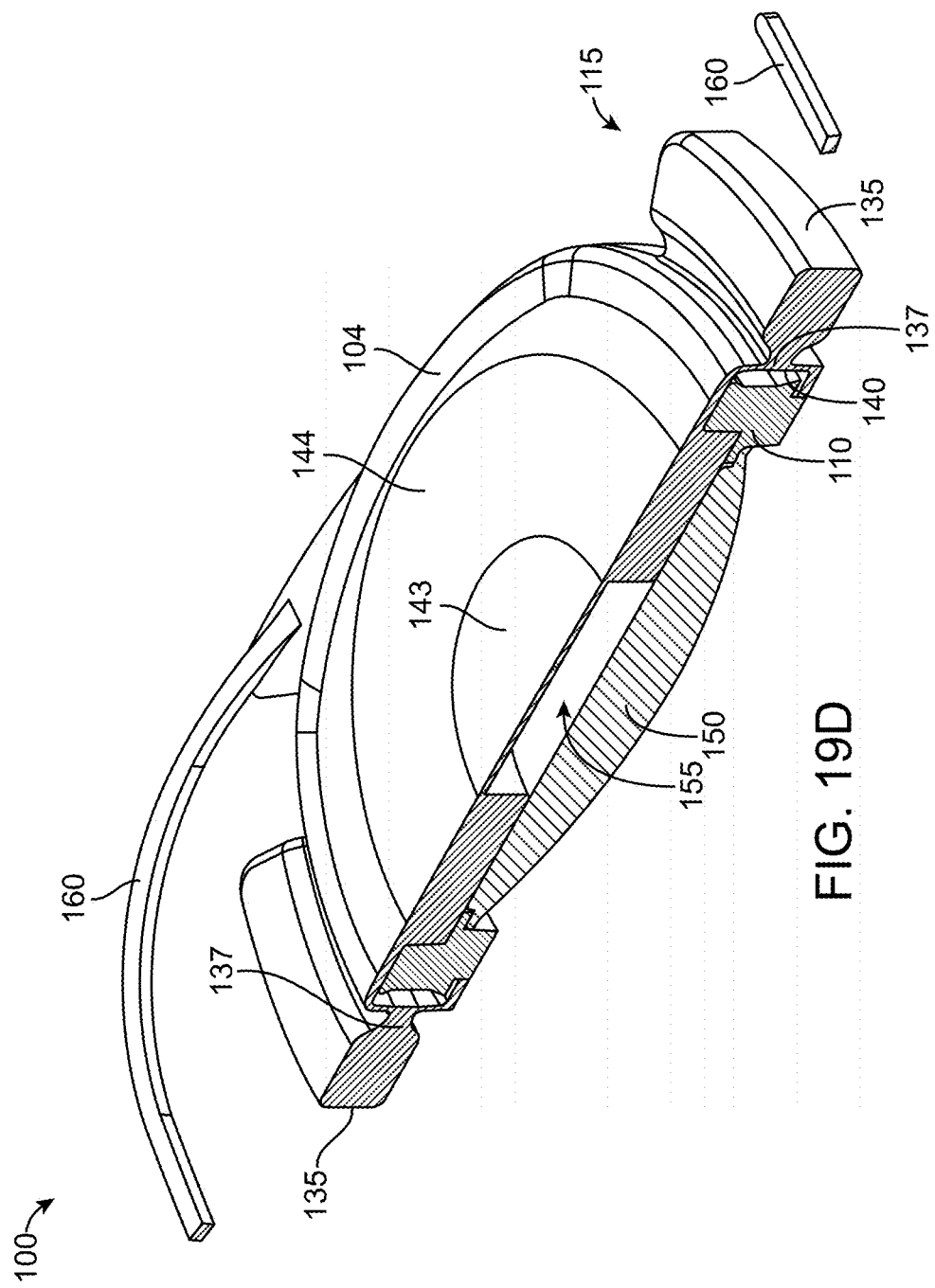
FIG. 19D is a cross-sectional view taken along line D-D of FIG. 19C.

In some implementations, the stabilization system 120 includes one or more stabilization haptics 160 (see, for example, FIGS. 2B-2F, FIGS. 17A-17F, FIGS. 19A-19E). The stabilization haptics 160 can be coupled to or integral with the annular element 104 of the lens body 105 away from the location of the at least one shape deformation membrane 140 or in a manner that does not interfere with movement of the shape deformation membrane 140. For example, the AIOL 100 can include two, opposing shape deformation membranes 140 and the stabilization system 120 can incorporate a pair of stabilization haptics 160 positioned on or coupled to the annular element 104 at a location that is between the two shape deformation membranes 140. As such, forces applied to the haptics 160 of the stabilization system 120 upon implantation are not transferred by the stabilization system 120 to the AIOL 100 in a manner that causes deformation of the sealed chamber 155 or shape change in the dynamic membrane 143. The internal portion 161 of the haptics 160 can be coupled to or integral with the annular element 104 such that the haptics 160 extend from the equator region 108 of the annular element 104 between the anterior end region and the posterior end region 107 of the annular element 104. Alternatively, the internal portion 161 of the haptics 160 can be coupled to or integral with a region of the annular element 104 located more anteriorly or more posteriorly along the optical axis of the AIOL such as shown in FIG. 2C. Alternatively, the haptics 160 can be connected to or integrated with the static element 150 as described above. In some implementations, the haptics 160 are positioned relative to the lens body 105 such that they extend outward from the lens body 105 at a location that is generally more posteriorly oriented than the force translation arms 115 (see FIG. 2A). In this implementation, the one or more of the stabilization haptics 160 can be positioned and engaged within the capsular bag 22 to maintain the stability of the device 100 during motion of the force translation arms 115 to prevent and/or limit anterior, posterior, rotational movements of the device. In other implementations, the haptics 160 are positioned relative to the lens body 105 such that they extend outward from the lens body 105 at a location that is generally more anteriorly oriented than the force translation arms 115 (see FIGS. 17A and 19C). In this implementation, the one or more stabilization haptics 160 can be positioned and engaged within the ciliary sulcus to maintain the stability of the device 100 during motion of the force translation arms 115 to prevent and/or limit anterior and rotation movements of the device. In some implementations, each of the stabilization haptics 160 is arranged relative to the force translation arms 115 such that an internal region 161 of the haptic 160 is coupled near a first side of a first force translation arm 115 and its terminal end 162 extends around a circumference of the AIOL 100 away from the first side of the first force translation arm 115 towards the other force translation arm 115 (see FIG. 17A). In other implementations, each of the stabilization haptics 160 is arranged relative to the force translation arms 115 such that an internal region 161 is coupled near a first side of a first force translation arm 115 and its terminal end 162 extends over the force translation arm 115 from the first side towards an opposite site of the same force translation arm 115 (see FIG. 19A). An AIOL 100 having the terminal ends 162 positioned such that they extend over the force translation arms 115 reduces the width of the AIOL 100 providing for easier insertion and manipulation of the AIOL 100 into position in the eye. In either implementation, the stabilization haptics 160 can be angled anteriorly relative to the plane of the force translation arms 115 such that their terminal ends 162 can engage the ciliary sulcus when the AIOL 100 is positioned, at least in part, within the capsular bag. The stabilization haptics 160 can then urge the AIOL 100 in a posterior direction further into the capsular bag. Regardless whether the terminal ends 162 of the stabilization haptics 160 extend over or within the same quadrant as the force translation arms 115 or between the force translation arms 115, the haptics 160 aid in preventing the force translation arms 115 from coming into contact with the iris by applying posterior-directing pressure on the AIOL 100.

Each haptic 160 can loop around along a curve such that the haptic 160 is configured to engage eye tissue along a greater portion of their overall length. The haptics 160 can be coaxial or coplanar with the force translation arms 115. The haptics 160 can also be positioned along a different axis than the force translation arms 115, for example, offset from the force translation arms 115 or angulated relative to the force translation arms 115. In some implementations, the haptics 160 can be positioned at an angle in the range of 0-20 degrees or other degree angle relative to the force translation arms 115. Each haptic 160 can angle away from a plane of the AIOL such that a terminal end 162 of each haptic 160 sits on a different plane than the internal region 161 of the haptic 160 near where it couples to the annular element 104. For example, FIGS. 2B-2D shows an implementation of an AIOL having two haptics 160 and two opposing force translation arms 115. The force translation arms 115 in this implementation are coupled generally centrally relative to the annular element 104 of the lens body 105 such that each of the force translation arms 115 between inner contact portion 137 and outer contact portion 135 are disposed generally along a central plane of the AIOL. Each of the two haptics 160 in this implementation is coupled to a region of the annular element 104 between the two force translation arms 115. The internal region 161 of each haptic 160 is positioned or coupled to the annular element 104 at a location that is slightly posterior to the central plane of the annular element 104 between anterior and posterior surfaces. Each haptic 160 curves from the internal region 161 towards the terminal end 162 such that the terminal end 162 of each haptic 160 is positioned on a plane that is posterior to a plane of the internal region 161 of the haptic 160. This results in the contact portion 135 of the force translation arms 115 arranged more anteriorly compared to the terminal end 162 of the haptics 160 such that they can be implanted in different anatomical locations within the eye. For example, the contact portions 135 of the force translation arms 115 can be positioned in the eye such that they make contact with the ciliary body apex 18 or the ciliary sulcus and the haptics 160 can extend more posteriorly than the force translation arms 115, for example, into the capsular bag 22. It should be appreciated, however, that the one or more haptics 160 can be positioned in the same plane as the force translation arms 115. Alternatively, the haptics 160 can be angled anteriorly in an effort to bias the lens in a posterior position (see FIGS. 17A-17F and 19C). In order to minimize contact with the iris, the haptics 160 can be used to hold lens body 105 and force translation arms 115 posterior relative to terminal end 162 which may be placed in the sulcus or capsular bag.

Any of the stabilization systems described herein can be arranged to be coaxial or coplanar with the force translation arms 115 or positioned along a different axis than the force translation arms 115 such that the stabilization system 120 is offset from the force translation arms 115 or angled relative to them as described above with respect to the haptics 160. Similarly, the stabilization systems 120 can be angled relative to the force translation arms 115 such that at least a portion of the stabilization system 120 angles away from a plane of the AIOL such that at least a portion of the stabilization system sits on a different plane than another portion of the stabilization system.

It should be appreciated that any of the stabilization systems described herein can be formed from silicone elastomer, polyurethane, PMMA, PVDF, PDMS, polyamide, polyimide, polypropylene, polycarbonate, or flexible acrylic materials that are hydrophobic or hydrophilic or any combination of those materials. The stabilization system may have a softer body that is reinforced with more rigid structures in order to provide its stabilizing function while maintaining flexibility for insertion and manipulation.

One or more portions of the stabilization system 120 described herein can incorporate biting elements to improve fixation within the eye. In some implementations, the stabilization system 120 includes haptics 160 and the biting elements can be positioned near their terminal ends 162 to improve fixation of the haptic 160 within the eye. The haptics 160 can be any of a variety of haptic designs or combination of haptic designs including, but not limited to open-loop, closed-loop, plate-style, plate loop, monoblock-plate style, j-loop, c-loop, modified J-loop, multi-piece, single-piece, angulated, planar, offset, etc. Haptics 160 considered herein can include the Rayner designed haptics (Rayner Intraocular Lenses Ltd, East Sussex, UK), NuLens designed haptics (NuLens Ltd., Israel), Staar lens designs (Staar Surgical, Monrovia, Calif.), and others. In some implementations, the stabilization system 120 whether including one or more haptics 160 or a 360 degree flange 172 can be formed of a biocompatible polymer such as silicone, polyurethane, PMMA, PVDF, PDMS, polyamide, polyimide, polypropylene, polycarbonate, PEEK, etc. or a combination of such materials. The stabilization system 120 can be formed of a material or configured to be foldable. In some implementations, the stabilization system 120 is formed of a shape memory material.

The AIOLs described herein have improved mechanical stability, internally and/or externally, that results in a more efficient shape change. The shape change is more efficient in that it occurs only where desired (i.e. at the shape deformation membrane 140 and the dynamic membrane 143) without causing distortion or bulging elsewhere in the device that would take away from the desired shape change. The efficiency in shape change is due, in part, to the mechanical isolation of the moving parts. As will be described in more detail below, the one or more internal supports 110 provide enough rigidity to the AIOL 100 to mechanically isolate the moving parts to effectively and efficiently implement the shape change without inadvertent bulging or distortion in other parts of the device. The inner-facing region of the AIOLs 100 described herein can have reduced angles, rounded edges, and fewer dead zones improving the efficiency of the shape change achieved.

Figure 16A:
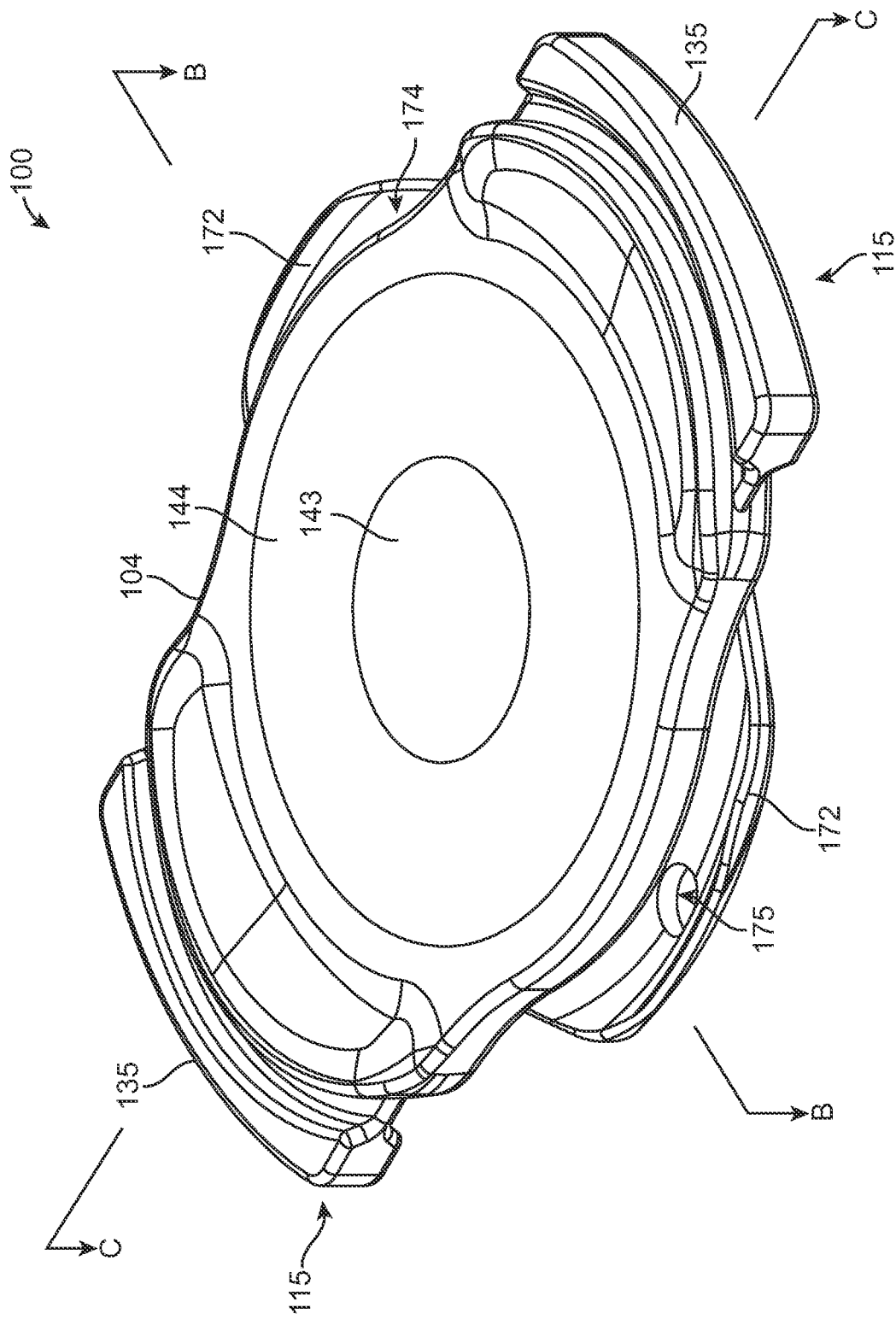
FIG. 16A illustrates a perspective view of an implementation of an accommodating intraocular lens device having a stabilization system.
Figure 16B:
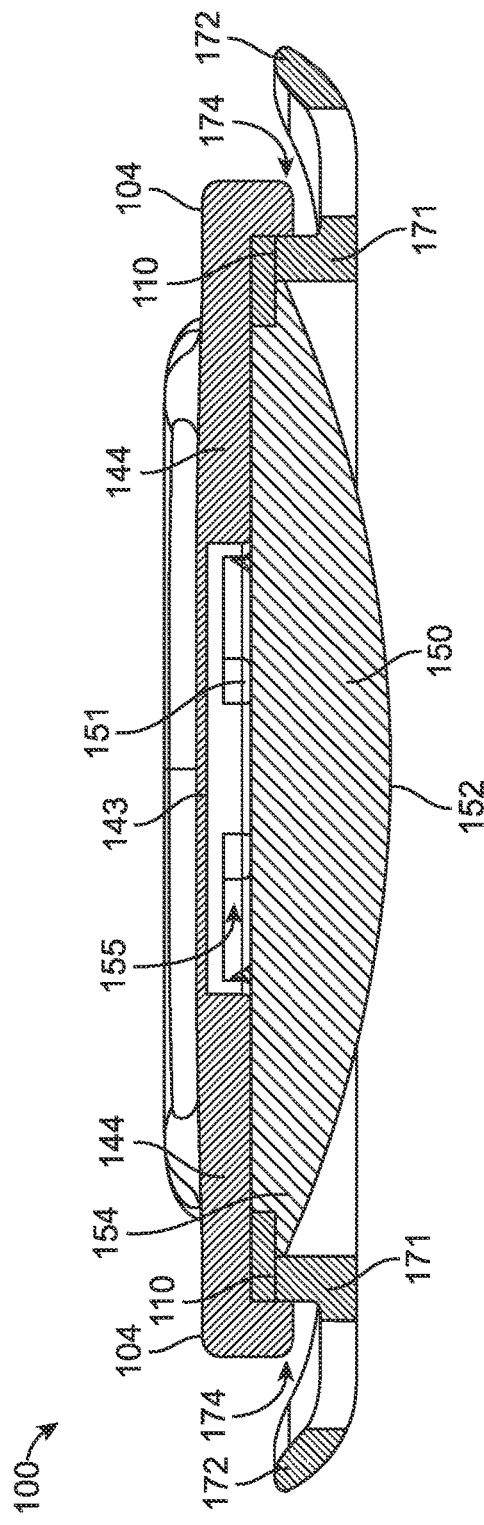
FIG. 16B is a cross-sectional view taken along line B-B of FIG. 16A.
Figure 16C:
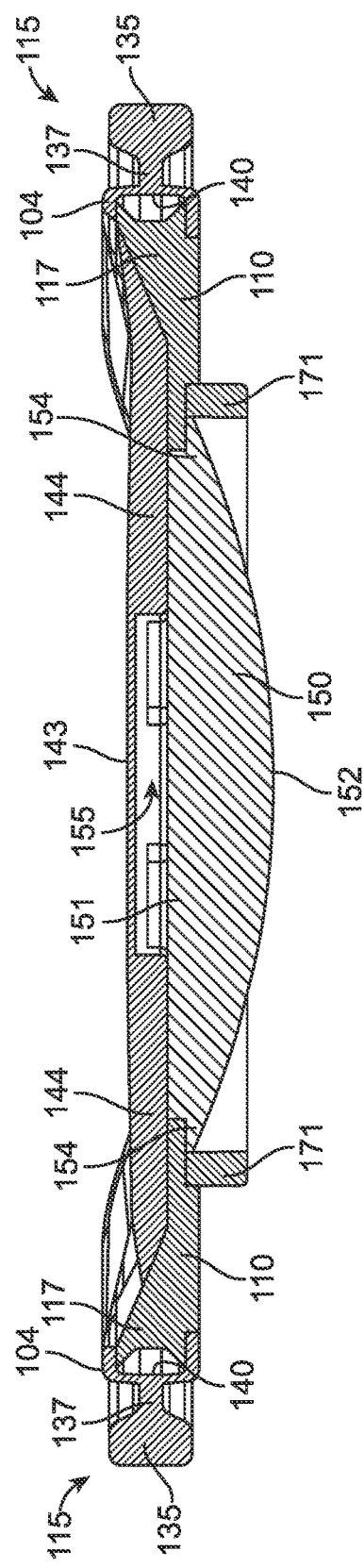
FIG. 16C is a cross-sectional view taken along line C-C of FIG. 16A.
Figure 17D:
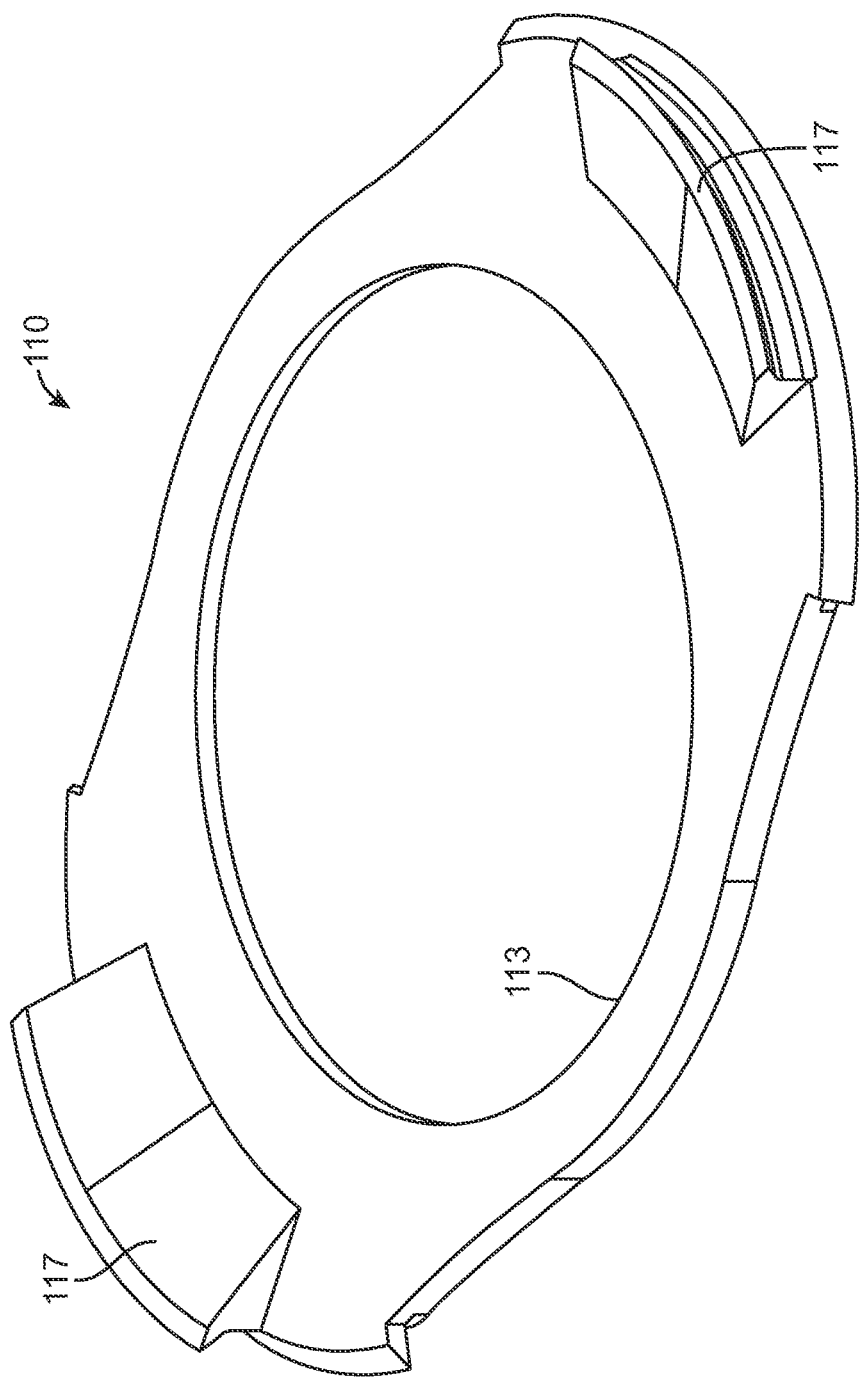
FIG. 17D is the internal support of the device of FIG. 17A.
Figure 19E:
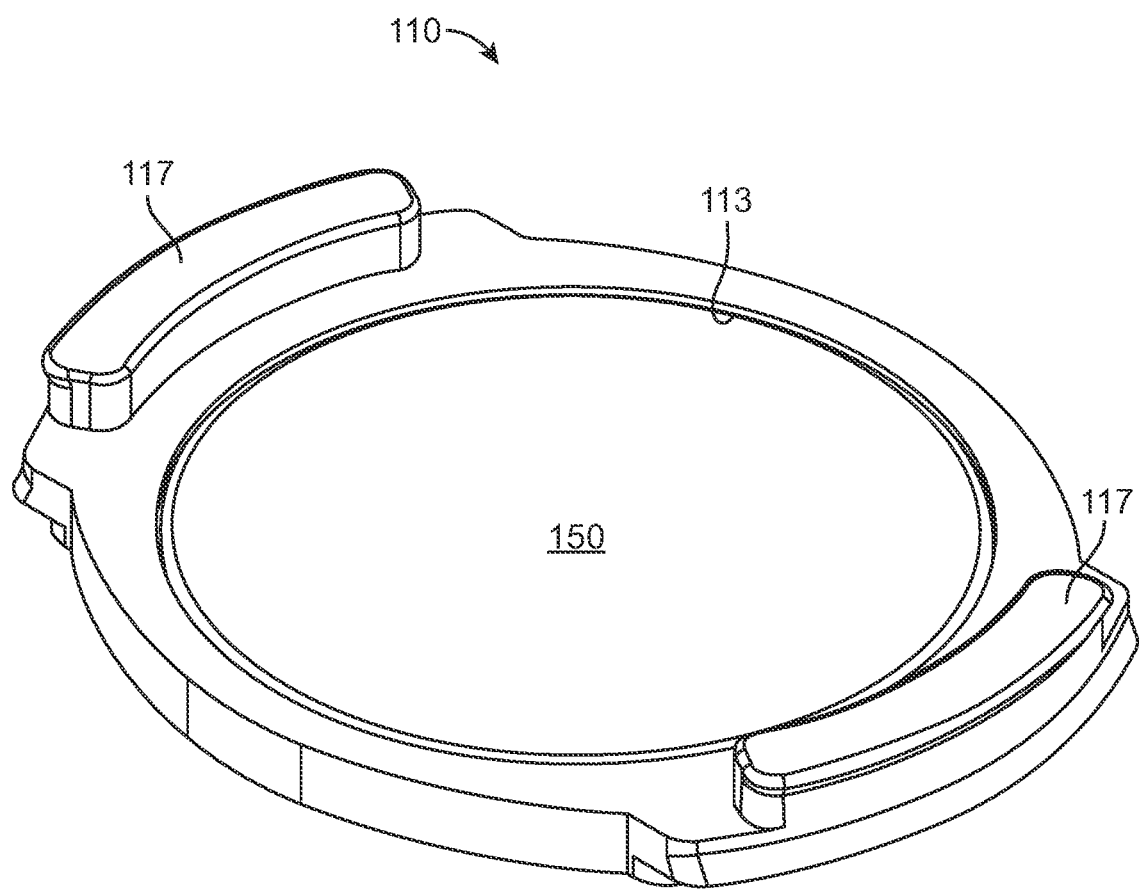
FIG. 19E is the internal support of the device of FIG. 19B supporting a posterior optic.

FIGS. 16A-16F and FIGS. 17A-17F illustrate an implementation of an AIOL having an internal support 110. The internal support 110 can function to mechanically isolate the optical elements (anterior and posterior) from stresses imparted by the stabilization system 120 to limit optical distortion. As best shown in FIG. 16D and FIG. 17D, the internal support 110 can be a ring-like element that defines a central aperture 113. The aperture 113 can have an inner diameter that is sized to receive at least a portion of the static lens element 150 therethrough. As described elsewhere herein, the static element 150 can have a flat surface 151 on a first side, a curved surface 152 on a second, opposite side, and a peripheral connecting ring 153 having a sealing surface 154. The perimeter sealing surface 154 of the static element 150 can abut and seal against a posterior-facing, generally planar surface surrounding the aperture 113 of the internal support 110. The peripheral connecting ring 153 of the static element 150 can be engaged by the inner diameter of the central aperture 113. Thus, the static element 150 can be held by the aperture 113 of the internal support 110 and the curved surface 152 available through the aperture toward the posterior side of the AIOL 100. The perimeter region 144 of the anterior optic 145 can be positioned over a planar, anterior-facing surface of the internal support 110 surrounding the aperture 113. As such the planar portion of the internal support 110 surrounding the aperture 113 is captured between the perimeter region 144 of the anterior optic and the sealing surface 154 of the static element 150. The internal support 110 can have an outer perimeter that generally matches an outer perimeter of the lens body 105. The annular element 104 of the lens body 105 is coupled to the outer perimeter of the internal support 110 (see FIGS. 16B and 17B). The outer perimeter of the internal support 110 can be spaced a distance internal to the peripheral membrane 140 such that upon movement of the force translation arms 115, the peripheral membrane 140 can be urged a distance inward to cause accommodative shape change. Thus, the annular element 104 can be coupled at a first location on an anterior surface of the internal support and the annular element 104 can be coupled at a second location on a posterior surface of the internal support 110 such that the peripheral membrane 140 spans the distance between the first location and the second location (see FIGS. 16C and 17C). The distance between the first and second locations is defined by a width of wedge-shaped features 117 near the outer perimeter. The presence of these features 117 limits movement of the force translation arms 115 and reduces the risk of tearing during implantation in the eye such as by injection. The features 117 can have a generally wedge shape such that a thicker portion of the feature 117 is positioned more peripherally facing the peripheral membrane 140 and tapers toward the central aperture 113. An outer facing surface of the features 117 can be concave or otherwise angled inward to ensure the peripheral membrane 140 avoids contact with the feature 117 during movement of the force translation arms 115. It should be appreciated that the feature 117 need not be wedge shaped. For example, FIG. 18C and FIG. 19E illustrate other implementations of an internal support 110 having features 117 that are more square or rectangular in cross-section such that they do not taper toward the central aperture 113.

Generally, the material of the internal support 110 has enough rigidity to mechanically isolate the optical elements, particularly when the AIOL 100 is placed under stress imparted by stabilization haptics 160. FIGS. 17A-17F illustrate an implementation of an AIOL 100 having an internal support 110 configured to mechanically isolate the optical portions of the device from stresses imparted by the stabilization haptics 160. The internal support 110 is configured to prevent optical distortions of the central area even during movement of the stabilization haptics 160 such that the stabilization haptics 160 impart no shape change to the optical portions of the device such as the dynamic membrane 143 or the anterior optic 143. The strength of the internal support 110 relative to other portions of the AIOL 100 such as the shape deformation membrane 140 and the dynamic membrane 143 provides increased durability during manipulation and handling of the lens during insertion.

Regardless the configuration, the internal support 110 can limit efficiency-sapping lens movements in regions of the AIOL 100 other than where accommodative movements are desired. The internal support 110 functions to focus all ciliary-induced pressure toward the central, dynamic membrane 143. The internal support 110 mechanically isolates dynamic areas of the AIOL 100 and structurally reinforces non-dynamic areas of the AIOL 100 thereby focusing the shape change only where desired for accommodation—the side deformation membrane 140 via movements of the force translation arm 115 and the dynamic membrane 143 from the increased pressure within the fluid-filled chamber 155. The geometry and rigidity of the internal support 110 serves to mechanically prevent other lens regions from deforming under the increased internal pressure of the fluid-filled capsule. The internal support 110 can be formed of any of a variety of materials or combination of materials that can be opaque or clear, but are generally more rigid than the moveable parts of the AIOL 100. In some implementations, each component of the AIOL 100 is formed of the same material, which provides advantages from a manufacturing stand-points. The material of the various components may be the same (i.e. silicone), but the mechanical properties of the various components may be unique depending on what function the component performs for the AIOL (i.e. shape change or force transfer or centering and stabilization). One component of the AIOL may be more rigid than another component of the AIOL (e.g. the internal support 110 compared to the peripheral membrane 140), but both components may be the same material. The more rigid component may be more rigid due to that component's geometry and dimensional differences compared to the less rigid component. As such, the internal support 110 and the membranes 140, 143 can be formed of the same silicone material, but because the membranes 140, 143 have a significantly decreased thickness compared to the internal support 110 the membranes 140, 143 are easily deformed upon application of a compressive force whereas the internal support 110 is not easily deformed. In some implementations, the internal support 110 can be a silicone elastomer (e.g. silicone PDMS 70-90 shoreA) and the membranes 140, 143 can be a silicone elastomer (e.g. silicone PDMS 20-50 shoreA). Additionally, the internal support 110 can include a geometry that imparts a higher rigidity and stiffness relative to the membranes 140, 143.

The various components and features of the AIOLs described herein can be incorporated in any of a variety of combinations. As such, description of a particular feature shown with respect to a particular drawing is not intended to be limiting in that the feature can be incorporated into another implementation of an AIOL described herein. For example, the AIOLs described herein can include a stabilization system that incorporates one or more features of the stabilization systems described herein. Further, the AIOL having the stabilization system features can be combined with any of a variety of features described with respect to the force translation arm 115 or the shape deformation membrane 140, for example.

The AIOLs described herein can achieve an optical power or diopter (D) in a desirable range (e.g. up to approximately 5 D change) due to shape change of the anterior optic 145 upon application of a small amount of force (e.g. as little as 0.1-1.0 grams force (gf)) and micrometer range movements of the force translation arms 115 (e.g. up to approximately 25 µm-100 µm collectively from each side or from a single side). As such, the AIOLs described herein harness small forces and provide reliable optics with mechanical isolation such that even asymmetric force can achieve a spherical result in the accommodation. The compressible region can be the region of the sealed chamber 155 that undergoes deformation upon movement of the deformation membrane 140 to cause the reactive outward bowing of the dynamic membrane 143. The compressible region can have a length L that is the distance the deformation membrane 140 is displaced inward, a height H that is the cross-sectional height of the deformation membrane 140 along the optical axis of the lens, and an Arc Length W that is the cross-sectional length of the shape deformation membrane 140 perpendicular to the optical axis A of the lens 100. Displacement of the shape deformation membrane 140 results in a volumetric compression V that correlates with the product of L*H*W. In the case of an lens 100 having two force transfer arms 115 with two shape deformation membranes 140, the volume of fluid V compressed by ciliary movement of magnitude L would be roughly 2*L*H*W. The actual volume may be slightly less than this idealized calculation because of inefficiencies associated with elastic deformation and complex geometries. The volume of the lens bowing can be described by:

$$V = \frac{\pi h}{6}(3a^2 + h^2),$$

where the lens height (h) can be calculated from Pythagoras equation: $(r-h)^2 + a^2 = r^2$. Hence: $h = r - \sqrt{(r^2 - a^2)}$. As an example, if the refractive index of the optical fluid within the sealed chamber 155 is 1.4 and the diameter of the lens is 3 mm, a 28 μm movement (L) of two, opposing deformation membranes 140 with Height (H) 0.37 mm and Arc Length (W) 3.0 mm creates a sufficient amount of pressure applied by the optical fluid against the anterior optic 145 to form a 1 D lens. If the diameter of the lens is 3 mm, an 84 μm movement of two deformation membranes 140 with Height (H) 0.37 mm and Arc Length (W) 3.0 mm can create a sufficient amount of pressure applied by the optical fluid against the dynamic membrane 143 to form a 3 D lens. Additional examples are provided below in Tables 1 and 2 below. Table 1 illustrates device parameters including power change in diopters (D), diameter of the dynamic membrane 143, curvature of outward bowing of the dynamic membrane 143, and volume of lens bowing or the volume of the optical fluid occupying the space created within the outward bowing for devices filled with 1.382 refractive index (RI) of optical fluid. Table 2 illustrates device parameters including power change in diopters (D), diameter of the dynamic membrane 143, curvature of outward bowing of the dynamic membrane 143, and volume of lens bowing or the volume of the optical fluid occupying the space created within the outward bowing for devices filled with 1.43 refractive index (RI) of optical fluid. The curvature is calculated based on a starting power of 0D. The curvature can be measured directly with a surface profilometer or a white light interferometer. The curvature can also be inferred based on a measured power change and known refractive indices.

TABLE 1

| Power Change (D) | Dynamic Diameter (mm) | Curvature (mm) | Volume (mm³) |
|---|---|---|---|
| 3 | 2.5 | 15.3 | 0.125 |
| 4 | 2.5 | 11.5 | 0.167 |
| 5 | 2.5 | 9.2 | 0.210 |
| 3 | 3.0 | 15.3 | 0.260 |
| 4 | 3.0 | 11.5 | 0.348 |
| 5 | 3.0 | 9.2 | 0.436 |
| 3 | 3.5 | 15.3 | 0.482 |
| 4 | 3.5 | 11.5 | 0.645 |
| 5 | 3.5 | 9.2 | 0.810 |

TABLE 2

| Power Change (D) | Dynamic Diameter (mm) | Curvature (mm) | Volume (mm³) |
|---|---|---|---|
| 3 | 2.5 | 31.3 | 0.061 |
| 4 | 2.5 | 23.5 | 0.082 |
| 5 | 2.5 | 18.8 | 0.102 |
| 3 | 3.0 | 31.3 | 0.127 |
| 4 | 3.0 | 23.5 | 0.169 |
| 5 | 3.0 | 18.8 | 0.212 |
| 3 | 3.5 | 31.3 | 0.235 |
| 4 | 3.5 | 23.5 | 0.314 |
| 5 | 3.5 | 18.8 | 0.393 |

In some implementations, the device has a dynamic optic diameter of 2.5 mm and is filled with oil having 1.382 RI. This device can achieve an accommodation of about 1.4 D with about 20 microns movement upon application of about 0.26 gf, about 2.6 D with about 40 microns movement upon application of about 0.58 gf, about 3.5 D with about 60 microns movement upon application of about 0.85 gf, about 4.7 D with about 80 microns movement upon application of about 1.1 gf, and about 6.3 D with about 100 microns movement upon application of about 1.4 gf.

The AIOLs 100 described herein have an improved shape change efficiency. This improved efficiency allows for a greatly reduced volume of the sealed chamber 155 (and thus, the optical fluid 156 filling the chamber 155) and a much thinner maximal cross-sectional dimension, particularly near the perimeter region of the AIOL 100. Even with the minimized cross-sectional dimension at non-optical perimeter regions the effective dioptric change (e.g. ±3 or ±4 diopters) is comparable to lenses with larger volumes. In some implementations, the volume of the chamber 155, and thus the optical fluid 156, can be less than about 8.5 mm³ down to about 2 mm³. In some implementations, the volume can be between 3 mm³ to about 6 mm³. The small volume can provide sufficient dioptric change in the range of ±4 diopters upon micron-range displacement of the membrane 140 resulting in corresponding displacement of optical fluid 156 in the chamber 155 that is in a range of about 0.2 mm³ to about 0.3 mm³. The displacement of optical fluid 156 achieved depends on the desired accommodating range (e.g. 3 or 4 D), the diameter of the shape change membrane, and the refractive index of the material within the AIOL. The lens can be designed to achieve such an "accommodated state" with the design of the side membranes, limitations of physiological processes, and maximum efficiency mechanics.

The AIOLs described herein can be implanted according to a variety of surgical methods known in the art. Depending upon the features and components of the device, they can be implanted using various techniques or using various implements. The devices described herein can be used alone or in combination with another intraocular lens or the patient's natural lens. The power of the lens body as well as the relative position of the force translation arms and/or stabilization system can be adjusted and/or fine-tuned prior to implantation, during implantation or any time after implantation. The devices described herein can be implanted such that at least a portion of the device is positioned outside the lens capsule, for example, anterior to the capsule and posterior to the iris. The devices described herein can be implanted such that the central portion of the lens body is aligned with the optical axis of the eye. The force translation arms can be positioned relative to the one or more ciliary structures such as the ciliary body or the apex of the ciliary muscle. The force translation arms can be positioned such that they abut with the ciliary structure (or very closely associated to the ciliary structure without abutting) without causing compression of the lens body including the deformable region of the lens body when the ciliary structure is in the resting, unaccommodated state. However, the force translation arms can be positioned close enough to the ciliary structure such that upon contraction of the ciliary muscle the lens body undergoes accommodation and upon relaxation of the ciliary muscle the lens body undergoes disaccommodation and the materials of the lens body rapidly return to their resting state. The relative position and length of the force translation arms can be adjusted according to the various methods described above using one or more of the various features for adjustment described herein. The stabilization system can be positioned within the ciliary sulcus, against the ciliary processes or within a portion of the capsular bag to further stabilize the device within the eye and to prevent the device from vaulting anteriorly toward the iris, therein minimizing iris touch. The resting power of the lens body can also undergo further adjustment and fine-tuning according to the various methods described herein and using one or more of the various features for power adjustment described herein.

The dimensions of the components of the devices described herein can vary. In some implementations, the overall optic zone portion of the lens body 105 can have a diameter that is about 2.5 mm, about 3.0 mm, about 3.5 mm, about 4.0 mm, about 4.5 mm, about 5.0 mm, about 5.5 mm, about 6.0 mm, about 6.5 mm, or greater diameter. In some implementations, the accommodating diameter, or the region of the central optic zone that undergoes a shape change (e.g. the dynamic membrane 143), is 1.0 mm-6.0 mm in diameter. In some implementations, the dynamic membrane 143 is 1.5 mm-3.5 mm in diameter. In some implementations, the dynamic membrane 143 is 1.7 mm-2.5 mm in diameter. In some implementations, the AIOL 100 can be foldable such that the device can be implanted in the eye through an incision smaller than an otherwise non-foldable, rigid AIOL. For example, a device having flexible or foldable stabilization system 120 can have a first diameter during implantation that is smaller than the diameter it achieves after implantation following unfolding or expansion of the stabilization system 120. In some implementations, the device can include a support and the support can be made from a flexible material(s) such that the support can bend during implantation of the device. In other implementations, the device can flex or fold across a part of the device. As described above, the AIOL can include one or more internal supports 110 and the internal supports 110 can be spaced a distance away from one another forming corridors 112 through the sealed chamber 155 between the pillars of support resulting in a sealed chamber 155 having any of a variety of shapes (e.g. H-shape, X-shape or other shape). FIGS. 3D-3G show examples of a potential fold lines $F_1$ $F_2$ along one or more corridors 112 of the AIOL. Other fold lines exist. The AIOLs described herein can be folded along one or more of these corridors 112 such that the adjacent internal supports 110 fold on top of one another. As described above, the force translation arms 115 can include a central region 116 that is thinner to encourage folding across these central regions 116 (see FIGS. 18A-18C). Folding the AIOLs described herein in this manner or rolling of the flexible AIOL allows for the device to be implanted through smaller incisions that wouldn't otherwise be possible with AIOLs having rigid components such as supports that are not configured to fold. In addition to reducing the overall size of incision needed for implantation, folding and/or rolling of the AIOLs described herein allows for use of typical insertion tools or minimally-invasive implantation tools. The AIOLs described herein can also have a narrow cross-sectional thickness allowing for insertion into the eye through small incisions. In some implementations, the AIOL 100 can have a cross-sectional thickness between the anterior and posterior ends that is approximately 2.5 mm to as thin as about 0.5 mm. In some implementations, the device has a cross-sectional maximal thickness of about 1.3 mm. As will be described in more detail below, the devices described herein are configured to be implanted through an incision that is less than about 4 mm. For example, the devices can be inserted through a small incision, such as a clear corneal incision that is no greater than about 3.5 mm.

Figure 4C:
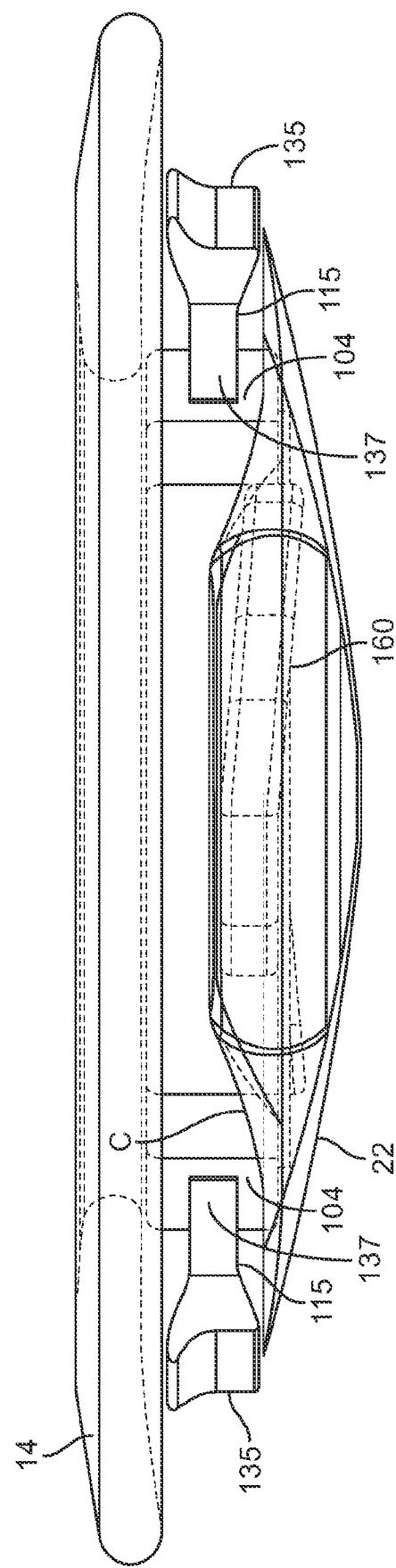
Figure 5B:
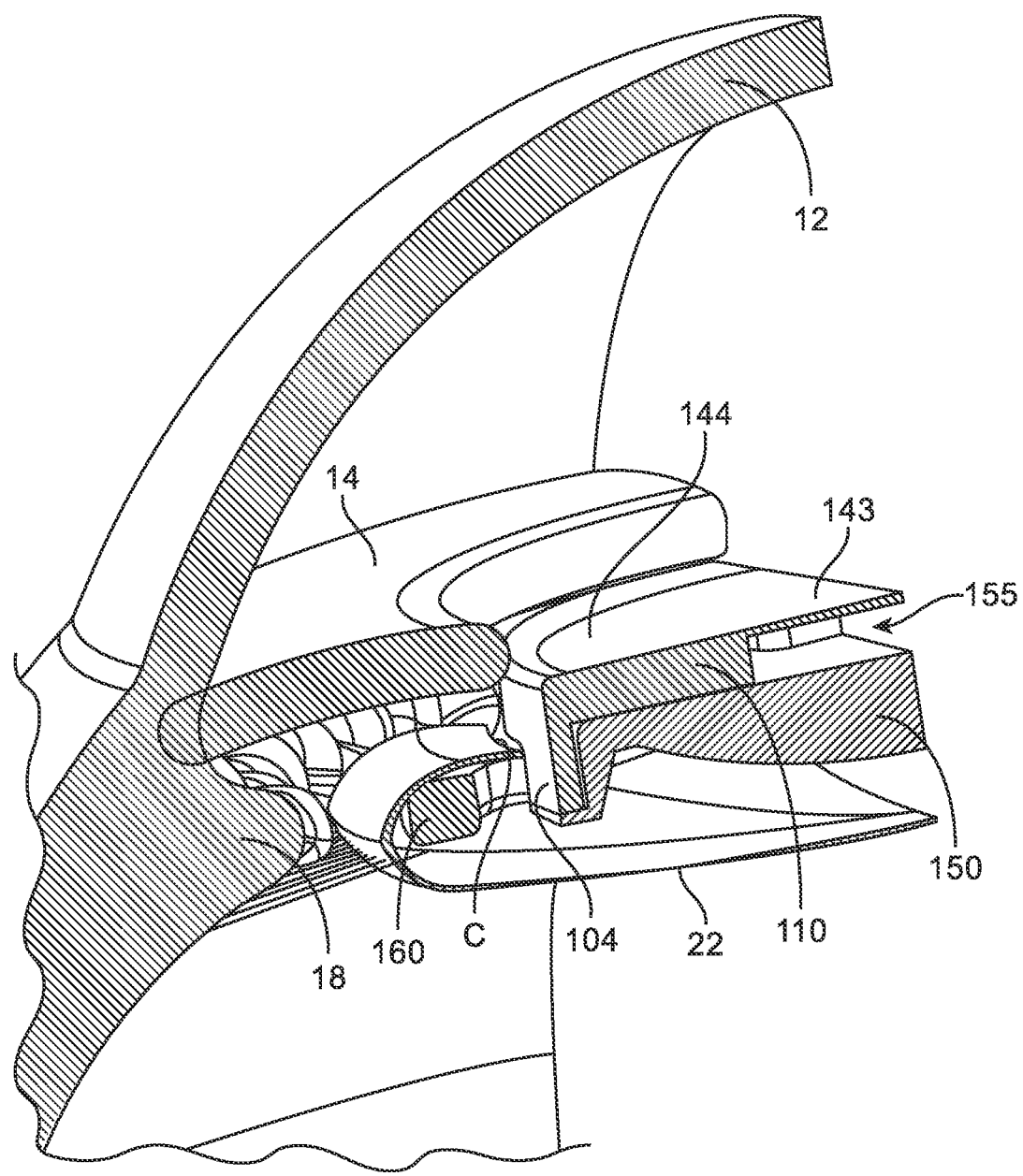

FIGS. 4A-4C and also FIGS. 5A-5B illustrate an implementation of an AIOL 100 implanted within an eye such that a posterior portion of the AIOL 100 including the stabilization system 120 and at least a portion of the static element 150 are inserted through a capsulorhexis C into an anterior region of the capsular bag 22. An anterior portion of the AIOL 100 including the force translation arms 115 and anterior optic 145 extend outside of the capsular bag 22. As such, the anterior capsule aids in orientation of the AIOL 100 relative to the ciliary body apex. The edge of the capsular bag 22 created by the capsulorhexis C can extend over an anterior face of the stabilization system 120 (whether the system 120 includes one or more of a stabilization haptic 160, flanges 172, and/or a ring-like structure providing 360 degree stabilization). For example, in some implementations the edge of the capsular bag 22 can extend over an anterior face of the one or more stabilization haptics 160 and abut the annular element 104 of the lens body 105 near where the interior region 161 of the stabilization haptic 160 couples to the annular element 104. Alternatively, the edge of the capsular bag 22 can extend over an anterior face of the flange 172 and slide into groove 174 between the anterior surface of the flange 172 and the posterior surface of the annular element 104. As described above and as shown in FIGS. 15A-15C, and 16A-16F), the anterior surface of the flange 172 can have an anterior-extending outer elevation configured to engage with a posterior-facing internal surface of the capsular bag of the anterior capsule. Alternatively, the edge of the capsular bag 22 formed by the capsulorhexis C can extend over the flange 172 and under a protective rim 1210 of the shield 1205 as described above with respect to the stabilization system 120 shown in FIG. 12. Regardless the stabilization mechanism 120, the edge of the capsular bag created by the capsulorhexis C can tuck under a posterior face of the force translation elements 115 such that the force translation elements 115 extend outside the capsular bag 22 and at least a portion of the stabilization system 120 remains inside the capsular bag 22. Implantation of the AIOL 100 in this over-under manner provides additional stabilizing support to orient the AIOL 100 with a visual axis of the eye and prevent movement of the AIOL 100 toward the iris 14. Generally, the AIOL described herein can maintain a clearance from the iris 14 upon implantation that is approximately 0.05 mm-0.5 mm. The edge of the capsular bag 22 provide a generally posterior-directed force on the anterior face of the stabilization system 120 pulling the AIOL away from the iris 14. This force is counterbalanced by the generally anterior-directed force due to engagement between the contact portion 135 of the force translation arms 115 and the ciliary structures of the eye.

It should be appreciated that the AIOLs described herein need not be implanted using an over-under configuration. As described elsewhere herein, the stabilization haptics 160 can be positioned within the ciliary sulcus and just a posterior portion of the AIOL positioned within the capsular bag. Positioning the stabilization haptics 160 within the ciliary sulcus can provide a posterior-direction pressure on the AIOL 100 for further stabilization and to aid in keeping the perimeter portions of the device away from the iris.

Still with respect to FIGS. 5A-5B, the maximum cross-sectional thickness T of the AIOL 100 can be approximately 2.5 mm or less such that the device can be inserted through a clear corneal incision having a length of approximately 3.5 mm. In some implementations, the maximum cross-sectional thickness T taken along a plane of the optical axis A of the lens is between about 0.5 mm and 1.5 mm thick. In some implementations, the maximum cross-sectional thickness T of the AIOL taken along a plane of the optical axis A of the lens is approximately 1.3 mm, is implantable through a 3.5 mm clear corneal incision.

Figure 17E:
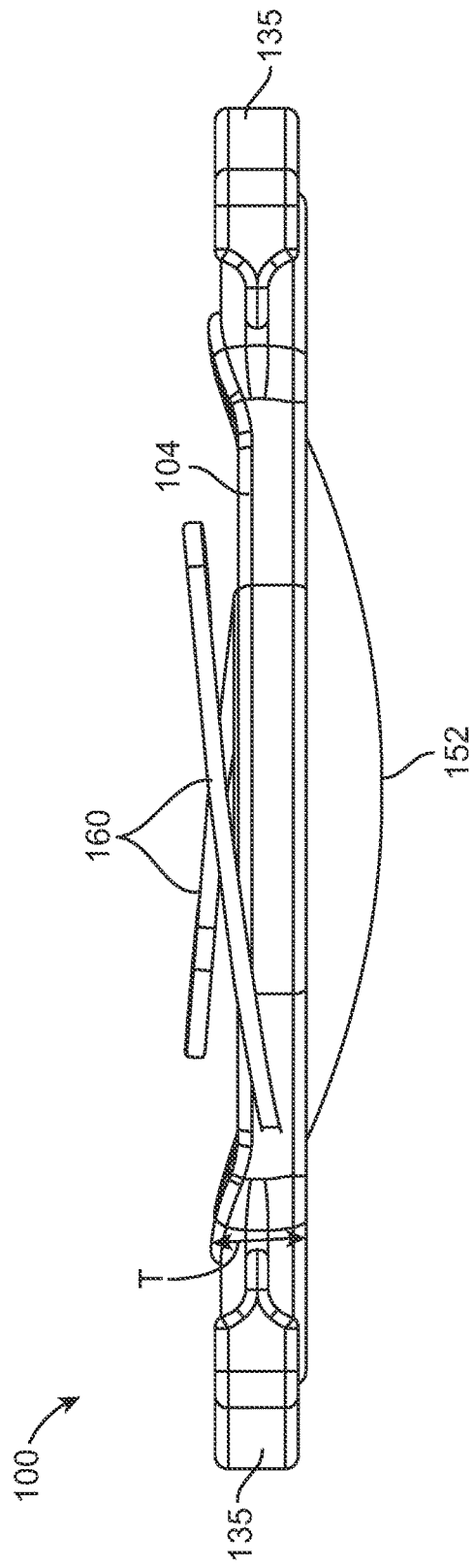
FIGS. 17E-17F are side views of the device of FIG. 17A.
Figure 17F:
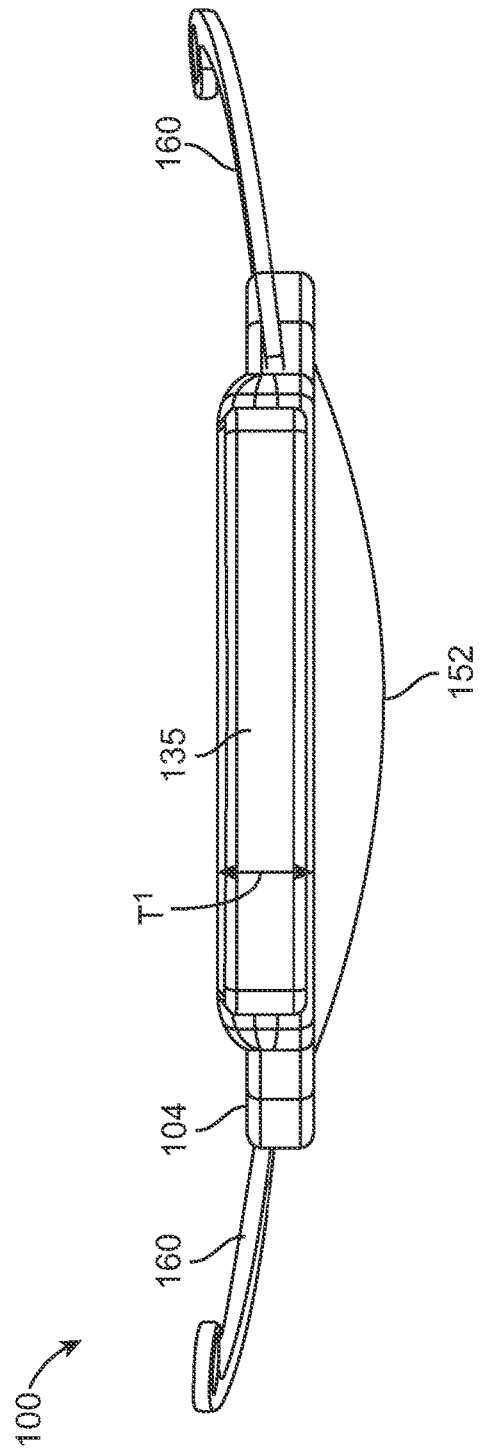

The AIOLs described herein rely on direct contact with the ciliary muscle in order to achieve accommodation. Thus, at least a portion of the perimeter region of the AIOLs must be sized to fit in this narrow space between the capsular bag and the iris. As described elsewhere herein, the AIOLs described herein have a thin maximum cross-sectional dimension near the perimeter region to provide this direct engagement without negatively impacting the iris. Minimizing the cross-sectional dimension of the perimeter region greatly reduces the internal volume of the AIOL. Additionally, the inner-facing surfaces of the sealed chamber have reduced angles to further improve the efficiency of the AIOL. The improved efficiency of the components of the AIOLs, renders them capable of an effective dioptric change (e.g. ±4 diopters) in spite their smaller overall cross-sectional dimension and internal volume compared to an AIOL having a much larger internal volume. The thickness profile of the non-optical perimeter region (i.e. regions of the AIOL 100 lying outside the optical region of the lens) can be minimized to avoid contact with the iris. FIGS. 4A-4B illustrate an implementation of an accommodating intraocular lens positioned within the capsular bag 22 and showing relative position of the perimeter region to the iris 14. FIGS. 16A-16F and also FIGS. 17A-17F illustrate implementations of an AIOL in which the maximum cross-sectional dimension near this perimeter region is minimized. The thickness of the AIOL 100 near the optical zone in the posterior direction (e.g. the curved surface 152 of the posterior static element 150) extends into the capsular bag 22 and has little to no impact on the iris 14. As best shown in FIGS. 16E and 17E, the maximum cross-sectional thickness T of the perimeter region of the AOIL 100 (i.e. excluding the posterior static element 150 projecting posteriorly into the capsular bag) can be between about 500 µm to about 700 µm. As best shown in FIGS. 16F and 17F, the maximum cross-sectional thickness T' of the perimeter region of the AOIL 100 (i.e. excluding the posterior static element 150 projecting posteriorly into the capsular bag) can be between about 700 µm to about 950 µm.

The AIOL can be folded or rolled up into an applicator having a 2.5 mm tip although it should be appreciated that other applicators are considered herein. Generally, large scleral incisions are to be avoided, however, the AIOLs described herein can be implanted through a scleral tunnel or a scleral incision between about 6 mm and 7 mm long.

In some implementations, as described above, the AIOL is implanted in an over-under manner. The over-under manner of implantation stabilizes the lens position and limits iris touching as described above. The over-under implantation also prevents inadvertent rotation of the AIOL 100 around the optical axis A of the device. Rotation of the AIOL 100 around the optical axis A can result in a horizontally-oriented force translation arm 100 moving toward a vertical orientation that is more prone to shifting away from the ciliary structures that can impair the accommodating mechanism of the AIOL. As an example, the AIOL 100 can include two, opposing force translation arms 115 and can be implanted such that the contact portion 135 of each force translation arm 115 is either in resting contact or readily in contact upon contraction of the ciliary muscle 18 (e.g. ciliary body apex) to drive shape change of the optics during accommodation and disaccommodation. As mentioned above, the AIOL can (but need not) be oversized, for example, by 0.05 mm-0.5 mm. The oversizing can be used to ensure contact between the ciliary structures and the force translation arms. However, in certain circumstances the oversizing may not be sufficient to ensure contact due to shifting and settling of the lens or post-operative changes in the ciliary body diameter. For example, the AIOL can be oriented such that a gap of approximately 0.05 mm may exist between the ciliary structure and the contact portion 135 of the force translation element 115 on a first side and another 0.05 mm gap between the contact portion 135 of the force translation element 115 on a second side and the ciliary structure. When optimally centered, the gaps remain substantially equal on each side. If the AIOL is implanted such that the opposing force translation elements 115 are oriented vertically relative to the eye (and to each other), the AIOL 100 can settle or shift downward due to gravity such that the gap on the superior or cephalad side increases to approximately 0.1 mm and the gap on the inferior or caudal side decreases towards 0 and remains in resting contact against the ciliary structure. Implantation of the AIOL 100 such that the opposing force translation arms 115 are oriented horizontally (medio-laterally) relative to the eye (and to each other) minimizes the shifting of the AIOL 100 and the optimal spacing between the force translation arms 115 and the ciliary structures is maintained during use. Implantation of the stabilization haptics 160 inside the capsular bag 22 and the force translation arms 115 outside the capsular bag 22 limits rotation of the AIOL 100 around the optical axis A and avoids de-centering of the device, which can render inoperable the accommodation mechanism of the lens. The orientation of the AIOL in the eye in combination with an oversizing of greater than 0.05 mm-0.5 mm can enhance centering and ensure contact with the eye structures. It should be appreciated that oversizing is not necessary for proper placement and fit of the AIOLs described herein. For example, the patient's ciliary diameter at the plane of the AIOL can be accurately imaged and measured to avoid the need for oversizing to overcome issues with fit.

Figure 6A:
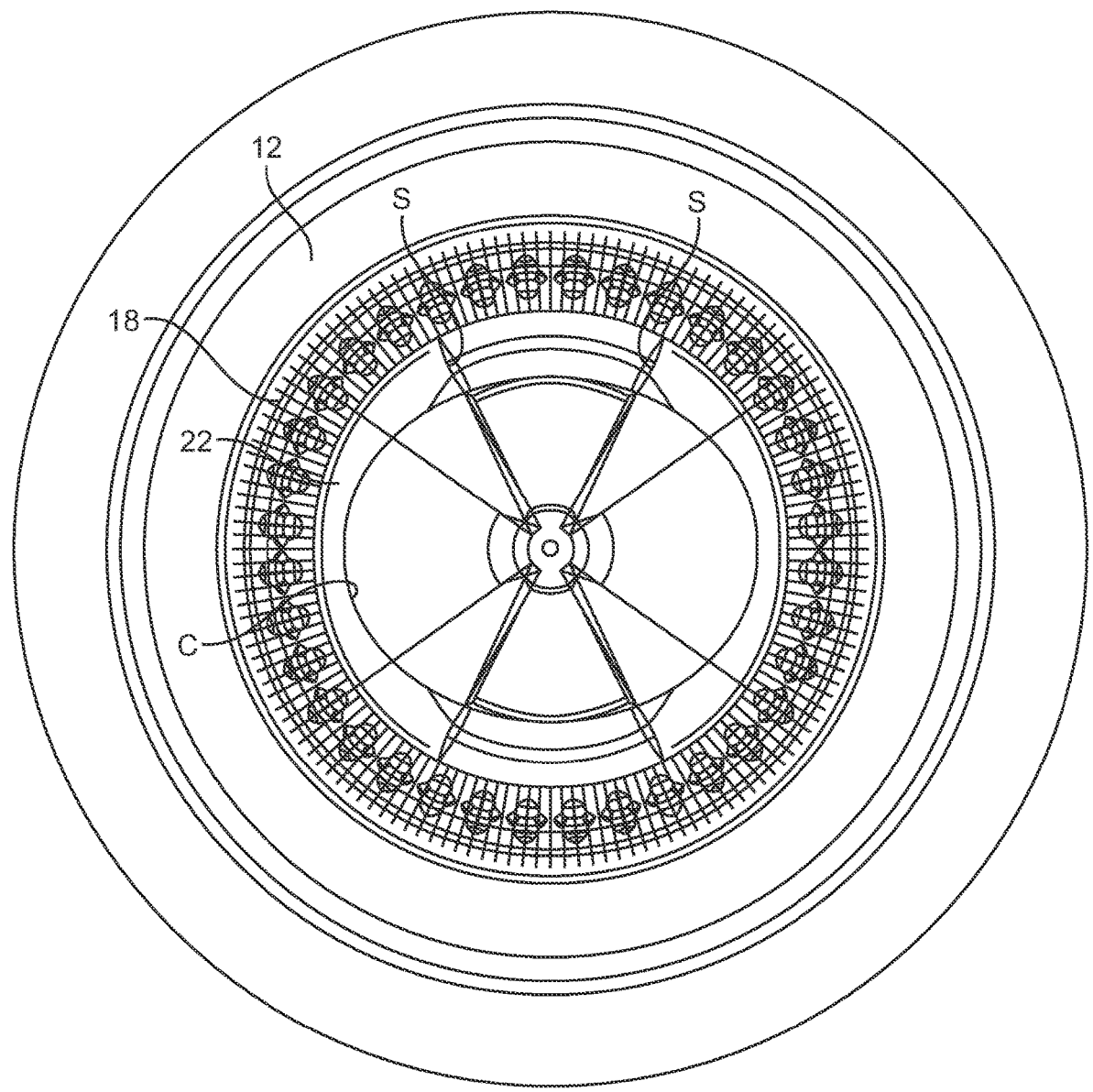
FIG. 6A is an anterior view of the eye showing an oval capsulorhexis.
Figure 6B:
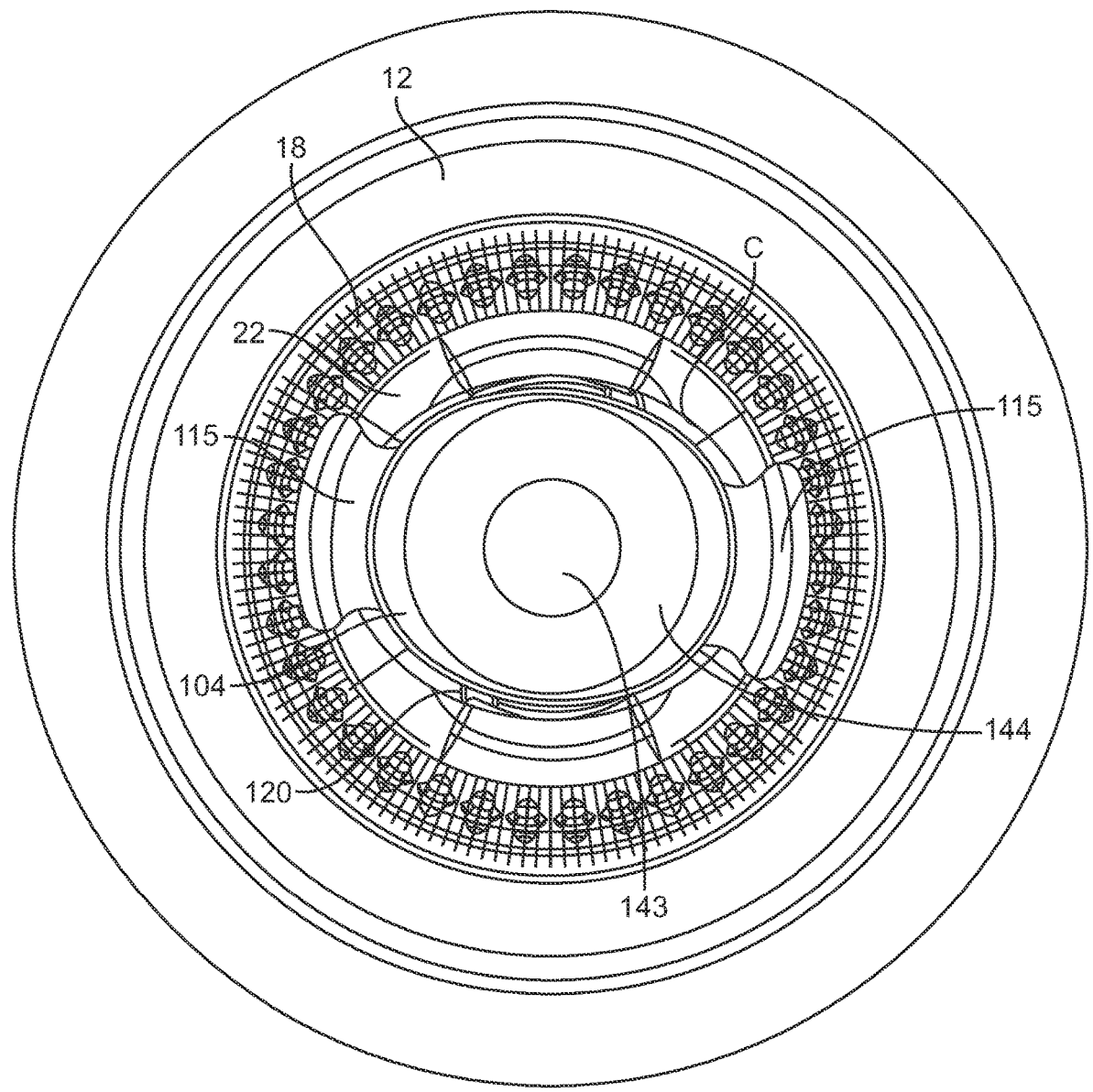
FIG. 6B is an anterior view of the eye in FIG. 6A showing an accommodating intraocular lens device positioned within the eye with the iris hidden.

The AIOL described herein can be implanted by twisting or rotating into position such that the horizontally-oriented force translation arms 115 wedge into engagement with the ciliary muscle. This allows for adjustment of the fit during implantation. FIG. 6A is an anterior view of the eye showing a capsulorhexis. Although not represented in this figure, the ciliary muscle 18 naturally has a generally oval shape from an anterior view. The AIOL 100 can be inserted through a small corneal incision through the anterior chamber, past the iris into the posterior chamber. Once inside the posterior chamber, the AIOL 100 can unfold and/or unroll. The AIOL can be oriented such that a posterior surface of the device is positioned inside (posterior to) the capsulorhexis and the force translation arms 115 remain outside (anterior to) the capsulorhexis. The AIOL can be rotated around the optical axis A of the device relative to the ciliary muscle until each of the force translation arms 115 wedge into position against the ciliary structure (e.g. the ciliary sulcus or ciliary body apex). The force translation arms 115 wedge into position such that they are generally positioned in a horizontal or mediolateral orientation relative to the eye. The force translation arms 115 can be rotated to wedge into contact with the ciliary muscle 18 or can be rotated to maintain a small gap between the contact portions 135 and the eye tissue. The gap can be, for example, a 0.1 mm gap. Once the force translation arms 115 are generally oriented horizontally relative to the eye, the edges of the capsular bag 22 formed by the capsulorhexis C are extended over the anterior surface of the stabilization haptics 160. Securing the haptics 120 in the capsular bag 22 in this manner pulls the anterior face of the AIOL 100 away from the iris 14. The narrow cross-sectional thickness T of the AIOL also provides a greater clearance relative to the iris 14. In implementations where the stabilization haptics 120 are designed to fit within the sulcus, the posterior end region 107 or posterior-most surface of the AIOL can be positioned within the edges of the capsular bag 22 and the stabilization haptics 160 are positioned anteriorly within the sulcus to thereby press the AIOL 100 in a posterior direction.

The capsulorhexis C can be oval shaped and can optionally incorporate one or more slits S extending radially outward from the edge of the capsulorhexis C and away from the optical axis A of the eye (see FIG. 6A). The oval capsulorhexis C and optional slits S allow the AIOL 100 to sink further into the capsular bag 22 and be positioned more posteriorly by removing or minimizing interference between the anterior capsule and the posterior surface of the AIOL. This allows the force translation arms 115 to more readily access and wedge against the ciliary body apex 18. The anterior capsule can restrict movement of the AIOL while allowing it to be positioned in a more posterior location. In some implementations, the oval capsulorhexis C can be 6 mm×7 mm.

Generally, the rotational implantation of the AIOL can allow for achieving optimal positioning between the contact portions 135 of the force translation arms 115 and the ciliary structures. Rotational implantation can avoid the need to adjust the length of the force translation arms 115. However, it should be appreciated that following implantation in the eye, the AIOL can be further adjusted to improve fit and/or optical power. For example, the length of the force translation arms 115 can be adjusted as can the angle at which the force translation arms 115 extend away from the lens body 105. One or more portions of the device can be expanded or shrunk in situ in order to change the base power of the lens body 105. In some implementations, the expansion and/or shrinking of the lens body 105 can be performed mechanically such as by inserting a screw or another mechanical feature against the lens body 105 to cause a shape change in the lens body 105. In some implementations, the expansion and/or shrinking of the lens body 105 can be performed by injecting and/or withdrawing optical fluid 156 from within the sealed chamber 155 of the lens body 105. The amount of optical fluid 156 can be changed by injecting and/or withdrawing optical fluid 156 within the sealed chamber 155 through an external port having a one-way valve configured to receive a customized syringe needle or pumping mechanism. Tension on the anterior optic 145 (or the static element 150) also can be adjusted by applying energy to the material. For example, the material can be a thermal sensitive material that upon thermal activation can create a bleb. Changes in tension and volume on the lens body 105 can occur depending on whether a bleb, an indentation, or a flattening is formed upon activation of the material. The static lens can also be modified in this way.

Figure 8:
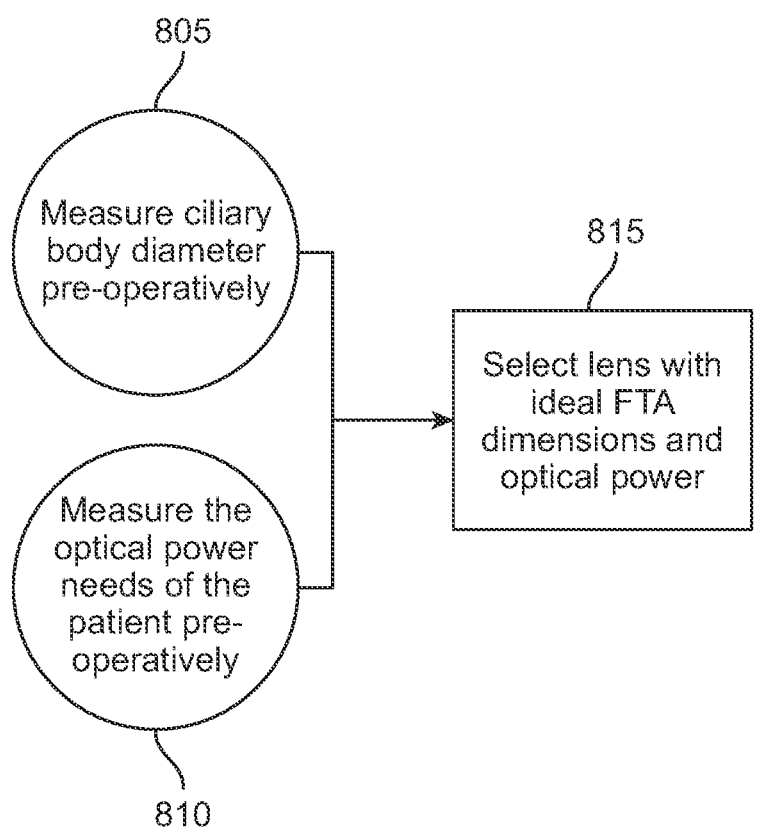
FIG. 8 is a flowchart illustrating an implementation of a method for lens selection.
Figure 9:
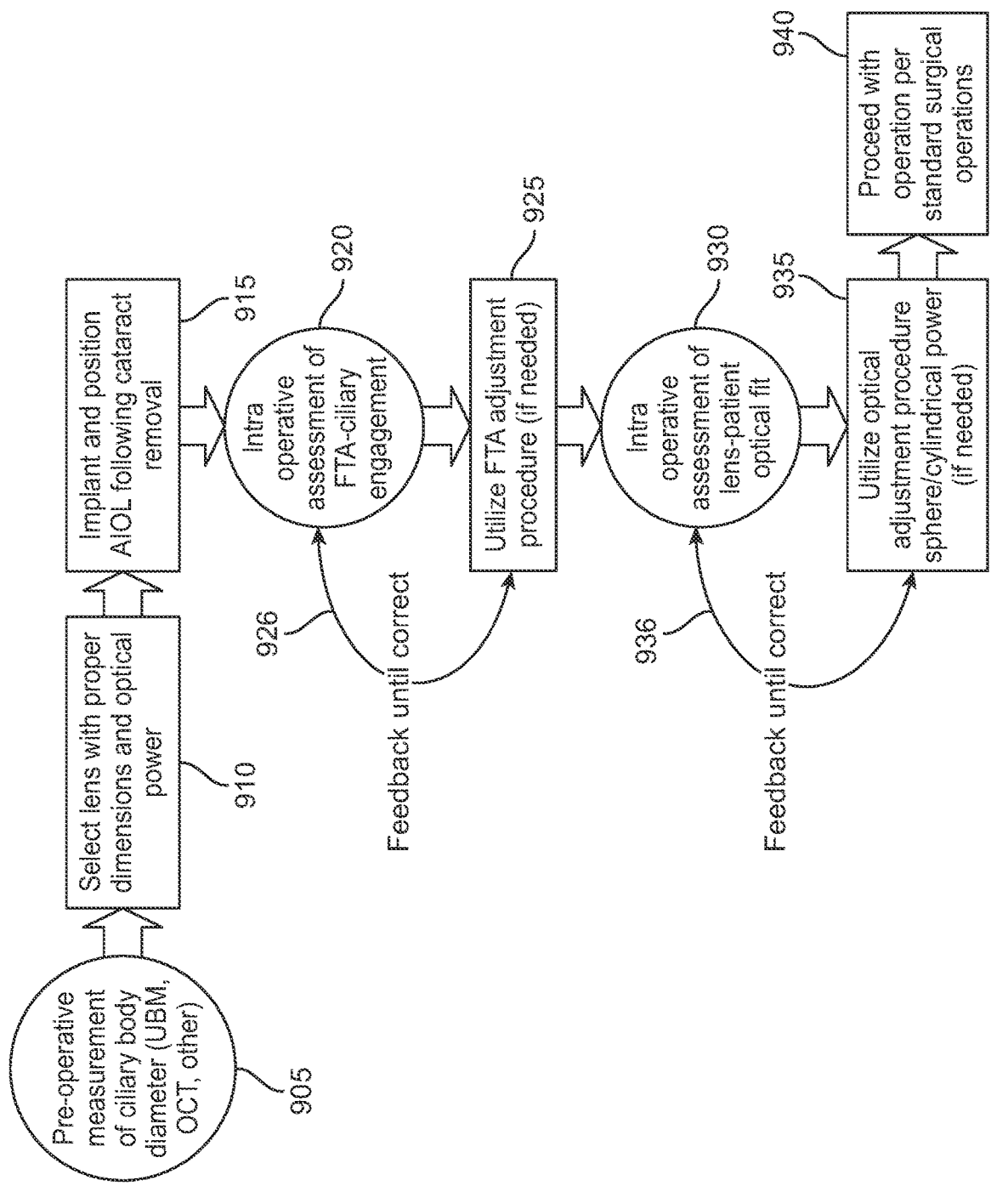
FIG. 9 is a flowchart illustrating an implementation of a method for intraoperative lens adjustment.
Figure 10:
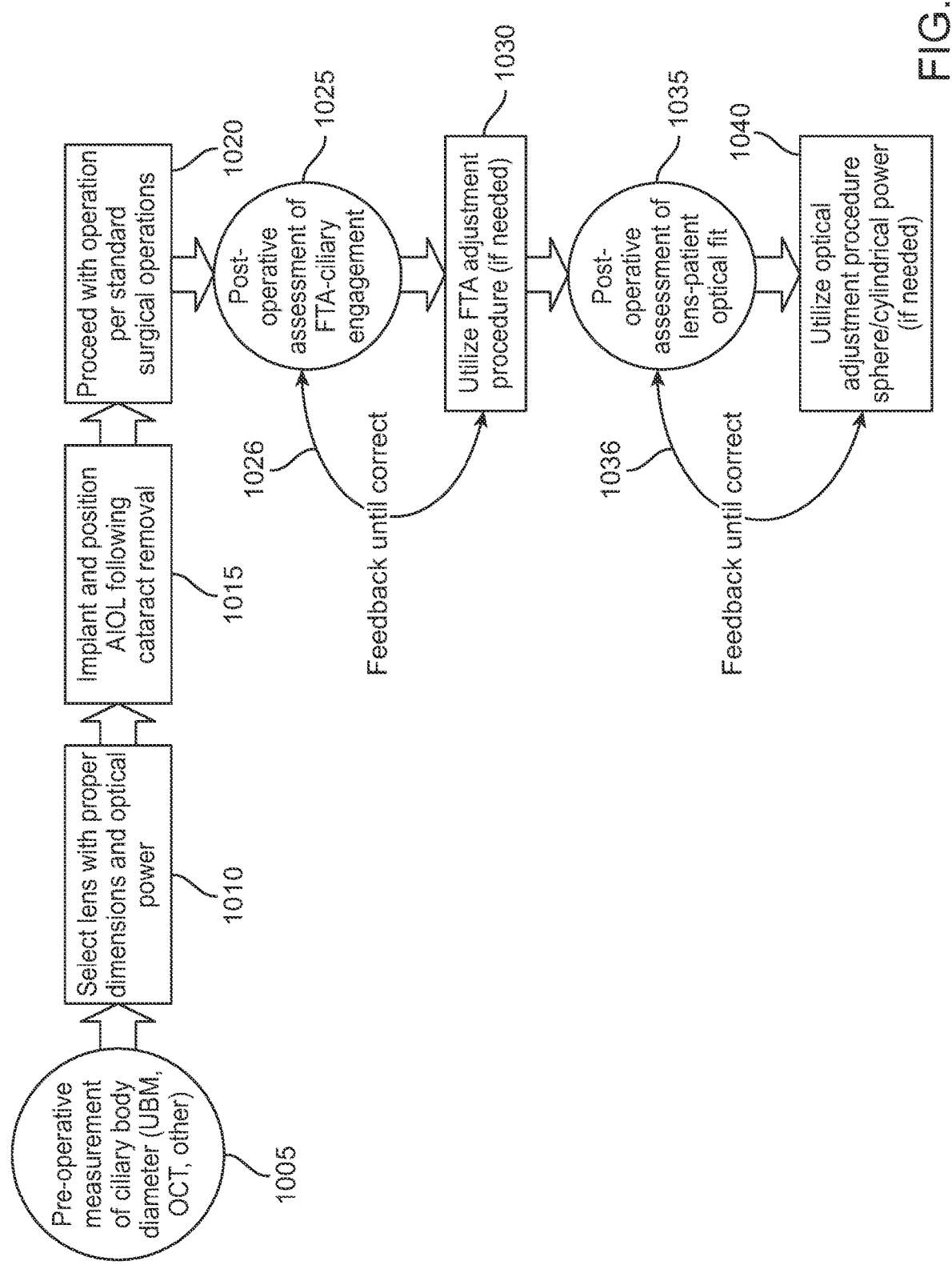
FIG. 10 is a flowchart illustrating an implementation of a method for post-operative lens adjustment.

As shown in FIG. 8, a patient can be assessed pre-operatively by measuring the diameter of their ciliary body (box 805). The diameter of the ciliary body can be measured by ultrasound biomicroscopy (UBM), optical coherence tomography (OCT), or other medical imaging techniques. The optical power needs of the patient can be measured pre-operatively (box 810). These measurements can be used to select a lens 100 having optimal force translation arm 115 dimensions and optical power (box 815). As shown in FIG. 9, following pre-operative measurement of the ciliary body diameter (box 905) and selection of a lens having proper dimensions and optical power for the patient (box 910), the lens 100 can be implanted and positioned following cataract removal surgery (box 915). Intra-operative assessment(s) of the engagement between the contact portions 135 of the force translation arms 115 and the target ciliary structure can be performed (box 920). In some implementations, adjustment of the force translation arms 115 can be performed (box 925) and further intra-operative assessment(s) of the engagement performed (arrow 926). The force translation arms 115 can be adjusted for size in situ as described elsewhere herein. Intra-operative assessment of the optical fit of the lens can be performed until the desired fit is achieved (box 930). In some implementations, the optical power can be adjusted (box 935). The optical power of the lens can be adjusted in situ as described elsewhere herein to create a more spherical or cylindrical lens. Following adjustments, further intra-operative assessment of the optical fit of the lens can be performed until the desired power is achieved (arrow 936). The operation can then proceed per standard surgical operations (box 940). FIG. 10 illustrates an implementation of a post-operative lens adjustment similar to the method described in FIG. 9. Following pre-operative measurement of the ciliary body diameter (box 1005) and selection of a lens having proper dimensions and optical power for the patient (box 1010), the lens 100 can be implanted and positioned following cataract removal surgery (box 1015). The operation can proceed per standard surgical operations (box 1020). Post-operative assessment(s) of the engagement between the contact portions 135 of the force translation arms 115 and the target ciliary structure can be performed (box 1025). In some implementations, adjustment of the force translation arms 115 can be performed (box 1030) and further post-operative assessment(s) of the engagement performed (arrow 1036). Post-operative assessment of the optical fit of the lens can be performed until the desired fit is achieved (box 1035). In some implementations, the optical power of the lens can be adjusted in situ (box 1040). Following adjustments, further post-operative assessment of the optical fit of the lens can be performed until the desired power is achieved (arrow 1046). It should be appreciated that the assessment and adjustment of the lens fit and power, whether performed intra-operatively or post-operatively, can be completely independent of one another so much so that either can be performed without the other. In certain circumstances, the lens power can be assessed and adjusted without the assessment of the lens fit. In other circumstances, the lens fit can be assessed and adjusted without the assessment of the lens power.

The position of the AIOL can be assessed intra-operatively as well as post-operatively using imaging techniques known in the art. One or more components of the AIOL may be formed of materials, such as silicone, that is not clearly visible during evaluation using imaging techniques such as UBM. Therefore, the AIOL can incorporate one or more visualization markers 1100 to aid in the assessment of the position of the lens. The markers 1100 can be made of a material that is visible under one or more types of imaging procedures. In some implementations, the markers 1100 can be formed of polyimide and can be located on or in one or more regions of the lens 100. The material of the visualization markers 1100 can be visually distinct under imaging compared to one or more components of the remainder of the lens formed, for example, of another material such as silicone. The markers 1100 can be integrated into an internal skeletal structure such as the structures described to reinforce the lens body 105, the force transfer arm 115, the static element 150, or stabilization system 120. Alternatively, the markers 1100 may not contribute to the function of the lens, but may be additional components added specifically to enhance visualization. Alternatively, the markers 1100 may be geometric modifications to any of the lens components that are easily identifiable with intra-ocular imaging techniques known to the art. For example, a divot or through hole may be placed in a silicone structure that has an otherwise continuous surface. Such markers 1100 can guide a physician in taking measurements of the lens 100 to ensure appropriate fit. The highly visible markers 1100 can be placed strategically in different areas of the lens in a way that illuminates the position of each structure relative to other lens components and to naturally occurring anatomical structures. The markers 1100 may also be useful to visualize dynamic movement within the lens. For instance, two markers may be positioned such that their relative positions depend accommodative state of the lens. Thus, diagnostic imaging of the markers can be used to show the lens transitioning from an accommodative to disaccommodative state.

Figure 11A:
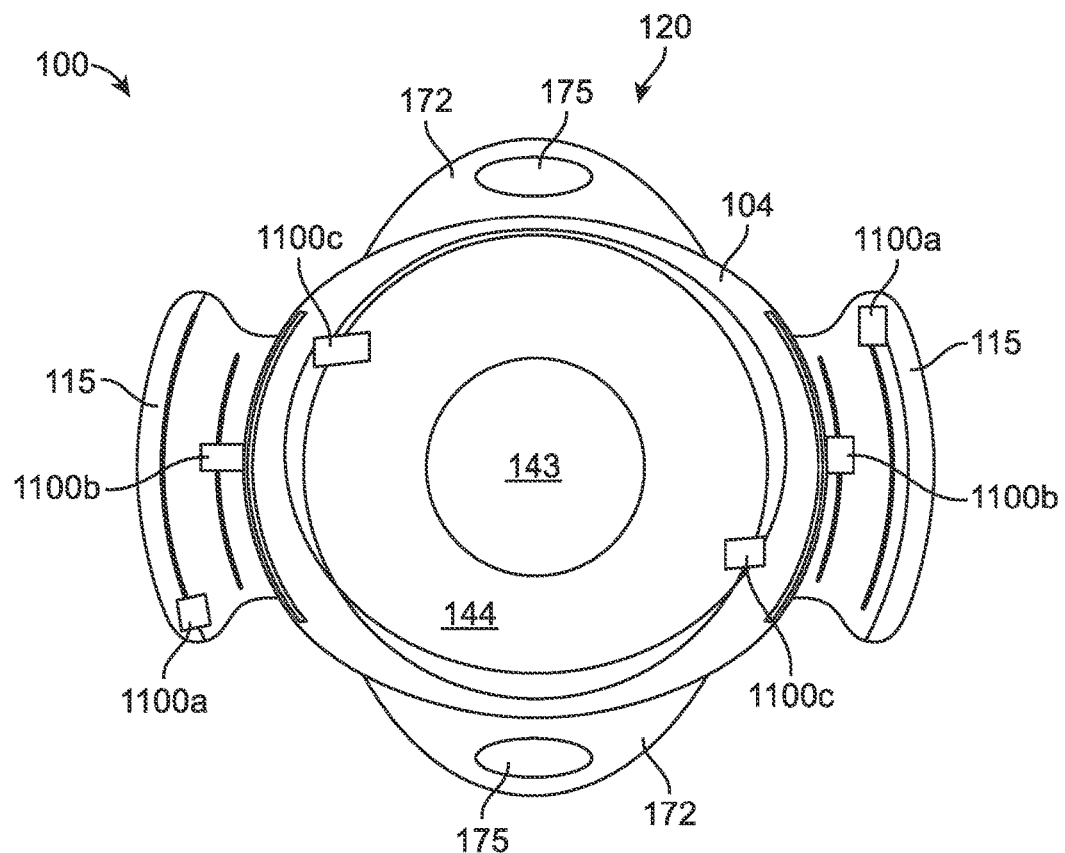
FIGS. 11A-11B illustrate a top plan view and a side elevational view, respectively, of an implementation of a lens having a plurality of visualization markers.
Figure 11B:
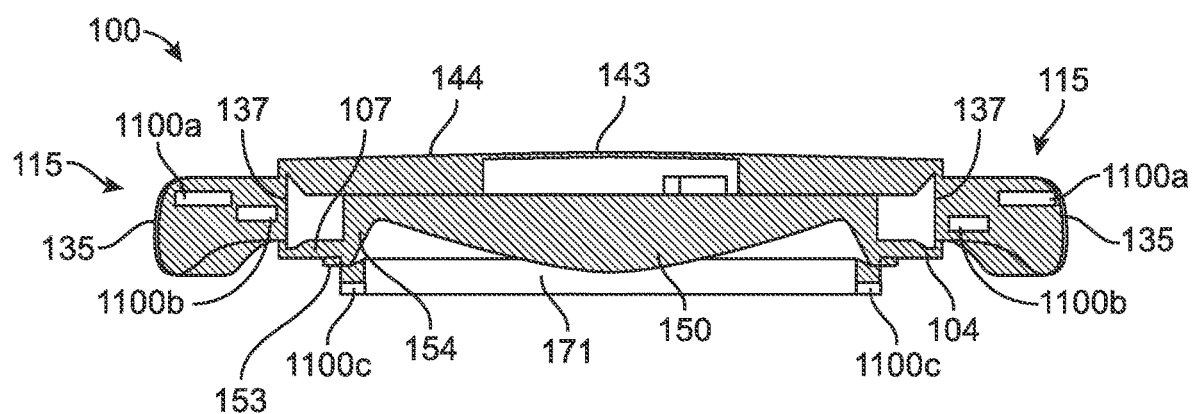
Figure 11C:
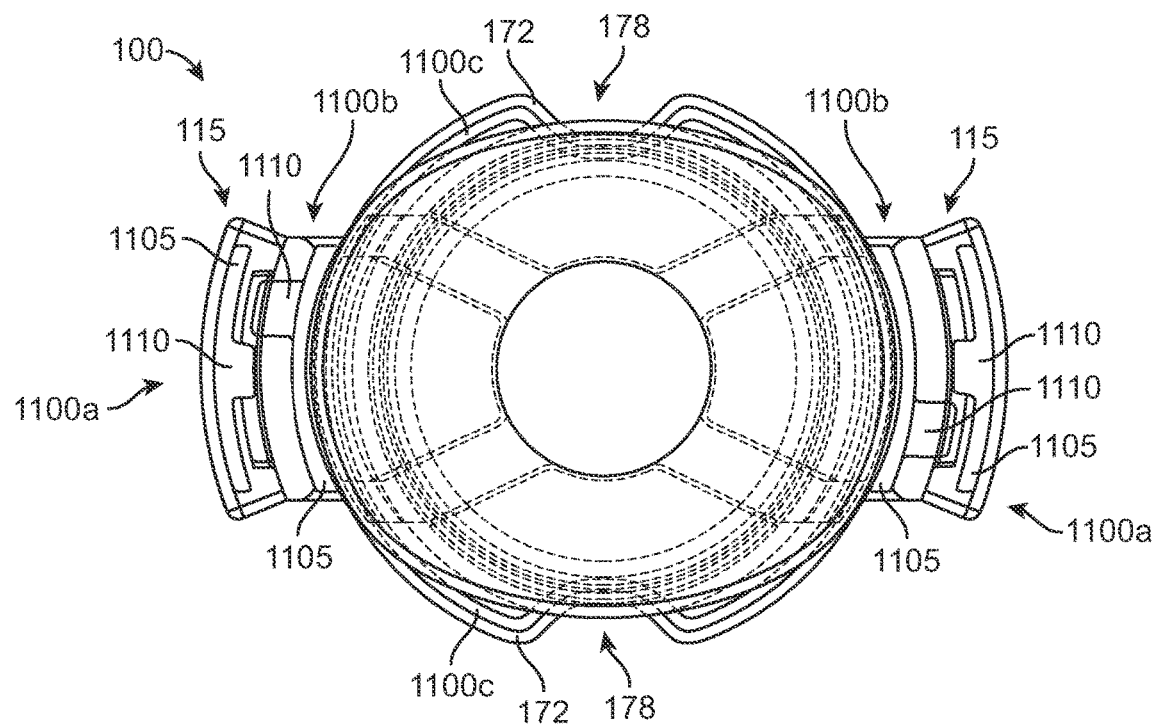
FIGS. 11C-11D illustrate a top plan view and a side elevational view, respectively, of an implementation of a lens having a plurality of visualization markers.
Figure 11D:
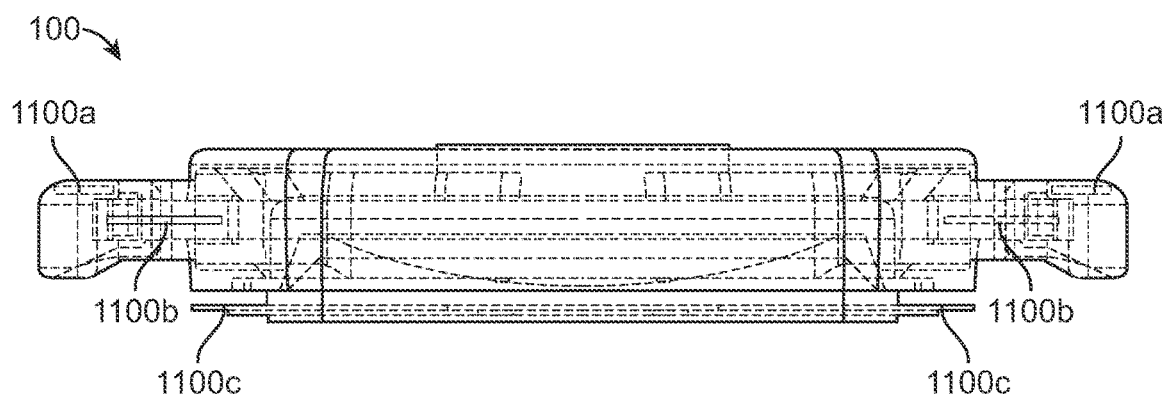
Figure 11E:
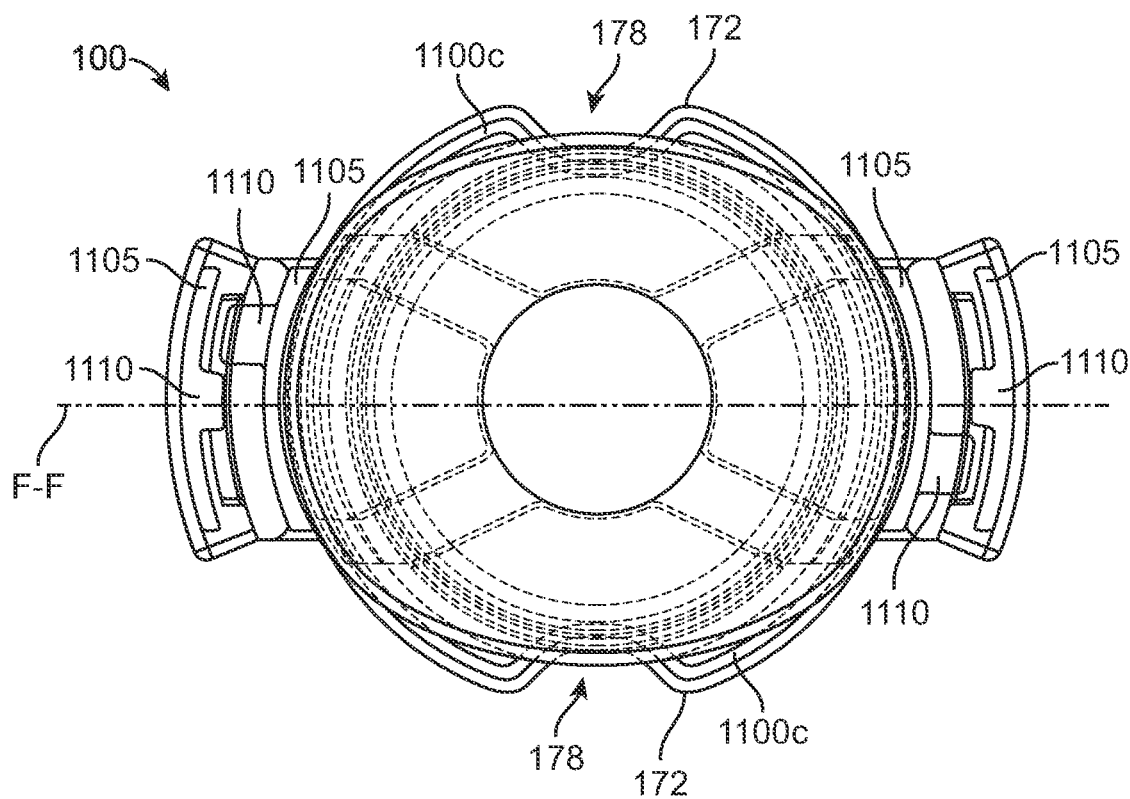
FIGS. 11E-11L illustrate top plan and side elevational views of various configurations of visualization markers.
Figure 11F:
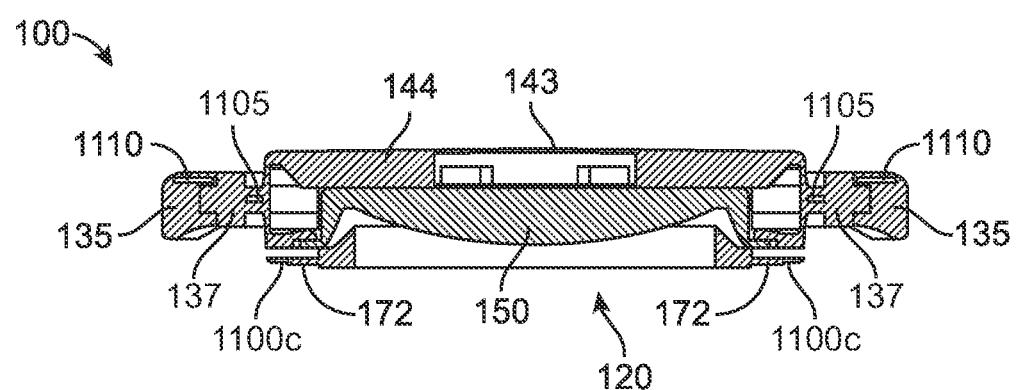
Figure 11G:
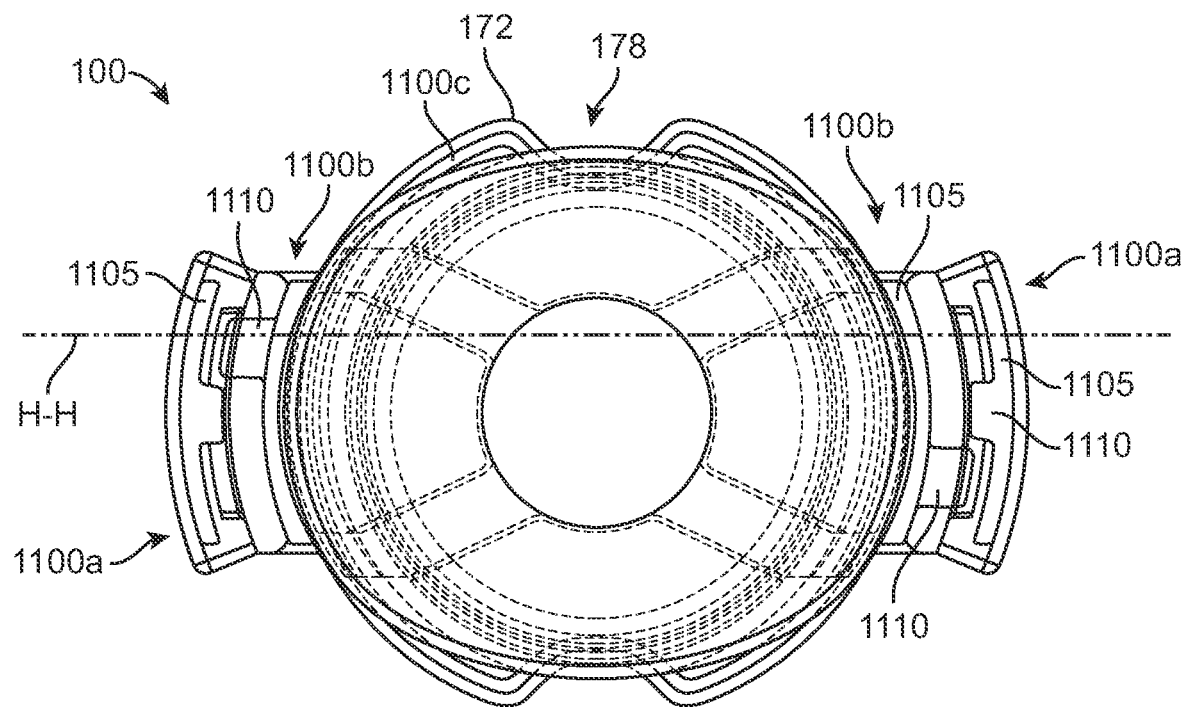
Figure 11H:
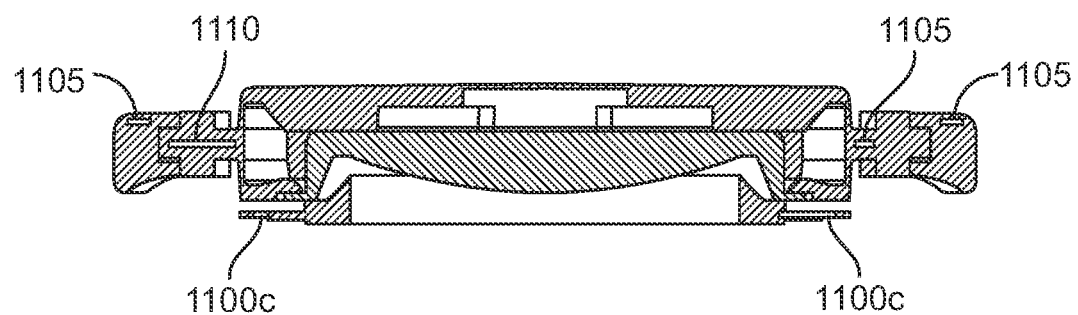
Figure 11I:
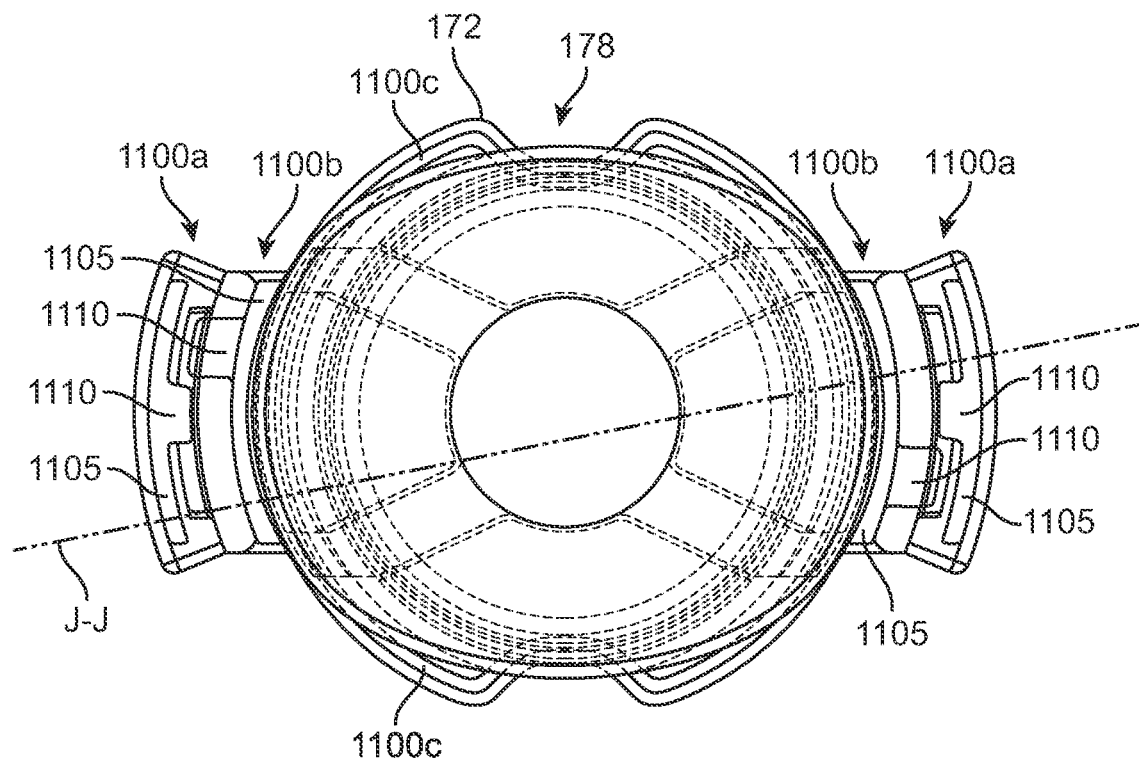
Figure 11J:
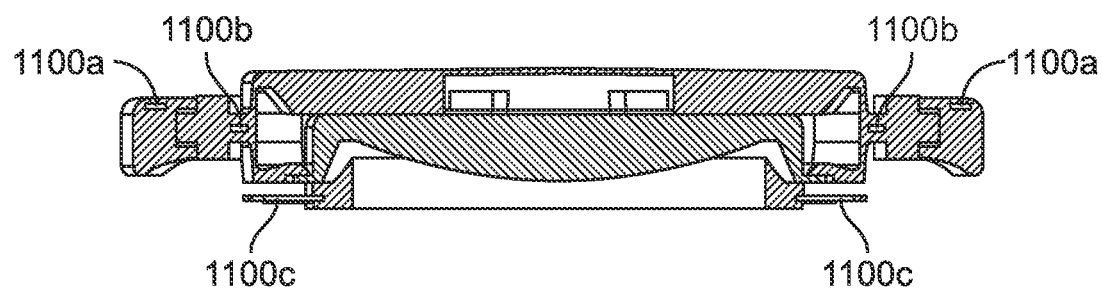
Figure 11K:
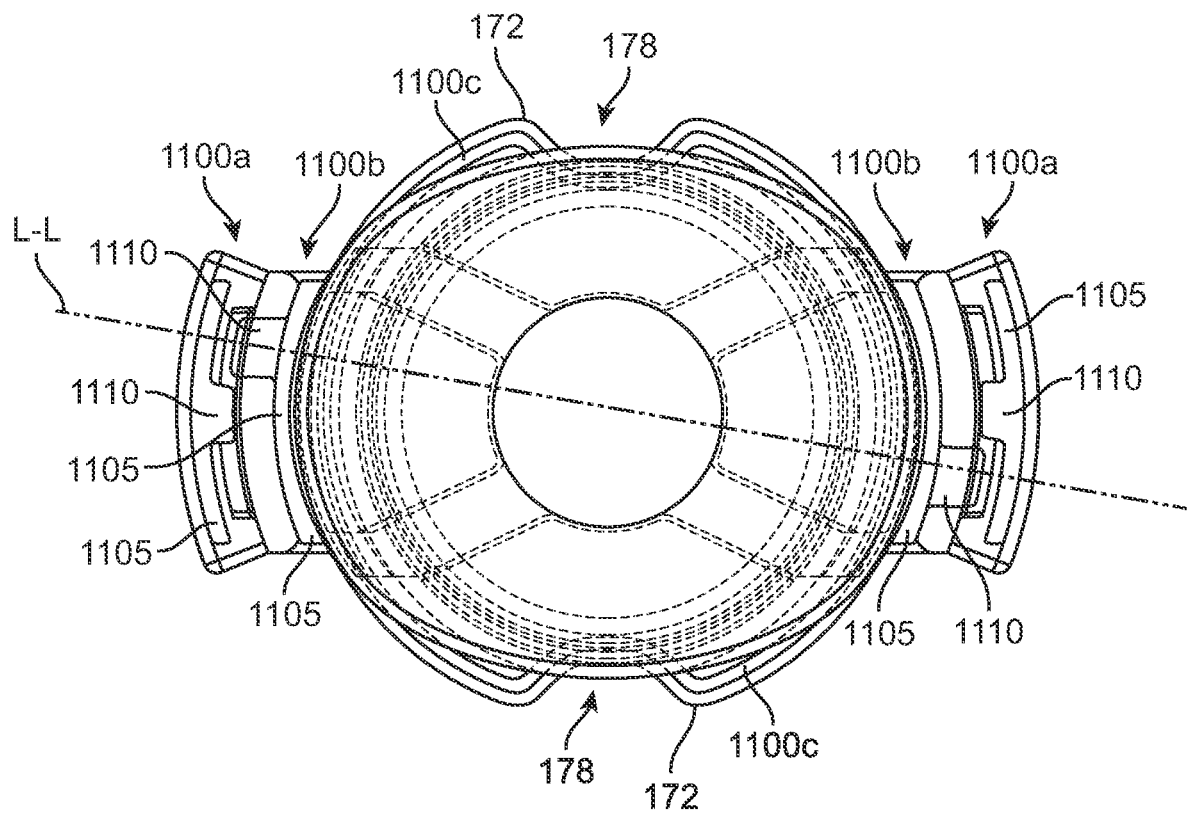
Figure 11L:
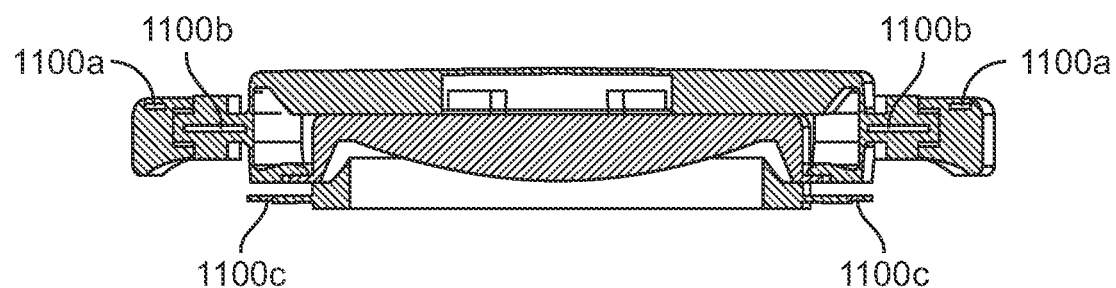

The visualization markers 1100 can assist the operator in visualizing the correct plane of the AIOL as well as capture images of the force translation arms 115 along the longest axis. The visualization markers 1100 can assist in the capture and analysis of images to clearly identify the distance of the force translation arms 115 and the vertical position of them relative to the ciliary processes. The visualization markers 110 can also aid in analyzing the movement of the force translation arms 115 during accommodation following implantation. FIGS. 11A-11L illustrate implementations of a lens 100 incorporating one or more visualization markers 1100 positioned in various points on the lens 100. The visualization markers 1100 can have any of a variety of shapes and sizes to provide additional information related to the orientation and position of the various components of the lens relative to the eye anatomy. FIGS. 11A-11B illustrate a top plan view and a side elevational view, respectively, of an implementation of a lens 100 having a plurality of visualization markers 1100. In this implementation, the lens 100 can include first visualization markers 1100a near the outer, contact region 135 of the force translation arms 115 and second visualization markers 1100b near the inner, contact portion 137 of the force translation arms 115. A third visualization marker 1100c can be located at another location of the lens such as on part of the stabilization system 120 such as on the flange 172 or another portion of lens such as the ring of the posterior element 150. FIGS. 11C-11D illustrates a top plan view and a side elevational view, respectively, of another implementation of a lens 100 having a plurality of visualization markers 1100. The lens 100 can include three sets of visualization markers 1100a, 1100b, 1100c. Each of the visualization markers 1100a, 1100b, 1100c can have variable width or thickness such that they provide a differentiating cross-sectional view or pattern under imaging depending on where the cross-section is taken. For example, the visualization marker 1100a positioned near the outer, contact region 135 of the force translation arms 115 can have a narrow portion 1105 and a wider portion 1110. Similarly, the second visualization marker 1100b positioned near the inner, contact portion 137 of the force translation arms 115 can have a narrow portion 1105 and a wider portion 1110. The third visualization marker 1100c positioned along a flange 172 of the stabilization system 120 can also have a narrow portion 1105 and a wider portion 1110. These narrow and wide portions provide patterns of short and long, respectively, when the lens is imaged in cross-section. For example, the cross-sectional image of the plurality of visualization markers 1100a, 1100b, 1100c of FIG. 11E when taken along line F-F provides a pattern that is "long-short-short" on a first side and "short-short-long" on the opposite side (see FIG. 11F). However, if the cross-sectional image of the plurality of visualization marker 1100a, 1100b, 1100c of FIG. 11G is taken along line H-H, the pattern provided by the markers changes to "short-long-short" and "long-short-short" (see FIG. 11H). Similarly, if the cross-sectional image of the plurality of visualization markers 1100a, 1100b, 1100c of FIG. 11I is taken along line J-J, the pattern provided changes to "short-short-long" and "long-short-short". And if the cross-sectional image of the plurality of visualization markers 1100a, 1100b, 1100c of FIG. 11K is taken along line L-L, the pattern provided changes to "short-long-short" and "short-long-short" and so on.

Suitable materials or combinations of materials for the preparation of the various components of the devices disclosed herein are provided throughout. It should be appreciated that other suitable materials are considered. U.S. Patent Publication Nos. 2009/0234449, 2009/0292355 and 2012/0253459, which are each incorporated by reference herein in their entirety, provide further examples of other materials suitable for forming certain components for the devices described herein. One or more components of the lens body 105 can be integral with one another in that they are formed of the same material. For example, the internal supports 110 can be thickened regions of the perimeter region 144 of the anterior optic 145. Similarly, the shape deformation membrane 140 and annular element 104 can be integral with one another having certain physical properties, such as a thickness or flexibility, to provide a desired function. Alternatively, one or more of the components of the lens body 105 can be coupled together by techniques known in the art. As such, the one or more components of the lens body 105 can be formed of the same materials or different materials. One or more of the supports 110, perimeter region 144, dynamic membrane 145, and shape deformation membrane 140 can be formed of an optically clear, low modulus elastomer such as silicone, urethane, flexible acrylic, or flexible inelastic film such as polyethylene, as well as halogenated elastomers such as fluorosilicone elastomers. The biocompatible optical fluid can be a non-compressible liquid or gel that is clear and transparent in the visible spectrum, for example, silicone fluids and gels, functionalized silicone fluids and gels (for example, halogen, i.e., fluorinated silicones, aromatic, i.e., phenyl functionalized silicones, etc.), hydrocarbon and functionalized hydrocarbons, such as long chain hydrocarbons, halogenated hydrocarbons, such as fluorinated and partially fluorinated hydrocarbons, aqueous systems, both fluids and gels, whose refractive index (RI) has been increased by the additions of water-soluble or water swellable polymers, bio-polymer swellable additives such as cellulose, as well as organic or inorganic additives that form nanostructures to increase refractive index. In some implementations, the optical fluid within the sealed chamber 155 has a refractive index higher than 1.37. In other implementations, the optical fluid within the sealed chamber 155 has a refractive index between 1.37-1.57. In other implementations, the optical fluid within the sealed chamber 155 has a refractive index between 1.37-1.60. In a first implementation, the optical fluid filling the sealed chamber 155 is a fluorosilicone oil and the components forming the sealed chamber 155 (e.g. inner-facing surfaces of the shape deformation membrane 140, the static element 150, the inner supports 110, the perimeter region 144 and the dynamic membrane 143 of the anterior optic 145) are formed of a silicone elastomer. In a second implementation, the optical fluid filling the sealed chamber 155 is a silicone oil and the components forming the sealed chamber 155 are formed of a fluorosilicone elastomer. In a third implementation, the optical fluid filling the sealed chamber 155 is an aromatic or phenyl-substituted oil such as phenylsilicone oil and the components forming the sealed chamber 155 are formed of a halogenated silicone elastomer such as fluorosilicone elastomer. The combinations of materials are chosen to optimize stability of the lens, prevent swelling and maintaining optimum refractive index. In some implementations, the force translation arms 115 can be a rigid polymer such as silicone, polyurethane, PMMA, PVDF, PDMS, polyamide, polyimide, polypropylene, polycarbonate, etc., or combinations thereof. In some implementations, the force translation arms 115 can be an element reinforced with PMMA. In some implementations, the AIOL is formed of all silicone materials including the posterior static element 150 and the force translation arms 115. The stabilization system 120 can be formed of a more rigid silicone or can be formed of or incorporate polyimide. For example, the stabilization haptics 160 and the flange 172 can be polyimide.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detain in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various placed throughout this specification are not necessarily referring to the same embodiment or implementation. Furthermore, the particular features, structures, configurations, or characteristics may be combined in any suitable manner in one or more implementations.

The devices and systems described herein can incorporate any of a variety of features. Elements or features of one implementation of a device and system described herein can be incorporated alternatively or in combination with elements or features of another implementation of a device and system described herein as well as the various implants and features described in U.S. Patent Publication Nos. 2009/0234449, 2009/0292355, 2012/0253459, and PCT Patent Publication No. WO 2015/148673, which are each incorporated by reference herein in their entireties. For the sake of brevity, explicit descriptions of each of those combinations may be omitted although the various combinations are to be considered herein. Additionally, the devices and systems described herein can be positioned in the eye and need not be implanted specifically as shown in the figures or as described herein. The various devices can be implanted, positioned and adjusted etc. according to a variety of different methods and using a variety of different devices and systems. The various devices can be adjusted before, during as well as any time after implantation. Provided are some representative descriptions of how the various devices may be implanted and positioned, however, for the sake of brevity explicit descriptions of each method with respect to each implant or system may be omitted.

The use of relative terms throughout the description may denote a relative position or direction or orientation and is not intended to be limiting. For example, "distal" may indicate a first direction away from a reference point. Similarly, "proximal" may indicate a location in a second direction opposite to the first direction. Use of the terms "front," "side," and "back" as well as "anterior," "posterior," "caudal," "cephalad" and the like or used to establish relative frames of reference, and are not intended to limit the use or orientation of any of the devices described herein in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. An accommodating intraocular lens device for treatment of an eye, the device comprising:
a lens body comprising:
a first membrane comprising a first perimeter region and a central, accommodating surface configured to outwardly bow;
a shape deformation membrane extending along an arc and configured to undergo displacement relative to the first perimeter region of the first membrane;
a static element having a second perimeter region, the static element positioned opposite the first membrane; and
a fixed volume of optical fluid,
wherein an inner surface of the first membrane, an inner surface of the shape deformation membrane and an inner surface of the static element collectively form a sealed chamber of the lens body that contains the fixed volume of optical fluid;
a stabilization system comprising a flange having an inner region positioned posteriorly relative to a posterior region of the lens body and an outer region extending radially outward from the inner region to an outermost edge, wherein a channel is formed between a posterior-facing surface of the lens body and an anterior-facing surface of the inner region of the flange, at least the outermost edge of the flange configured to be positioned inside a capsular bag of the eye upon implantation of the device in an eye; and
a first force translation arm separate from a second force translation arm positioned symmetrically opposite the first force translation arm, each of the first and second force translation arms having a free end configured to engage a ciliary structure of the eye outside the capsular bag when the lens device is implanted in the eye such that an optical axis of the lens body is substantially aligned with a visual axis of the eye, wherein the first and second force translation arms are movable relative to the lens body to cause inward movement of the shape deformation membrane.

2. The device of claim 1, wherein the stabilization system further comprises an annular ring structure coupled to an internal support positioned near the first perimeter region.

3. The device of claim 1, wherein the flange is positioned a distance away from the first and second force translation arms.

4. The device of claim 3, wherein the flange comprises first and second flanges positioned opposite each other, wherein the first and second flanges are positioned between the first and second force translation arms.

5. The device of claim 1, wherein the inner region of the flange is positioned in a posterior position relative to the first and second force translation arms.

6. The device of claim 5, wherein, upon implantation of the device in an eye, the outermost edge of the flange is sized and arranged on the device so as to be positioned posterior to an anterior portion of the capsular bag and the first and second force translation arms are sized and arranged on the device so as to be positioned anterior to the anterior portion of the capsular bag.

7. The device of claim 5, wherein upon implantation of the device in an eye the channel formed between the posterior-facing surface of the lens body and the anterior-facing surface of the inner region of the flange is sized to receive a capsular bag edge formed by a capsulorhexis in the capsular bag.

8. The device of claim 7, wherein the outermost edge of the flange comprises an outer elevation projecting anteriorly relative to the inner region of the flange, the outer elevation being configured to engage against a posterior-facing internal surface of an anterior capsule upon implantation of the device in an eye.

9. The device of claim 5, wherein the flange further comprises an interruption configured to provide a path of fluid egress from the capsular bag.

10. The device of claim 5, wherein the outermost edge of the flange lies in a plane posterior to an anterior-facing surface of the first and second force translation arms.

11. The device of claim 1, wherein the shape deformation membrane moves a distance of between about 50 µm to about 100 µm, optionally wherein the distance moved causes a change in power of the lens body by at least ±3 diopters.

12. The device of claim 1, wherein the central, accommodating surface of the first membrane is a reduced thickness region prone to give way upon increased internal pressure within the sealed chamber or upon application of pressure by the optical fluid against the inner surface of the first membrane.

13. The device of claim 1, wherein the optical fluid in the sealed chamber is non-compressible and presses against the inner surface of the first membrane to cause the outward bowing of the first membrane upon inward movement of the shape deformation member.

14. The device of claim 1, further comprising an internal support configured to mechanically isolate optical components of the lens body from distortion during movement of the first and second force translation arms relative to the lens body and from distortion due to stresses on the stabilization system.

15. The device of claim 14, wherein the internal support comprises a plurality of internal supports surrounded by the optical fluid.

16. The device of claim 14, wherein the internal support comprises at least one internal support comprising a first side and a second side, the internal support sealed to the first perimeter region of the first membrane on the first side and sealed to the second perimeter region of the static element on the second side.

17. The device of claim 14, wherein the internal support forms a partition within the sealed chamber dividing the sealed chamber into a deformable region and a central region and wherein the deformable region is located outside an optic zone of the lens body.

18. The device of claim 1, wherein the first membrane comprises a variable thickness membrane.

19. A system comprising the device of claim 1, wherein the device is positioned anterior to a second intraocular lens that is a non-accommodating lens.

20. An accommodating intraocular lens device for treatment of an eye, the device comprising:
a lens body comprising:
a first membrane comprising a first perimeter region and a central, accommodating surface configured to outwardly bow;
a shape deformation membrane extending along an arc and configured to undergo displacement relative to the first perimeter region of the first membrane;

a static element having a second perimeter region, the static element positioned opposite the first membrane; and a fixed volume of optical fluid, wherein an inner surface of the first membrane, an inner surface of the shape deformation membrane and an inner surface of the static element collectively form a sealed chamber of the lens body that contains the fixed volume of optical fluid;

a stabilization system comprising a first flange and a second flange positioned opposite the first flange, each of the first and second flanges having an inner region positioned posteriorly relative to a posterior region of the lens body and an outer region extending radially outward from the inner region to an outermost edge, wherein a channel is formed between a posterior-facing surface of the lens body and an anterior-facing surface of the inner region of the first and second flanges, at least the outermost edge of the first and second flanges configured to be positioned inside a capsular bag of the eye upon implantation of the device in an eye; and a first force translation arm and a second force translation arm positioned opposite the first force translation arm, each having a free end configured to engage a ciliary structure of the eye outside the capsular bag when the lens device is implanted in the eye such that an optical axis of the lens body is substantially aligned with a visual axis of the eye, wherein the first and second force translation arms are movable relative to the lens body to cause inward movement of the shape deformation membrane, and wherein the first flange is positioned a distance away and between the first and second force translation arm on a first side and the second flange is positioned a distance away and between the first and second force translation arms on a second, opposite side.

21. An accommodating intraocular lens device for treatment of an eye, the device comprising:

a lens body comprising:
a first membrane comprising a first perimeter region and a central, accommodating surface configured to outwardly bow;
a shape deformation membrane extending along an arc and configured to undergo displacement relative to the first perimeter region of the first membrane;
a static element having a second perimeter region, the static element positioned opposite the first membrane; and
a fixed volume of optical fluid, wherein an inner surface of the first membrane, an inner surface of the shape deformation membrane and an inner surface of the static element collectively form a sealed chamber of the lens body that contains the fixed volume of optical fluid;

a stabilization system comprising a flange having an inner region positioned posteriorly relative to a posterior region of the lens body and an outer region extending radially outward from the inner region to an outermost edge, wherein a channel is formed between a posterior-facing surface of the lens body and an anterior-facing surface of the inner region of the flange, at least the outermost edge of the flange configured to be positioned inside a capsular bag of the eye upon implantation of the device in an eye; and a force translation arm having a free end configured to engage a ciliary structure of the eye outside the capsular bag when the lens device is implanted in the eye such that an optical axis of the lens body is substantially aligned with a visual axis of the eye, wherein the force translation arm is movable relative to the lens body to cause inward movement of the shape deformation membrane, wherein the inner region of the flange is positioned in a posterior position relative to the force translation arm, wherein, upon implantation of the device in an eye, the outermost edge of the flange is sized and arranged on the device so as to be positioned posterior to an anterior portion of the capsular bag and the force translation arm is sized and arranged on the device so as to be positioned anterior to the anterior portion of the capsular bag.

22. An accommodating intraocular lens device for treatment of an eye, the device comprising:

a lens body comprising:
a first membrane comprising a first perimeter region and a central, accommodating surface configured to outwardly bow;
a shape deformation membrane extending along an arc and configured to undergo displacement relative to the first perimeter region of the first membrane;
a static element having a second perimeter region, the static element positioned opposite the first membrane; and
a fixed volume of optical fluid, wherein an inner surface of the first membrane, an inner surface of the shape deformation membrane and an inner surface of the static element collectively form a sealed chamber of the lens body that contains the fixed volume of optical fluid;

a stabilization system comprising a flange having an inner region positioned posteriorly relative to a posterior region of the lens body and an outer region extending radially outward from the inner region to an outermost edge, wherein a channel is formed between a posterior-facing surface of the lens body and an anterior-facing surface of the inner region of the flange, at least the outermost edge of the flange configured to be positioned inside a capsular bag of the eye upon implantation of the device in an eye; and a force translation arm having a free end configured to engage a ciliary structure of the eye outside the capsular bag when the lens device is implanted in the eye such that an optical axis of the lens body is substantially aligned with a visual axis of the eye, wherein the force translation arm is movable relative to the lens body to cause inward movement of the shape deformation membrane, wherein the inner region of the flange is positioned in a posterior position relative to the force translation arm, wherein upon implantation of the device in an eye the channel formed between the posterior-facing surface of the lens body and the anterior-facing surface of the inner region of the flange is sized to receive a capsular bag edge formed by a capsulorhexis in the capsular bag.

23. An accommodating intraocular lens device for treatment of an eye, the device comprising:

a lens body comprising:
a first membrane comprising a first perimeter region and a central, accommodating surface configured to outwardly bow;
a shape deformation membrane extending along an arc and configured to undergo displacement relative to the first perimeter region of the first membrane;

a static element having a second perimeter region, the static element positioned opposite the first membrane; and a fixed volume of optical fluid, wherein an inner surface of the first membrane, an inner surface of the shape deformation membrane and an inner surface of the static element collectively form a sealed chamber of the lens body that contains the fixed volume of optical fluid;

a stabilization system comprising a flange having an inner region positioned posteriorly relative to a posterior region of the lens body and an outer region extending radially outward from the inner region to an outermost edge, wherein a channel is formed between a posterior-facing surface of the lens body and an anterior-facing surface of the inner region of the flange, at least the outermost edge of the flange configured to be positioned inside a capsular bag of the eye upon implantation of the device in an eye; and a force translation arm having a free end configured to engage a ciliary structure of the eye outside the capsular bag when the lens device is implanted in the eye such that an optical axis of the lens body is substantially aligned with a visual axis of the eye, wherein the force translation arm is movable relative to the lens body to cause inward movement of the shape deformation membrane, wherein the inner region of the flange is positioned in a posterior position relative to the force translation arm, wherein the flange further comprises an interruption configured to provide a path of fluid egress from the capsular bag.

* * * * *